(12) United States Patent
Zuk, Jr.

(10) Patent No.: US 7,546,925 B1
(45) Date of Patent: Jun. 16, 2009

(54) DISPOSABLE VACUUM FILTRATION APPARATUS CAPABLE OF DETECTING MICROORGANISMS AND PARTICULATES IN LIQUID SAMPLES

(75) Inventor: Peter Zuk, Jr., Harvard, MA (US)

(73) Assignee: Roush Life Sciences, LLC, Livonia, MI (US)

( * ) Notice: Subject to any disclaimer, the term of this patent is extended or adjusted under 35 U.S.C. 154(b) by 807 days.

(21) Appl. No.: 11/171,724

(22) Filed: Jun. 30, 2005

Related U.S. Application Data

(63) Continuation-in-part of application No. 10/263,838, filed on Oct. 3, 2002, now Pat. No. 6,913,152, which is a continuation-in-part of application No. 10/005,856, filed on Dec. 4, 2001, now abandoned.

(60) Provisional application No. 60/297,832, filed on Jun. 12, 2001, provisional application No. 60/251,130, filed on Dec. 4, 2000.

(51) Int. Cl.
  *B01D 29/05* (2006.01)
  *B01D 63/08* (2006.01)

(52) U.S. Cl. ............ 210/406; 210/474; 210/489; 422/101; 422/102

(58) Field of Classification Search ............ 422/101, 422/102; 435/308.1, 297.5; 210/474, 489, 210/406
See application file for complete search history.

(56) References Cited

U.S. PATENT DOCUMENTS

| | | | | |
|---|---|---|---|---|
| 3,010,583 A | * | 11/1961 | Kenyon | 210/406 |
| 5,234,585 A | * | 8/1993 | Zuk, Jr. | 210/188 |
| 5,308,483 A | * | 5/1994 | Sklar et al. | 210/232 |
| 6,358,730 B1 | * | 3/2002 | Kane | 435/297.5 |
| 6,443,314 B2 | * | 9/2002 | Shiraiwa et al. | 210/474 |

* cited by examiner

*Primary Examiner*—Terry K Cecil
(74) *Attorney, Agent, or Firm*—Bromberg & Sunstein LLP

(57) ABSTRACT

A vacuum filtration apparatus (900) for detecting microorganisms and particulates in liquid samples. The apparatus includes a base (901), an absorbent pad (991), a filter (990), a funnel (930), and a lid (960). The funnel is releasably attached to the base, and may contain an integral flexible seal for releasably sealing the filter to the base. The outer wall of the lid may be segmented to make it flexible, this flexibility allows it to be releasably attached to the funnel or the base. The apparatus is designed so that any funnel will fit any base, and any lid will fit any base or any funnel when all parts are manufactured to normal tolerances. The apparatus may be configured to keep the filter wrinkle free in both the dry and wet states.

1 Claim, 46 Drawing Sheets

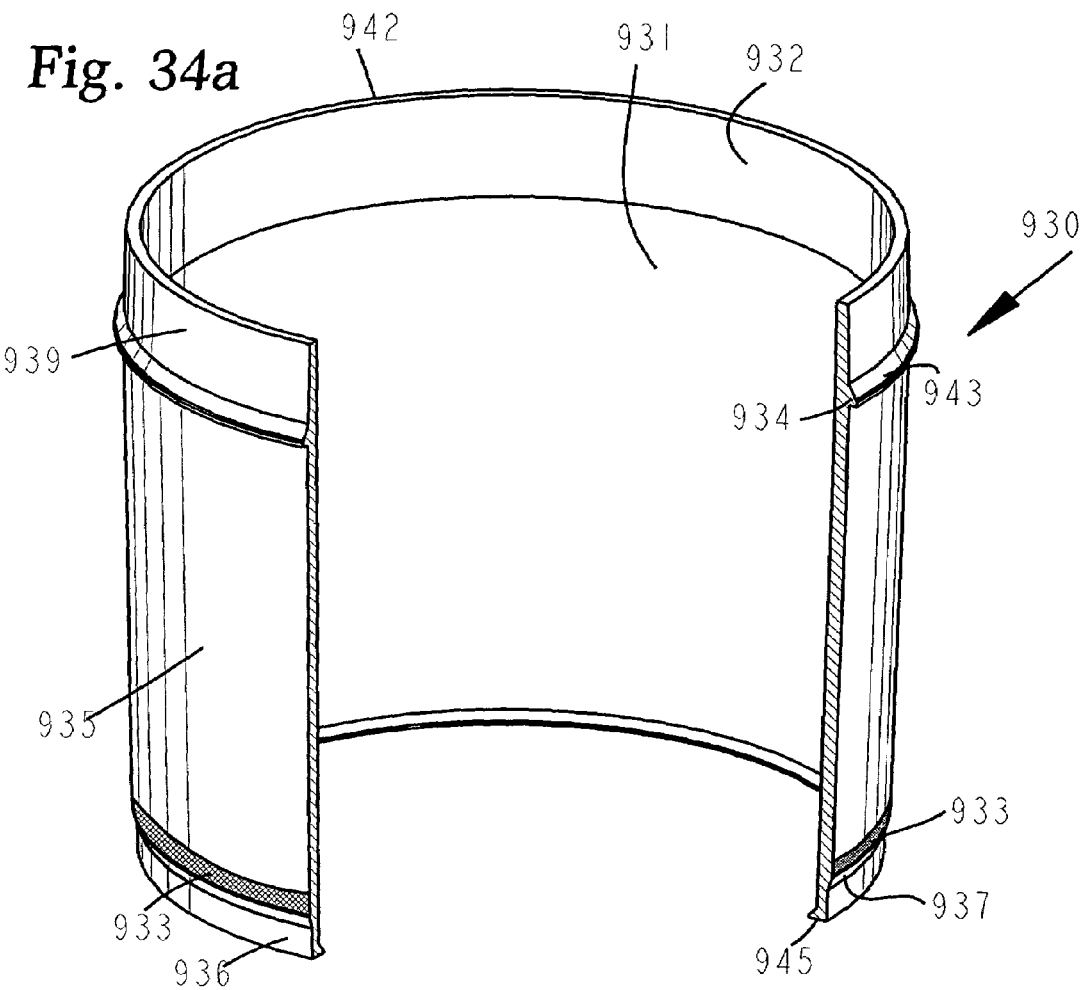
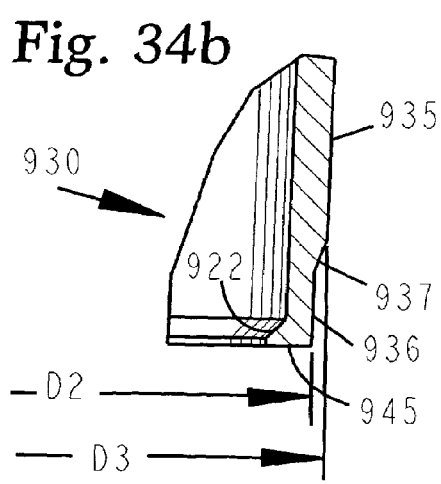
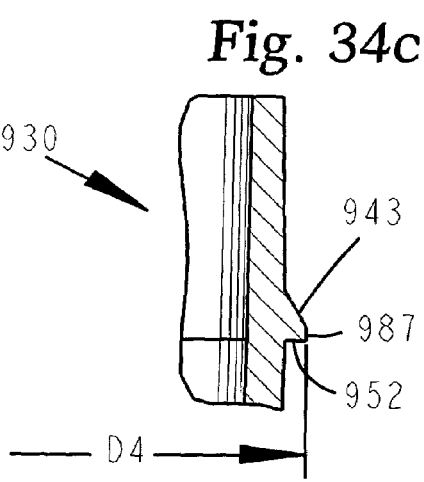

Fig. 54
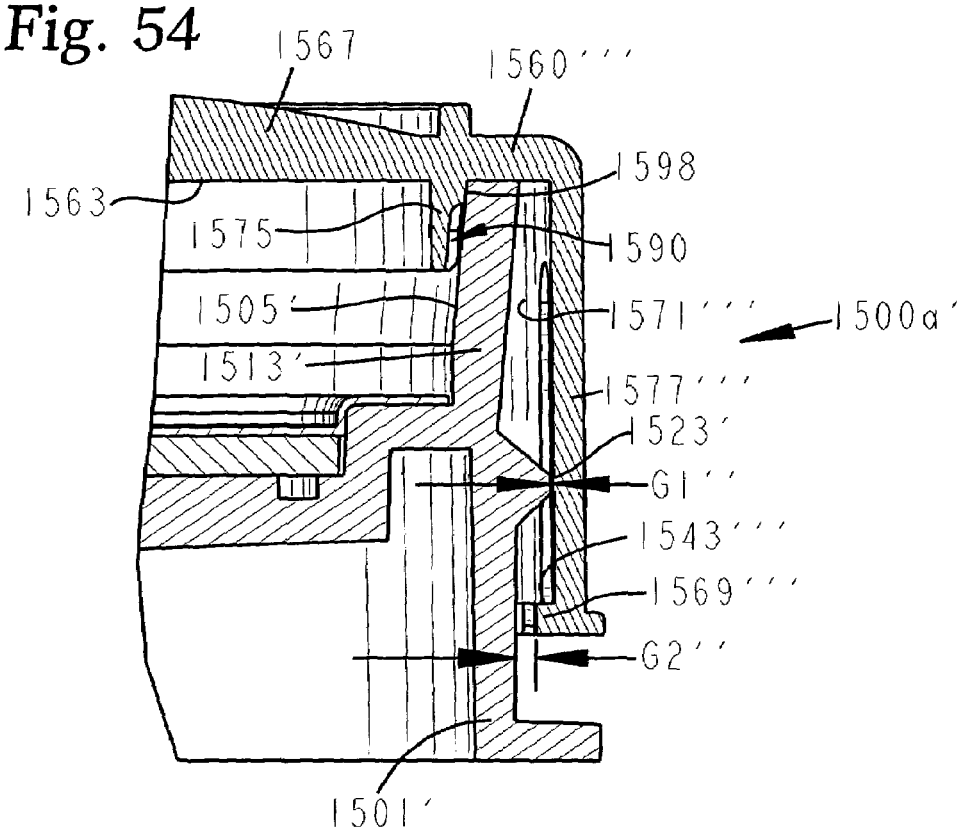
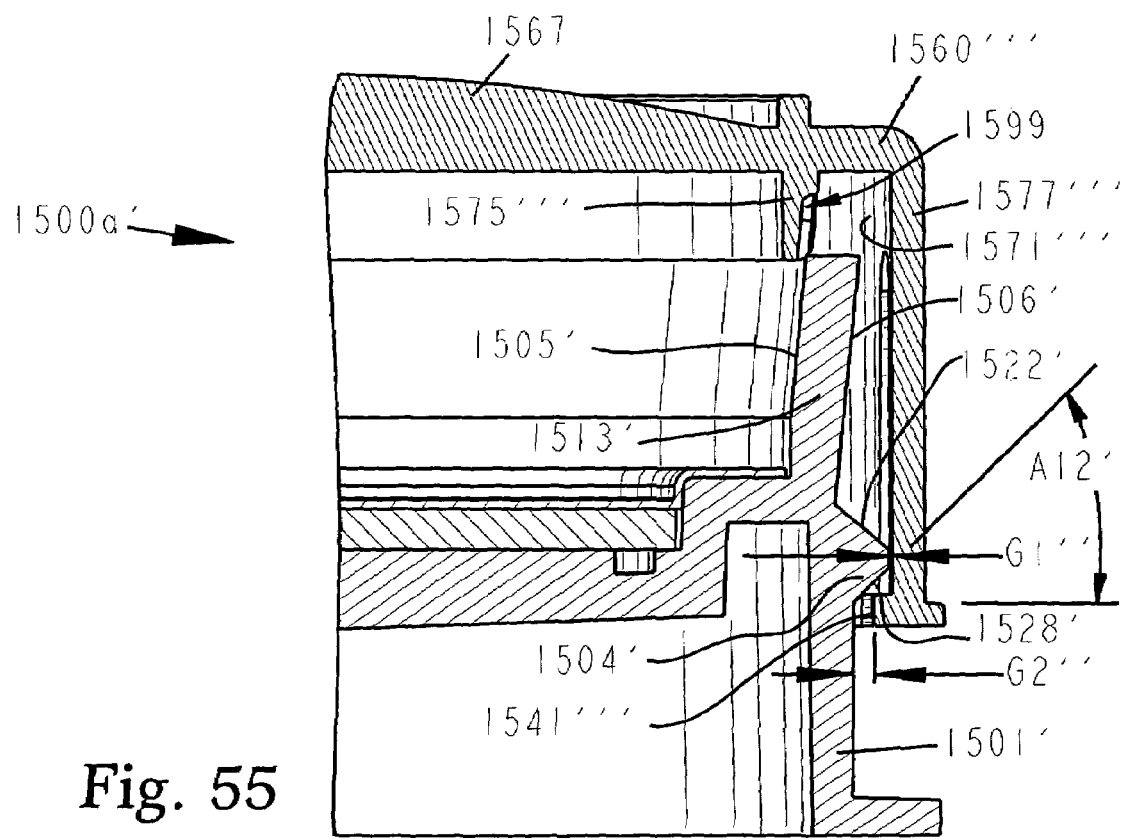
Fig. 55

DISPOSABLE VACUUM FILTRATION APPARATUS CAPABLE OF DETECTING MICROORGANISMS AND PARTICULATES IN LIQUID SAMPLES

This is a Continuation-In-Part of application Ser. No. 10/263,838, filed Oct. 3, 2002, now U.S. Pat. No. 6,913,152, which was a Continuation-In-Part of application Ser. No. 10/005,856, filed Dec. 4, 2001, now abandoned, in which applicant claimed priority of Provisional Application No. 60/251,130, filed on Dec. 4, 2000, and of Provisional Application No. 60/297,832, filed on Jun. 12, 2001.

BACKGROUND OF THE INVENTION

This invention relates to the filtration field, and more particularly, to an improved disposable vacuum filtration apparatus capable of detecting microorganisms and particulates in liquid samples. There are commercially available disposable vacuum filtration devices for detecting microorganisms and particulates in liquid samples available today. The currently available disposable vacuum filtration devices for detecting microorganisms and particulates in liquid samples contain a base section, a removable funnel section, and a removable lid. An absorbent pad, and microporous filter are inserted into the base section. The absorbent pad is placed into a well in the base section, and the microporous filter (normally of larger diameter than the absorbent pad) is inserted above the absorbent pad (i.e. on the upstream side of the absorbent pad). The absorbent pad provides support for the microporous filter. The base section also contains a filter support means which provides support for the absorbent pad and provides fluid flow communication between the downstream side of the absorbent pad and an outlet port located at the bottom of the base section. The removable funnel section is press fitted or snapped into the base section. The outer periphery of the microporous filter is either sealed to the base section or sealed between the bottom edge of the funnel section and the base section. The removable lid is press fitted onto the top of the removable funnel section preferably with a fit that allows easy removal, but that does not allow the lid to accidentally separate from the funnel section. These devices are normally sold pre-sterilized. In use the end user preferably removes a sterile vacuum filtration device from its shipping package in a laminar flow hood to prevent contaminating the device. The lid is then removed from the funnel section and a liquid sample to be tested is poured into the funnel section. The lid is then placed back onto the funnel section and the outlet port of the base section is connected to a vacuum means. The vacuum means sucks the liquid through the microporous filter, and through the absorbent pad, and then through the outlet port, into the vacuum means. Either the lid or the funnel section contains a venting means to allow air to replace the liquid in the funnel as vacuum removes the liquid from the funnel. Once all of the liquid sample has been sucked from the vacuum filtration device, the user will remove the vacuum filtration device from the vacuum means, and then remove the lid from the funnel section, and then remove the funnel section from the base section, and then place the lid onto the top of the base section, and then discard the funnel section. The lid should fit onto the top of the base section with a press fit that allows easy removal, but that does not allow the lid to accidentally separate from the base section when the base section is inverted. With the funnel removed, and with the lid attached to the top of the base section, the lid, base section assembly becomes a petri dish. Either the lid or base section should contain a venting means to allow the air in the interior of the base section with the lid attached to communicate with air outside of the base section during the incubation cycle. However in some applications it is desirable that the lid be tightly sealed to the base during the incubation cycle. The user then adds a quantity of growth media to the outlet port of the base section, so that the absorbent pad becomes saturated with growth media. The outlet port of the base section is then plugged with a plug (normally supplied with the device), and the base section with lid and plug is inverted and placed into an oven to incubate, so that any bacteria that was trapped on the upstream side of the microporous filter will grow into colonies to be counted later.

When it is desired to count particles in a liquid sample (for example glass fragments in a soft drink sample), the above steps of adding growth media, and incubation are not necessary. The particles can be counted on the upstream side of the microporous filter once the liquid sample has been filtered through the microporous filter. The microporous filter may contain a grid on its upstream side as an aid in counting either particles or microorganisms.

The currently available vacuum filtration devices for detecting microorganisms and particulates in liquid samples suffer from the following drawbacks:

a) The bottom portion of the funnel section is press fitted to the base section, therefore the outside diameter of the funnel section must match the inside diameter of the base section. This means that the disposable molded parts must be molded to a very high tolerance, which leads to part matching (i.e. funnel sections being individually matched to base sections), high scrap rates, and higher production costs.

b) The lid is press fitted to the top of the funnel section, and to the top of the base section, therefore the outside diameter of the top of the funnel section, and the outside diameter of the top of the base section must match the inside diameter of the lid. Again this means that the disposable molded parts must be molded to a very high tolerance, which leads to part matching (i.e. funnel sections and base sections being individually matched to a lid), high scrap rates, and higher production costs.

c) For different applications different membrane filter types must be used. The different membrane filter types may be of different thickness. Therefore a funnel section, base section matched pair that works with one type of filter may not work with another type of filter.

d) When the membrane filter wets during filtration, it will swell. The currently available devices do not provide a means to keep the swelled filter to remain in intimate contact with the absorbent pad. If the swelling causes the membrane filter to lift away from the absorbent pad, bacteria that is present on the upstream side of the membrane filter in the area that has lifted away from the absorbent pad will not grow when incubated. Therefore, these bacteria will not be detected.

e) All of the above limitations of the present art are exasperated when parts are molded from materials such as polypropylene or polyethylene, which are difficult to mold to tight tolerances.

f) In some applications it is necessary to remove the membrane filter from the base section after filtration is complete, and place said membrane filter into another petri dish for incubation. Currently available devices do not provide an easy means to remove the wet membrane filter from the base section.

It is therefore an object of the present invention to provide a disposable vacuum filtration apparatus for detecting microorganisms and particulates in liquid samples that can be assembled from component parts that have been molded to normal tolerances (i.e. all component parts to be molded within a dimensional tolerance range of ±0.004 of an inch or better). Another object of the present invention is to provide a disposable vacuum filtration apparatus for detecting microorganisms and particulates in liquid samples that can use a filter means of varying thickness, while providing a positive seal to prevent the microorganisms from bypassing the filter means. Another object of the present invention is to provide a disposable vacuum filtration apparatus for detecting microorganisms and particulates in liquid samples that provides a means to keep the downstream side of the filter means in intimate contact with the upstream side of the absorbent pad disposed below it when the filter means and absorbent pad are both wet. Another object of the present invention is to provide a disposable vacuum filtration apparatus for detecting microorganisms and particulates in liquid samples that can be molded from materials such as polypropylene, or polyethylene, or from a combination of materials such as polypropylene and polystyrene. Another object of the present invention is to provide a disposable vacuum filtration apparatus for detecting microorganisms and particulates in liquid samples wherein the filter means can be sealed to the base in a manner that will prevent bypass of the microorganisms around the filter means. Another object of the present invention is to provide a disposable vacuum filtration apparatus for detecting microorganisms and particulates in liquid samples wherein the filter means can be sealed using a compression seal between the base and the funnel in a manner that will prevent bypass of the microorganisms around the filter means.

SUMMARY OF THE INVENTION

The foregoing problems of the prior art are solved, and the objects of the present invention are achieved, by use of a disposable vacuum filtration apparatus constructed in accordance with the principles of the present invention. In accordance with the principles of the present invention, the vacuum filtration apparatus for detecting microorganisms and particulates in liquid samples comprises a base, a funnel, and a lid, and in one embodiment the funnel is an integral part of the base. In several of the embodiments of the present invention an integral flexible sealing means is provided between the funnel and base. This integral flexible sealing means allows any funnel that has been molded with a dimensional tolerance range of ±0.004 of an inch to be mated to any base that has been molded with a dimensional tolerance range of ±0.004 of an inch. In other embodiments of the present invention, the base is made of a sufficiently pliable material to allow a side wall of the base to conform to the shape of the lower portion of the funnel, which allows any funnel that has been molded with a dimensional tolerance range of ±0.004 of an inch to be mated to any base that has been molded with a dimensional tolerance range of ±0.004 of an inch. The funnel may contain an integral flexible sealing means for sealing the filter means with a compression seal between the integral flexible sealing means of the funnel and a seal surface of the base. The lid contains a flexible clamping means that allows any lid that has been molded within a dimensional tolerance range of ±0.004 of an inch to be mated to any base that has been molded within a dimensional tolerance range of ±0.004 of an inch, and that allows any lid that has been molded within a dimensional tolerance range of ±0.004 of an inch to be mated to any funnel that has been molded within a dimensional tolerance range of ±0.004 of an inch.

BRIEF DESCRIPTION OF THE DRAWINGS

These and other objects, features and advantages of the invention will be evident from the following detailed description when read in conjunction with the accompanying drawings in which:

FIG. 1b is a partial cross-sectional view of a bottom portion of the assembly depicted in FIG. 1a;

FIG. 2b is an isometric view, having portions thereof removed, of the lid of the assembles depicted in FIGS. 1a and 2a;

FIG. 3b is a partial cross-sectional view of a top portion of the assembly depicted in FIG. 3a;

FIG. 3c is a partial cross-sectional view of a bottom portion of the assembly depicted in FIG. 3a;

FIG. 33b is a magnified partial isometric view of the center portion of the base component depicted in FIG. 33a;

FIG. 33c is a partial cross-sectional view of a bottom portion of the base depicted in FIG. 33a;

FIG. 34a is an isometric view, having portions thereof removed, of the funnel component of the assembly depicted in FIG. 32;

FIG. 34b is a partial cross-sectional view of a bottom portion of the funnel depicted in FIG. 34a;

FIG. 34c is a partial cross-sectional view of a top portion of the funnel depicted in FIG. 34a;

FIG. 38c is a partial cross-sectional view of the pre-assembled components shown in FIG. 38a;

FIG. 39b is a partial cross-sectional view of a bottom portion of the funnel depicted in FIG. 39a;

FIG. 42b is a partial cross-sectional view of a bottom portion of the assembly depicted in FIG. 42a;

FIG. 43b is a cross-sectional view of the vacuum base depicted in FIG. 43a;

FIG. 44b is a partial cross-sectional view of the bottom portion of the assembly depicted in FIG. 44a;

FIG. 45a is an isometric view of the funnel used in the vacuum filtration apparatus depicted in FIG. 46a;

FIG. 46a is a cross-sectional view of a vacuum filtration apparatus using the funnel shown in FIG. 45a;

FIG. 54 is a partial cross-sectional view of the filtration apparatus shown in FIG. 53 showing details of the lid attached to the base with a tight seal between the lid and base;

FIG. 55 is a partial cross-sectional view of the filtration apparatus shown in FIG. 53 showing details of the lid loosely attached to the base;

DETAILED DESCRIPTION OF THE PRIOR ART

Figure 1A:
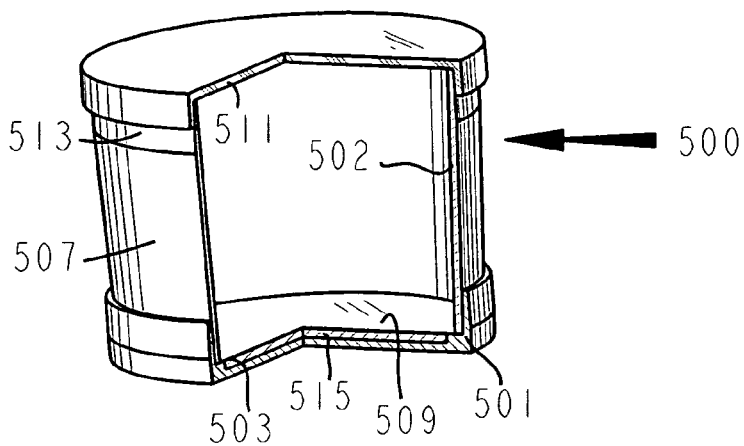
FIG. 1a is an isometric view, having portions thereof removed, of the assembled components that comprise the first embodiment of the prior art, with the components assembled as the user would receive them, ready for filtration.
Figure 1B:
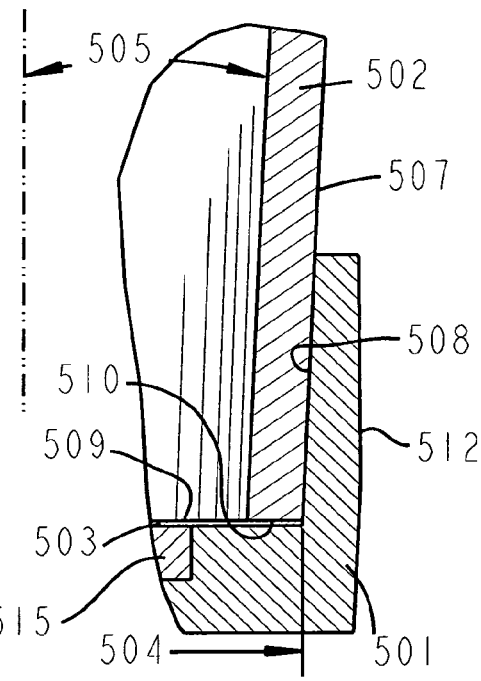
Figure 1C:
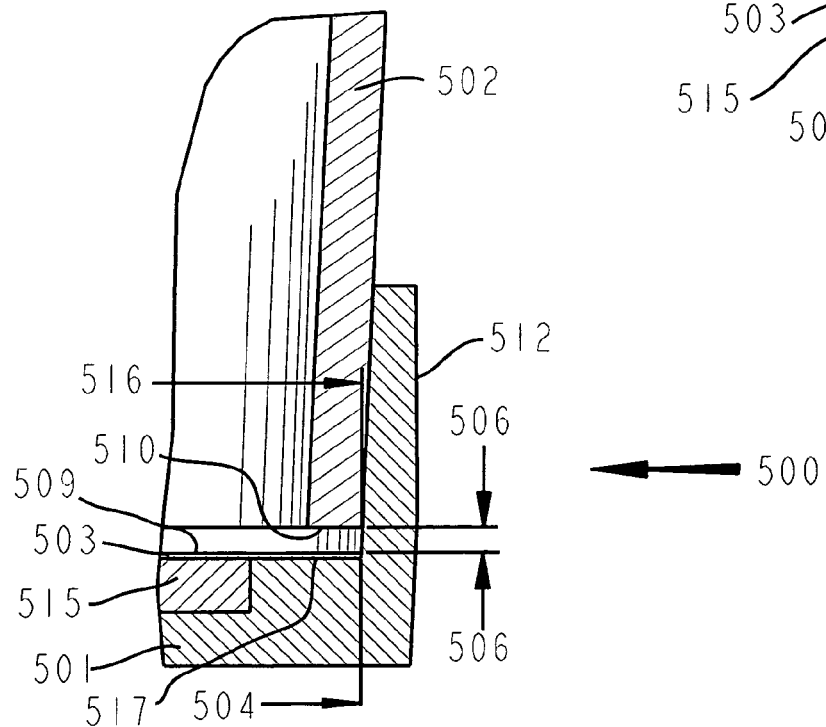
FIG. 1c is a partial cross-sectional view of a bottom portion of the assembly depicted in FIG. 1a, in which the component dimensions have changed from those shown in FIG. 1b.

FIG. 1a through FIG. 2b illustrate the first embodiment of the prior art. FIG. 1a is an isometric view, having portions thereof removed, of assembly 500 that contains the component parts of the first embodiment of the prior art. This assembly contains a base 501, a funnel 502, a lid 511, a microporous filter 503, and an absorbent pad 515. The outlet port and absorbent pad support structure of base 501 are not shown for simplicity. Funnel 502 is press fitted into base 501, and lid 511 is press fitted over funnel 502. Absorbent pad 515 is positioned in a well in base 501, with microporous filter 503 resting on top of absorbent pad 515, and with the outer periphery of microporous filter 503 compression sealed between the bottom face 510 of funnel 502 and seal surface 517 of base 501. FIG. 1b is a partial cross-sectional view of assembly 500 showing how funnel 502 is press fitted into base 501. Outer wall 507 of funnel 502 engages inner wall 508 of base 501. Referring to FIG. 1c, diameter 504 is the inside diameter of base 501 at the top face 509 of microporous filter 503, and diameter 516 is the outside diameter of funnel 502 at the bottom face 510 of funnel 502. Referring to FIG. 1b, diameter 516 equals diameter 504, and funnel 502 press fits into base 501 so that funnel 502 is press fitted to base 501 with sufficient force to prevent accidental disengagement, and so that the outer periphery of microporous filter 503 is sealed between the bottom face 510 of funnel 502 and seal surface 517 of base 501. FIG. 1c shows that if either the value of diameter 504 is reduced from that shown in FIG. 1b, or if the value of diameter 516 is increased from that shown in FIG. 1b, or if both conditions exist then funnel 502 will press fit into base 501 as shown in FIG. 1c with a gap existing between the bottom face 510 of funnel 502 and the top surface 509 of microporous filter 503. With the condition shown in FIG. 1c, the microporous filter 503 will not be sealed between the bottom face 510 of funnel 502 and the seal surface 517 of base 501, hence when a vacuum source is applied to the downstream side of absorbent pad 515 through an outlet port (not shown), liquid in the funnel will be drawn through microporous filter 503, and then through absorbent pad 515 into the vacuum source, and a portion of said liquid in funnel 502 may bypass around the outer edge of microporous filter 503, and then through absorbent pad 515 into the vacuum source. If microorganisms are contained in the liquid that bypasses microporous filter 503, these microorganisms will not be detected. If either the value of diameter 504 is increased from that shown in FIG. 1b, or if the value of diameter 516 is decreased from that shown in FIG. 1b, or if both conditions exist then a gap will exist between inner wall 508 of base 501 and outer wall 507 of funnel 502, and funnel 502 will not press fit into base 501, thus preventing funnel 502 from being assembled to base 501. Referring to FIG. 1b, the value of angle 505 (the draft angle of outer wall 507 of funnel 502, and the draft angle of inner wall 508 of base 501) is typically between 0.5° and 2.0°. Table 1 below shows how gap 506 will vary relative to draft angle 505, and relative to the dimension tolerance of the molded component parts (i.e. base 501, funnel 502, and lid 511). Because gap 506 is not dependent upon the actual value of diameter 504, or upon the actual value of diameter 516, these dimensions are represented by the symbolic value A, and a specific variation on the value of A. Typically the height of inner wall 508 of base 501 is less than 0.25", to keep the height of the petri dish to a minimum. It is reasonable to expect that parts molded in resins such as polypropylene or polyethylene or polystyrene, can be molded to dimension tolerances of ±0.003", and with difficulty ±0.002". The thickness of microporous filter 503 may vary from a minimum of 0.001" thick, to a maximum of about 0.012" thick, depending upon the type of microporous filter needed for the application.

TABLE 1

| Angle 505 | Dia. 504 | Dia. 516 | Gap 506 | Dimension Tolerance |
| --- | --- | --- | --- | --- |
| 0.5° | A | A | 0.000" | ±0.000" |
| 0.5° | A − 0.001" | A + 0.001" | 0.115" | ±0.001" |
| 0.5° | A − 0.002" | A + 0.002" | 0.229" | ±0.002" |
| 0.5° | A − 0.003" | A + 0.003" | 0.344" | ±0.003" |
| 1.0° | A | A | 0.000" | ±0.000" |
| 1.0° | A − 0.001" | A + 0.001" | 0.057" | ±0.001" |
| 1.0° | A − 0.002" | A + 0.002" | 0.115" | ±0.002" |
| 1.0° | A − 0.003" | A + 0.003" | 0.172" | ±0.003" |
| 2.0° | A | A | 0.000" | ±0.000" |
| 2.0° | A − 0.001" | A + 0.001" | 0.029 | ±0.001" |
| 2.0° | A − 0.002" | A + 0.002" | 0.057" | ±0.002" |
| 2.0° | A − 0.003" | A + 0.003" | 0.086" | ±0.003" |

Referring to Table 1, it can be seen that dimension tolerances of ±0.001" are not good enough to guarantee that the microporous filter will be sealed between bottom face 510 of funnel 502, and seal surface 517 of base 501. As explained above it is not practical to mold parts to a dimension tolerance of ±0.001", or better.

Figure 2A:
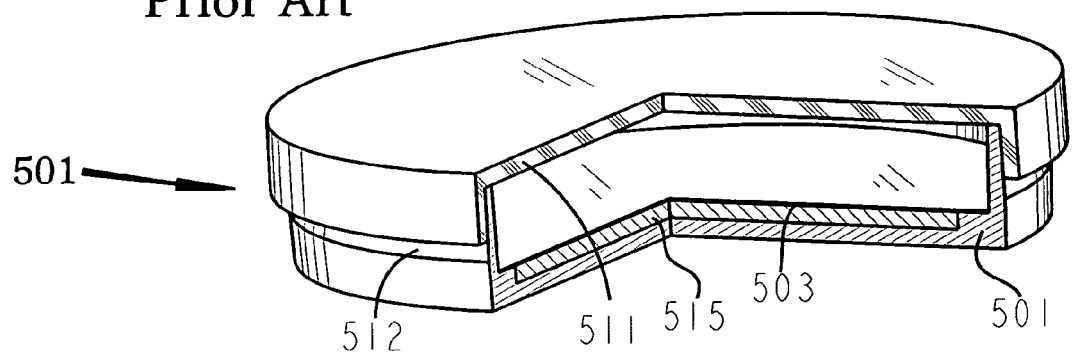
FIG. 2a is an isometric view, having portions thereof removed, of the assembled components that comprise the first embodiment of the prior art, without the funnel section, with the remaining components assembled in the petri dish mode.
Figure 2B:
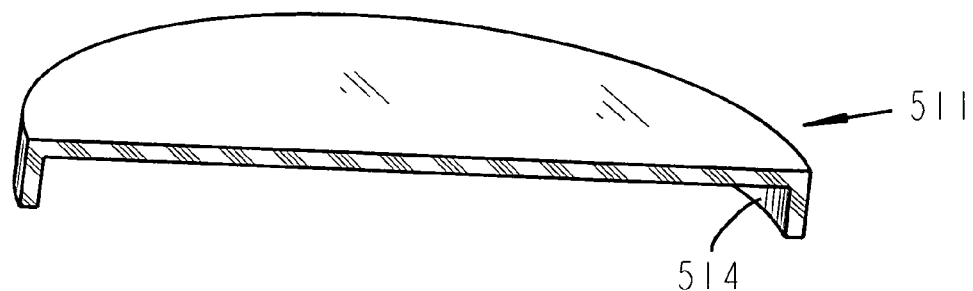

Referring to FIG. 1a, FIG. 2a, and FIG. 2b, Lid 511 is press fitted onto the top of funnel 502 so that inner wall 514 of lid 511 engages outer wall 513 of funnel 502. Lid 511 should fit onto funnel 502 tightly enough so that it will not come loose, but not so tight as to make it difficult for the user to remove lid 511 from funnel 502 with one hand. The draft angle of outer wall 513 of funnel 502, and the draft angle of inner wall 514 of lid 511 is typically between 0.5° and 2.0°. The above analysis of the fit between outer wall 507 of funnel 502, and inner wall 508 of base 501 applies to the fit between outer wall 513 of funnel 502 and inner wall 514 of lid 511.

FIG. 2a shows assembly 501, with funnel 502 discarded, and with lid 511 press fitted onto base 501 to form a petri dish. Referring to FIG. 2a and FIG. 2b, lid 511 is press fitted onto the top of base 501 so that inner wall 514 of lid 511 engages outer wall 512 of base 501. Lid 511 should fit onto base 501 tightly enough so that it will not come loose when inverted, but not so tight as to make it difficult for the user to remove lid 511 from base 501 with one hand. The draft angle of outer wall 512 of base 501, and the draft angle of inner wall 514 of lid 511 is typically between 0.5° and 2.0°. The above analysis of the fit between outer wall 507 of funnel 502, and inner wall 508 of base 501 applies to the fit between outer wall 512 of base 501 and inner wall 514 of lid 511.

From the above analysis it can be seen that because the component parts that comprise assembly 500, and assembly 501, can not be molded to a high enough dimensional tolerance to be able to fit any funnel 502, to any base 501, or to fit any lid 511 to any funnel 502, or to fit any lid 511 to any base 501, it is necessary to match individual parts to make an assembly. This increases production costs, because of the time required to match parts, and because of the large amount of parts that have to be scrapped because they can not be matched. In addition, when a funnel is matched to a base to get a good press fit between outer wall 507 of funnel 502 and inner wall 508 of base 501, a gap 506 may exist between the bottom face 510 of funnel 502 and the top surface 509 of microporous filter 503, so that microporous filter 503 will not be sealed between bottom face 510 of funnel 502 and seal surface 517 of base 501, thus allowing bypass around microporous filter 503 during the filtration process.

FIG. 3a, FIG. 3b, FIG. 3c and FIG. 3d, depict a second embodiment of the prior art. Assembly 600 contains base 601, funnel 602, lid 611, microporous filter 603, and absorbent pad 615. Lid 611 press fits onto funnel 602 in the same manner described above for lid 511 press fitting onto funnel 502, hence this press fit has the same drawbacks described above. After filtration is complete, funnel 602 is discarded, and lid 611 is press fitted to base 601 to form a petri dish, in the same manner described above for lid 511 press fitting onto base 501, hence this press fit has the same drawbacks described above. Funnel 602 snap fits into base 601, with bead 621 of funnel 602 fitting into groove 626 of base 601. When funnel 602 is properly snap fitted to base 601, microporous filter 603, and absorbent pad 615, are compressed between bottom face 610 of funnel 602, and seal surface 628 of base 601. With this design base 601, and funnel 602 are molded from a pliable material such as polyethylene, or polypropylene.

Figure 3A:
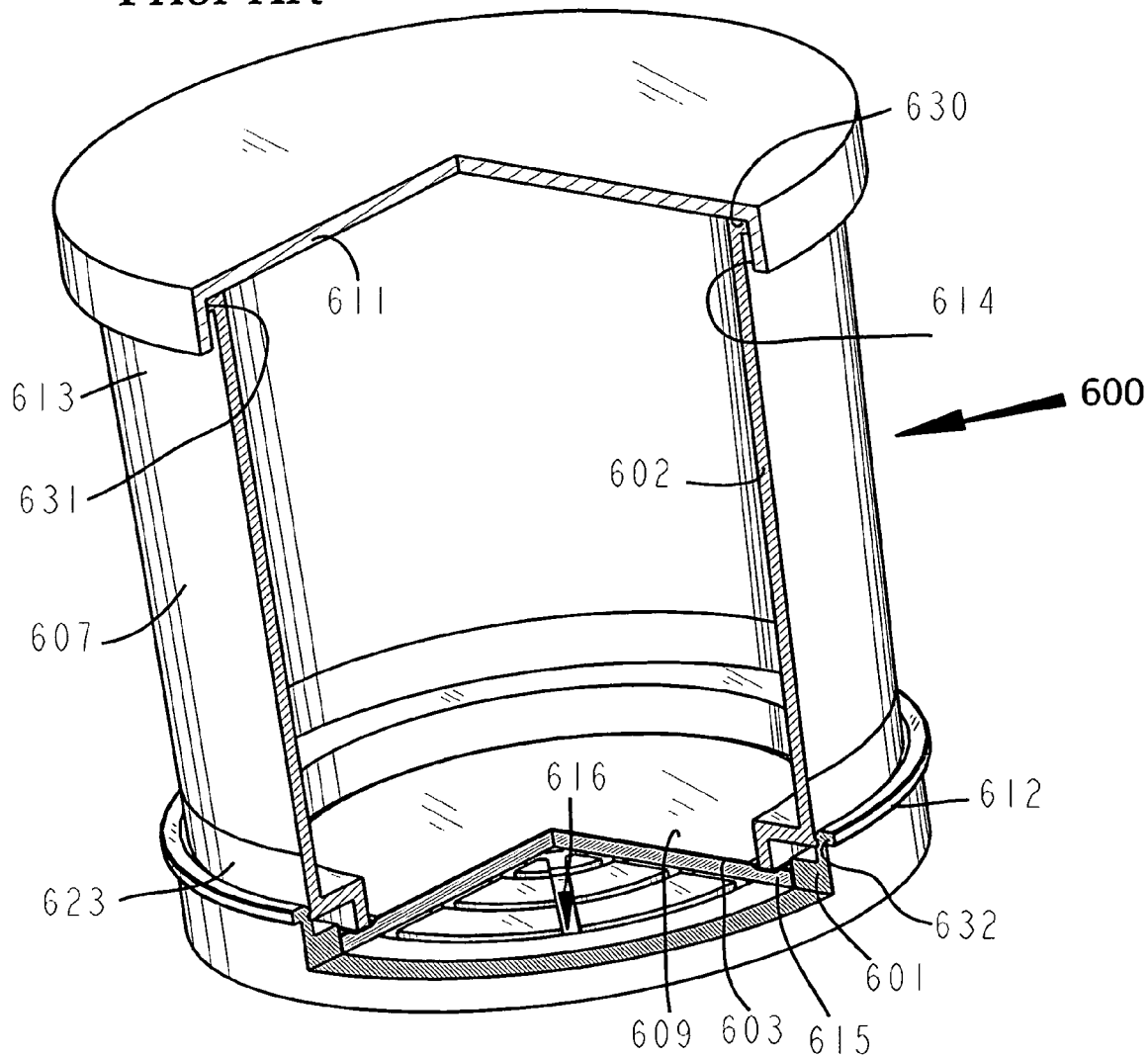
FIG. 3a is an isometric view, having portions thereof removed, of the assembled components that comprise the second embodiment of the prior art, with the components assembled as the user would receive them, ready for filtration.
Figure 3B:
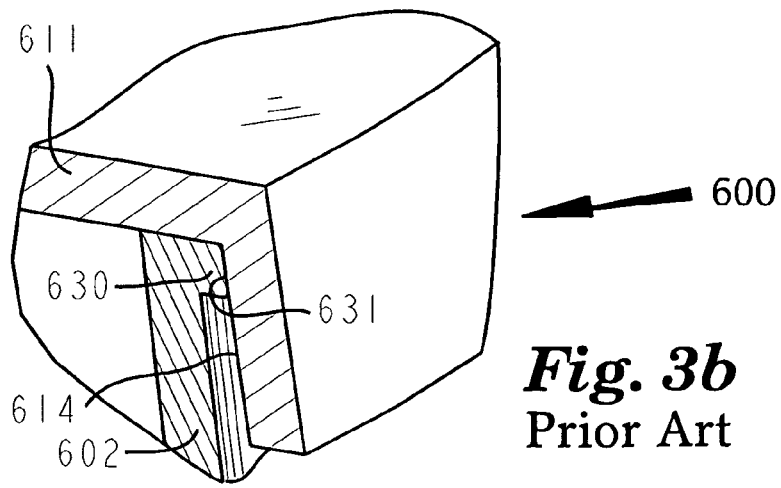
Figure 3C:
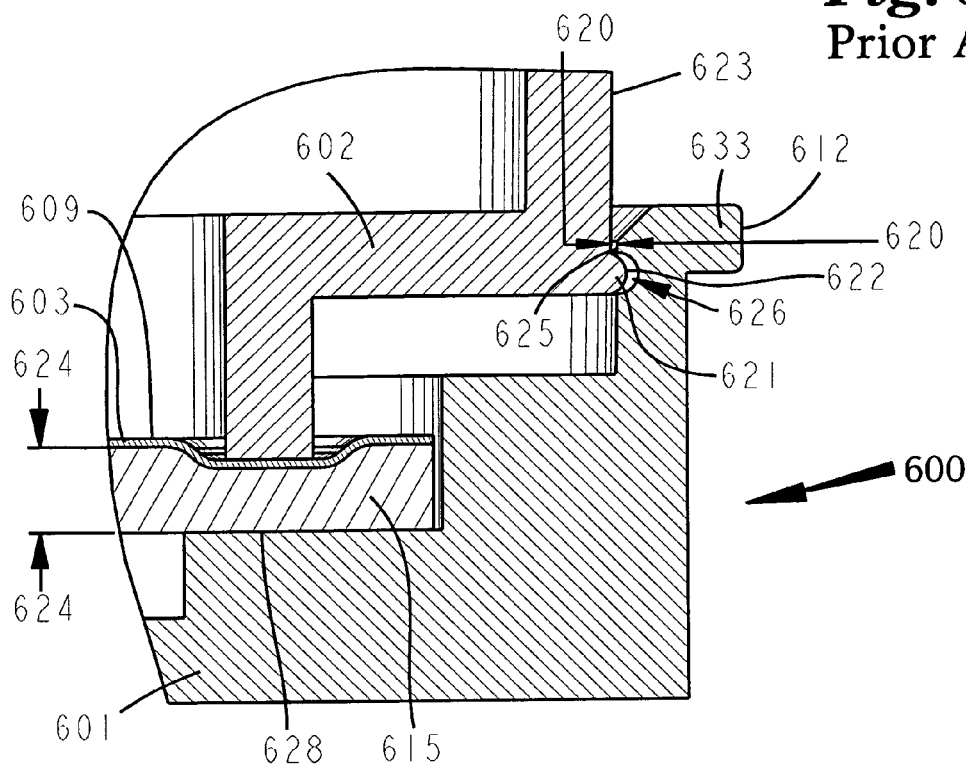
Figure 3D:
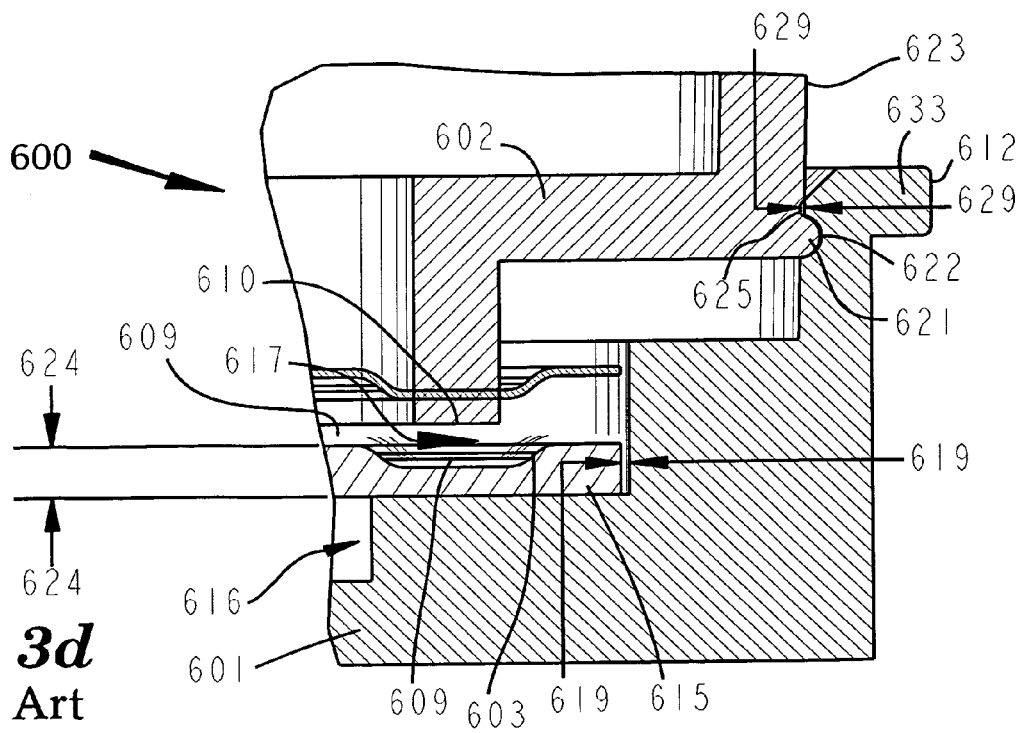
FIG. 3d is a partial cross-sectional view of a bottom portion of the assembly depicted in FIG. 3a, in which the component dimensions have changed from those shown in FIG. 3c, and in which the microporous filter and the absorbent pad are shown compressed because of a negative pressure being applied to the downstream side of the absorbent pad.

Referring to FIG. 3c, if outer wall 623 of funnel 602 is smaller in diameter than inner wall 625 of base 601, to create gap 620, then the snap fit will be loose. If gap 620 is large enough, then funnel 602 will not snap fit into base 601, and thus funnel 602 will not be held in place by base 601. Referring to FIG. 3d, if outer wall 623 of funnel 602 is larger in diameter than inner wall 625 of base 601, to create overlap 629, then inner wall 625 of base 601 will stretch, (provided that the overlap is not to great) and the snap fit will fit properly.

Although the snap fit shown in FIG. 3a, FIG. 3c, and FIG. 3d, provides for a greater value of dimension tolerance between funnel 602, and base 601, than the press fit described above for assembly 500, in production, with parts molded to a dimensional tolerance of ±0.003", it may be necessary to match funnels to bases.

Referring to FIGS. 3a and 3b, lid 611 is press fitted onto the top of funnel 602 so that inner wall 614 of lid 611 engages outer wall 631 of funnel seal ring 630. Lid 611 should fit onto funnel 602 tightly enough so that it will not come loose, but not so tight as to make it difficult for the user to remove lid 611 from funnel 602 with one hand. Lid 611 is normally molded from a rigid material such as polystyrene, and funnel 602 is normally molded from a more pliable material such as polypropylene. If lid 611, and funnel 602 are both molded with dimension tolerances of ±0.003", and if under nominal conditions lid 611 press fits onto funnel 602 with 0.001" of interference between inner wall 614 of lid 611, and outer wall 631 of funnel seal ring 630; then if the diameter of inner wall 614 of lid 611 is molded to its maximum dimension of nominal plus 0.003", and if the diameter of outer wall 631 of funnel seal ring 630 is molded to its minimum dimension of nominal minus 0.003", then lid 611 will not press fit onto funnel 602, instead there will be 0.005" of slop between inner wall 614 of lid 611 and outer wall 631 of funnel seal ring 630, and lid 611 will fall off of funnel 602 if assembly 600 is accidentally tipped on its side. On the other hand if the diameter of inner wall 614 of lid 611 is molded to its minimum dimension of nominal minus 0.003", and if the diameter of outer wall 631 of funnel seal ring 630 is molded to its maximum dimension of nominal plus 0.003", then lid 611 will press fit onto funnel 602 with 0.007" of interference between inner wall 614 of lid 611, and outer wall 631 of funnel seal ring 630. With this much interference it will not be possible to easily position lid 611 onto funnel 602 with one handed operation, nor will it be easy to remove lid 611 from funnel 602 with one handed operation.

When filtration is complete, funnel 602 will be discarded, and lid 611 will be press fitted onto base 601 with inner wall 614 of lid 611 engaging outer wall 612 of base seal ring 632, to form a petri dish like the one shown in FIG. 2a. Lid 611 is normally molded from a rigid material such as polystyrene, and base 601 is normally molded from a more pliable material such as polypropylene. If lid 611, and base 601 are both molded with dimension tolerances of ±0.003", and if under nominal conditions lid 611 press fits onto base 601 with 0.001" of interference between inner wall 614 of lid 611, and outer wall 612 of base seal ring 632; then if the diameter of inner wall 614 of lid 611 is molded to its maximum dimension of nominal plus 0.003", and if the diameter of outer wall 612 of base seal ring 632 is molded to its minimum dimension of nominal minus 0.003", then lid 611 will not press fit onto base 601, instead there will be 0.005" of slop between inner wall 614 of lid 611 and outer wall 612 of base seal ring 632, and lid 611 will fall off of base 601 when the petri dish is inverted for incubation. On the other hand if the diameter of inner wall 614 of lid 611 is molded to its minimum dimension of nominal minus 0.003", and if the diameter of outer wall 612 of base seal ring 632 is molded to its maximum dimension of nominal plus 0.003", then lid 611 will press fit onto base 602 with 0.007" of interference between inner wall 614 of lid 611, and outer wall 612 of base seal ring 632. With this much interference it will not be possible to easily position lid 611 onto base 601 with one handed operation, nor will it be easy to remove lid 611 from base 601 with one handed operation.

Referring to FIG. 3a, FIG. 3c, and FIG. 3d, microporous filter 603 and absorbent pad 615 are compressed between bottom face 610 of funnel 602, and seal surface 628 of base 601, as shown in FIG. 3c. During the filtration mode the interior of funnel 602 will contain the liquid to be filtered, with the space above the liquid being at atmospheric pressure. Either lid 611, or funnel 602 contain a venting means (not shown) to maintain the space in funnel 602 above the liquid at atmospheric pressure during the filtration process. This liquid will wet the pores of the microporous filter (i.e. a hydrophilic filter). Filter underdrain 616 is in fluid flow communication with the base outlet port (not shown). When a negative pressure (i.e. vacuum) is applied to the outlet port, and therefore to filter underdrain 616, the pressure on the upstream side of microporous filter 603 will be atmospheric plus the pressure head of the liquid above microporous filter 603, and the pressure below the absorbent pad 615 will be the negative pressure of the vacuum source. Microporous filter 603 will have a pore size of between 0.2 µm, and 1.0 µm, and absorbent pad 615 will have a very large pore size compared to the pore size of microporous filter 603. Therefore, most of the pressure drop (i.e. the difference between the positive pressure on the upstream side of microporous filter 603, and the negative pressure on the downstream side of absorbent pad 615) will occur across microporous filter 603. The pressure drop across microporous filter 603 will be in the approximate range of 10 pounds per square inch, to 14 pounds per square inch. Absorbent pad 615 is made of a material that is easy to compress. Therefore, the force that is applied to the top of microporous filter 603 (by the differential pressure applied across microporous filter 603), will compress absorbent pad 615, as shown in FIG. 3d, and liquid will pass (as shown by arrow 617) through the gap between bottom face 610 of funnel 602, and top face 609 of microporous filter 603, and then into gap 619, through or around absorbent pad 615, and then into the vacuum source, thus bypassing microporous filter 603. If the liquid that bypasses microporous filter 603 contains microorganisms, these microorganisms will not be trapped on the upstream side of microporous filter 603. Therefore these microorganisms will not be detected.

DETAILED DESCRIPTION OF THE PREFERRED EMBODIMENTS

Although various embodiments of the filtration apparatus constructed in accordance with the present invention are disclosed herein, each embodiment enables the filtration apparatus to be made from component parts that have been molded within a dimensional tolerance range of 0.004", and most embodiments provides an integral compression seal of the filter means, for filter means of varying thickness, and each embodiment provides a means to heat seal or otherwise seal the filter means with a non-releasable seal to the base.

Figure 4:
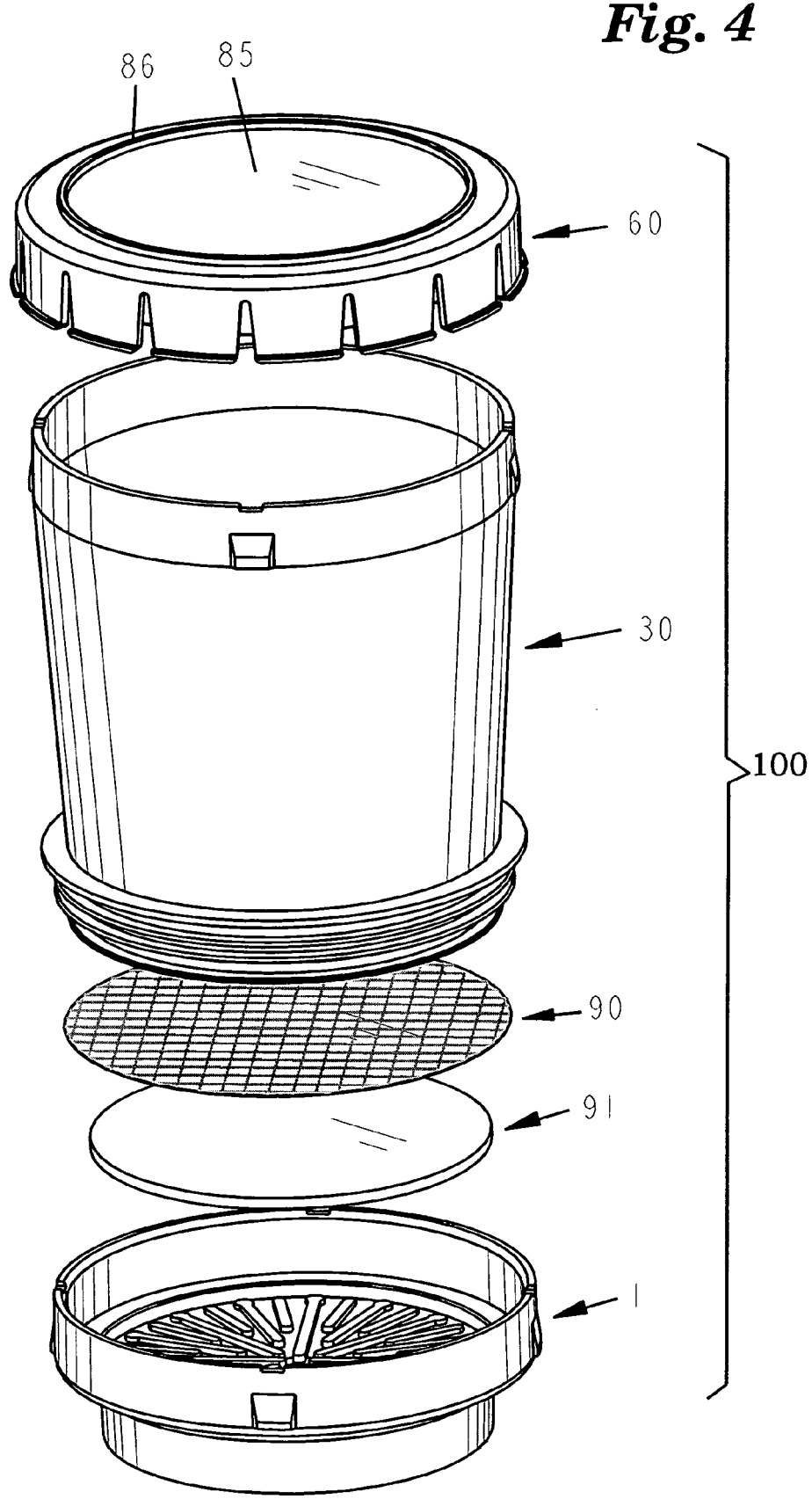
FIG. 4 is an exploded isometric view of the components that comprise the first embodiment of the filtration apparatus, constructed in accordance with the principles of the present invention, usable for detecting microorganisms and particulates in liquid samples.
Figure 5:
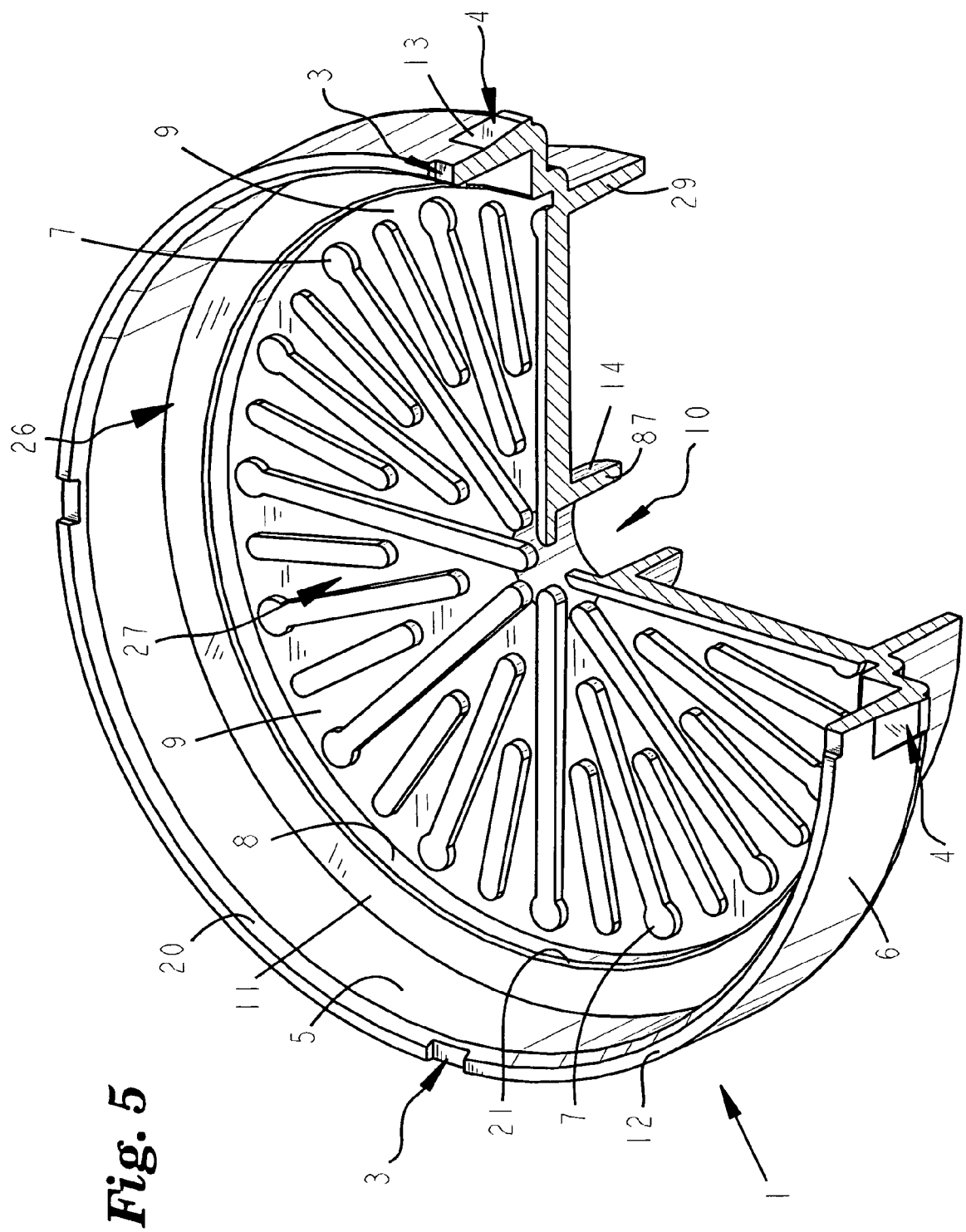
FIG. 5 is an isometric view, having portions thereof removed, of the base component of the assembly depicted in FIG. 4.
Figure 7:
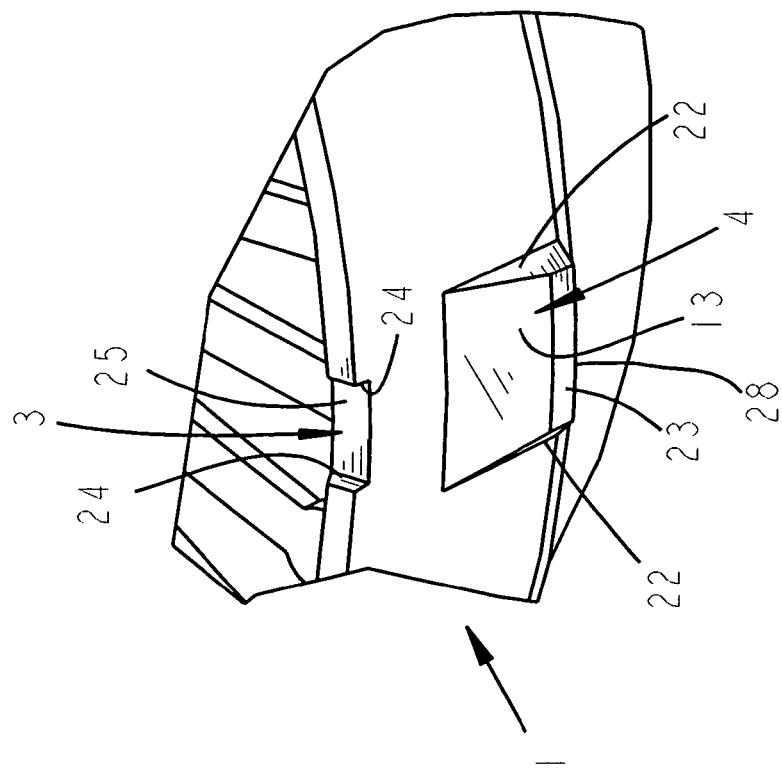
FIG. 7 is a magnified partial isometric view of the base component of the assembly depicted in FIG. 4, showing a venting means and a means for clamping the lid to the base.
Figure 6:
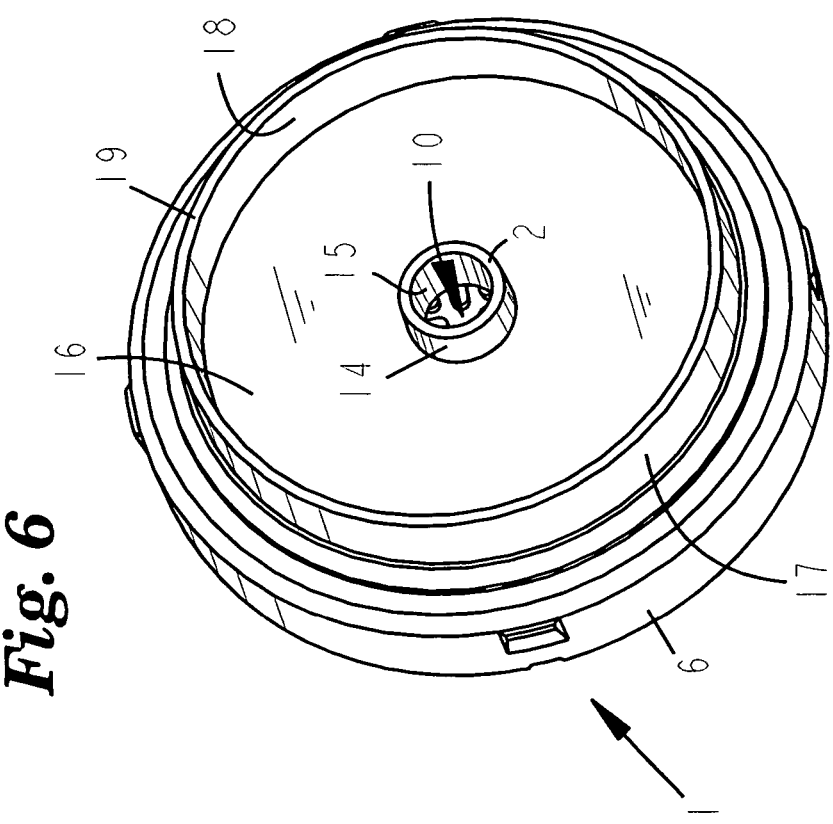
FIG. 6 is a bottom isometric view of the base component of the assembly depicted in FIG. 4.

One embodiment of the filtration apparatus constructed in accordance with the principles of the present invention, is shown in FIGS. 4 through FIG. 15b. Referring to FIG. 4, exploded assembly 100 contains, base 1, absorbent pad 91 (for most applications the absorbent pad is preferably made from a hydrophilic material such as cellulose fibers), filter means 90 (preferably a microporous filter and for most applications more preferably a hydrophilic microporous filter), funnel 30, and lid 60. Referring to FIG. 5, FIG. 6, and FIG. 7, base 1 contains funnel well 26, bounded by filter seal surface 11, and inside wall 5. Inside wall 5 contains chamfer 20. Base 1 also contains pad well 27 disposed in the bottom of the funnel well, bounded by lower inside wall 8, and bottom inside surface 9. The common edge between filter seal surface 11 and lower inside wall 8, may contain round 21. Base 1 contains outlet port 10. Bottom inside surface 9 may slope downward from its outside periphery toward outlet port 10. Outlet port 10 is in fluid flow communication with pad well 27. Base 1 also contains a means to support absorbent pad 91, shown here by pad support ribs 7, which protrude upward from bottom inside surface 9. The top surface of pad support ribs 7 preferably lie in a horizontal plane, said plane being located below filter seal surface 11, a distance approximately equal to the thickness of absorbent pad 91. Although pad support ribs 7 are shown as radial ribs, any filter support structure that provides sufficient support to absorbent pad 91, and that provides the proper drainage of filtered liquid from pad well 27 to outlet port 10 may be used. Top outer wall 12 of base 1 contains one or more vent slots 3, bounded by side walls 24, and bottom wall 25. Outside wall 6 of base 1 contains one or more lid clamp tabs 4, that protrude from outside wall 6. Each lid clamp tab 4 is bounded by side walls 22, bottom wall 28, sloped surface 13, and outer surface 23. Sloped surface 13 may terminate at bottom wall 28, thus eliminating outer surface 23. The one or more lid clamp tabs 4 should be positioned so that the bottom edge of each lid clamp tab is equidistant from top outer wall 12 of base 1. Base 1 also contains support ring 29, which protrudes from bottom outside wall 16, and is bounded by inner side surface 18, outer side surface 17, and bottom surface 19. Support ring 29 supports base 1 when base 1 is placed on a flat surface. Outlet tube 87 protrudes from bottom outside wall 16, and is bound by outlet tube outside surface 14, outlet tube inside surface 15, and outlet tube bottom surface 2. Outlet port 10 is bound by outlet tube inside surface 15. Outlet port 10 is in fluid flow communication with pad well 27.

Figure 8:
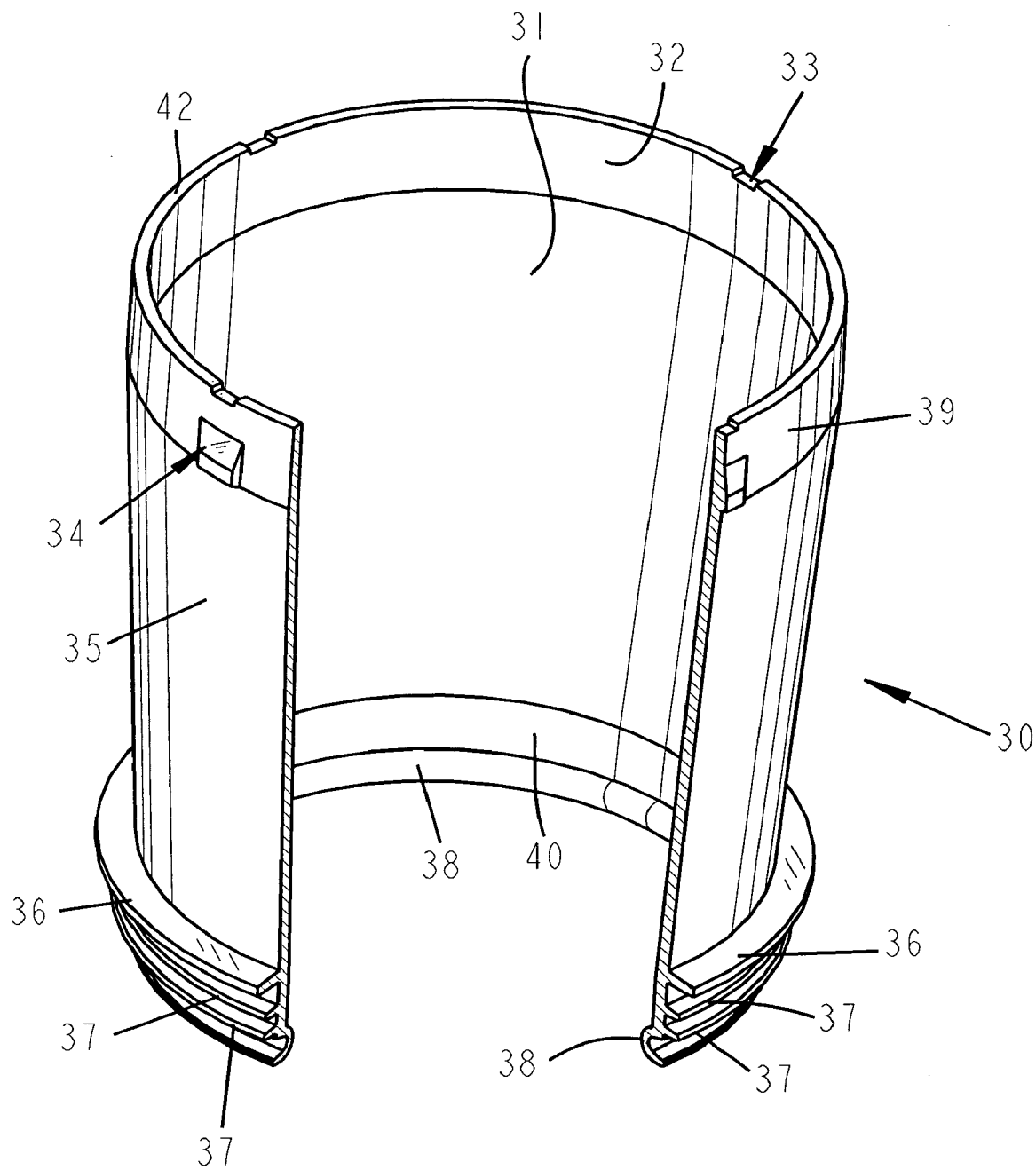
FIG. 8 is an isometric view, having portions thereof removed, of the funnel component of the assembly depicted in FIG. 4.
Figure 9:
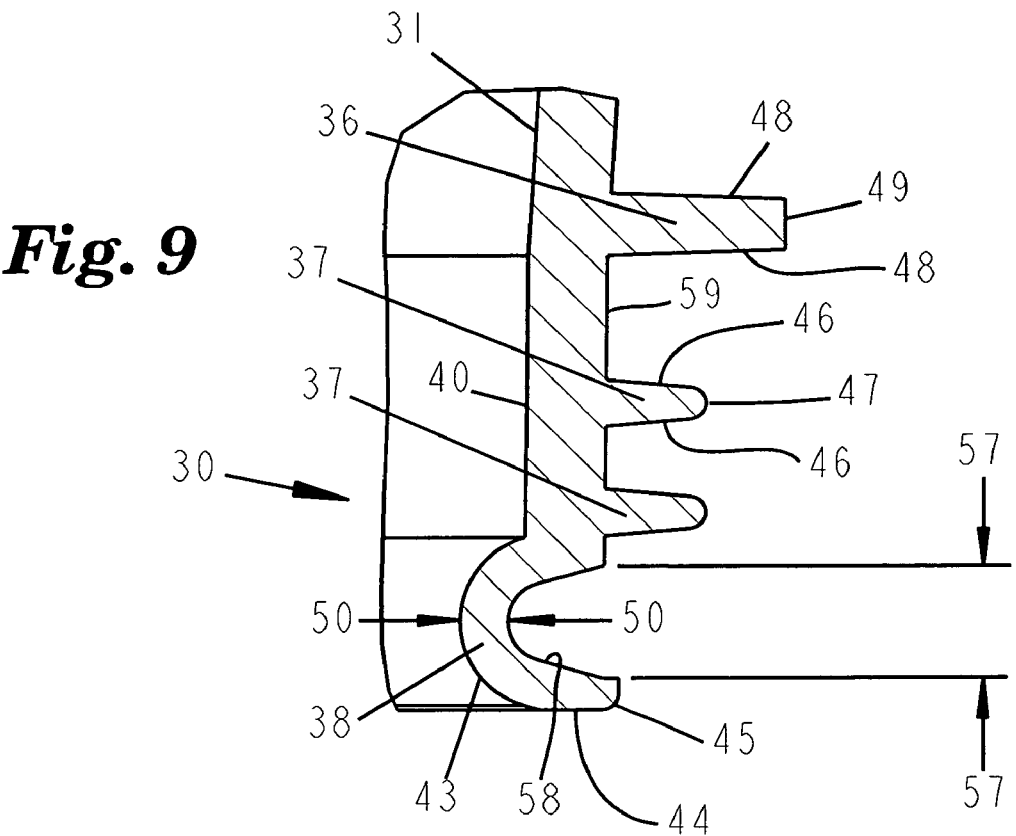
FIG. 9 is a partial cross-sectional view of a bottom portion of the funnel depicted in FIG. 8.
Figure 10:
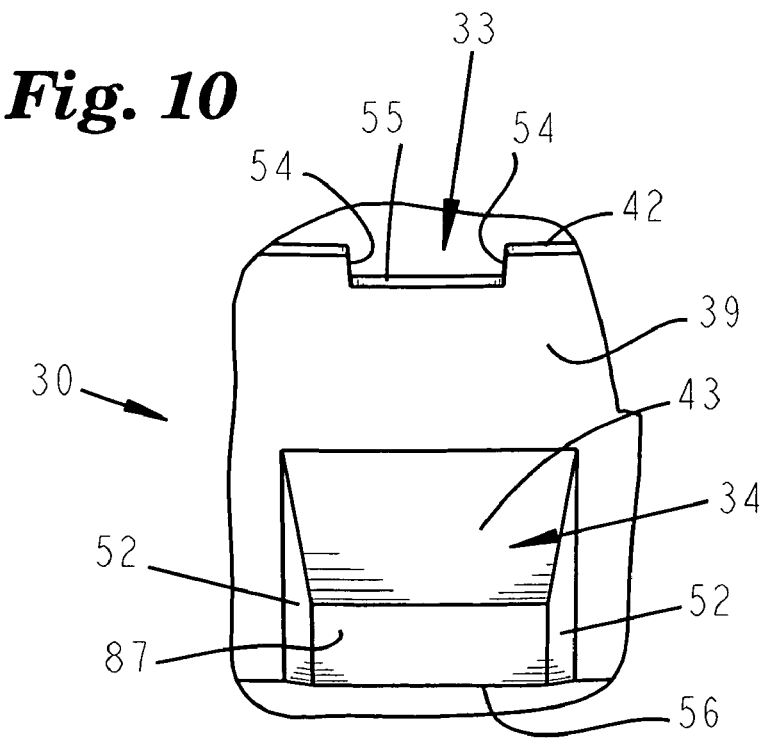
FIG. 10 is a magnified partial isometric view of the funnel component depicted in FIG. 8, showing a venting means and a means for clamping the lid to the funnel.
Figure 28:
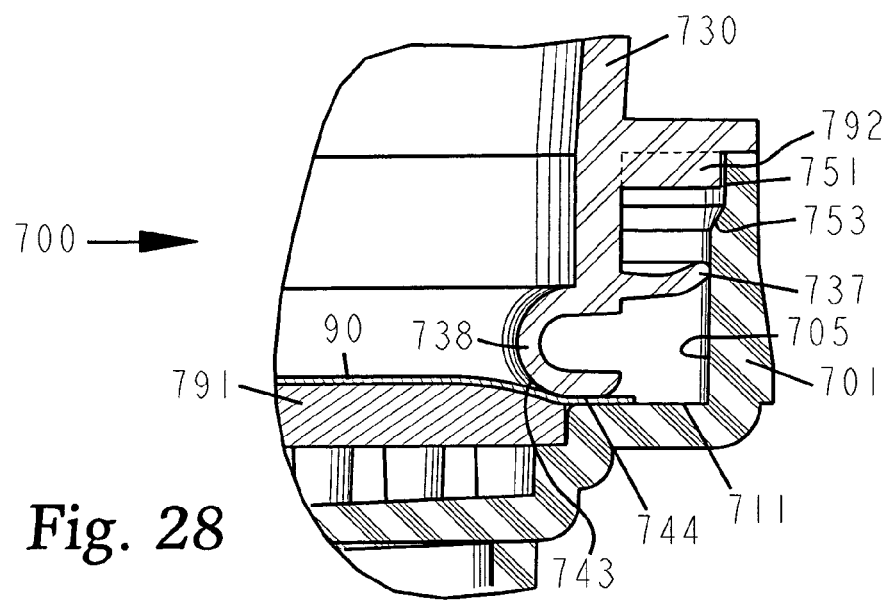
FIG. 28 is a partial cross-sectional view of the bottom portion of the assembly shown in FIG. 27.
Figure 29:
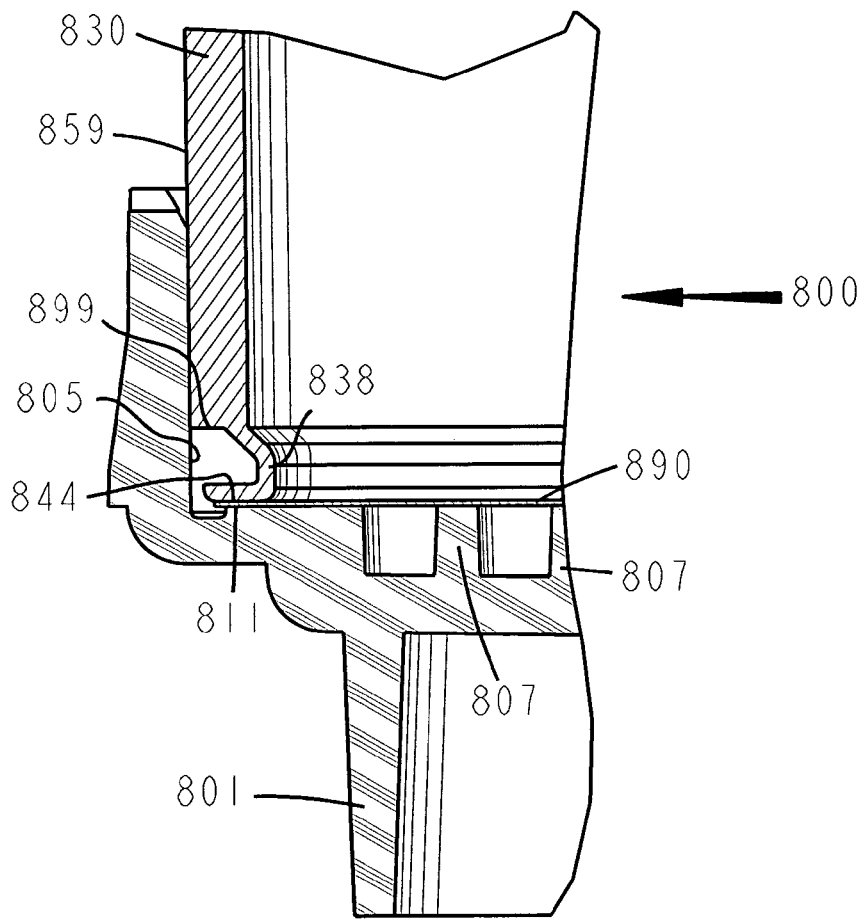
FIG. 29 is a partial cross-sectional view of the bottom portion of the assembly that comprise the seventh embodiment of the filtration apparatus, constructed in accordance with the principles of the present invention, usable for detecting microorganisms and particulates in liquid samples.
Figure 30:
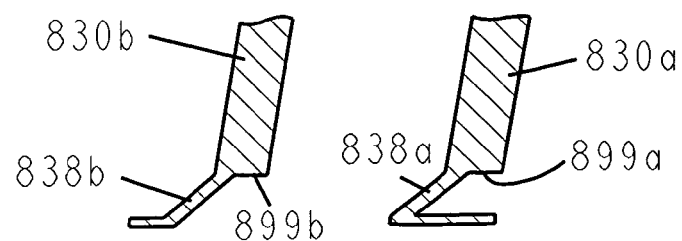
FIG. 30 shows a partial bottom cross-section of two funnels detailing different versions of a integral flexible filter seal.

Details of funnel 30 are shown in FIG. 8, FIG. 9, and FIG. 10. The bottom of funnel 30 contains an integral flexible filter seal 38, disposed around the bottom of funnel 30, bound by inner surface 43, outer surface 58, and bottom surface 44. Inner surface 43 is preferably formed by revolving a round section around the central axis of funnel 30, with the top of said round attached to the bottom inside edge of inner wall 40 of funnel 30 as depicted in FIG. 9. Bottom surface 44 is preferably flat and contains round 45 at its outside edge as depicted in FIG. 9. Outer surface 58 is a C-shaped surface as depicted in FIG. 9. Although integral flexible filter seal 38 as shown in FIG. 9 is C-shaped with the open part of the C pointing outward, any shape that allows the seal to compensate for varying filter thickness by flexing could be used, such as a C-shaped integral flexible filter seal with the open part of the C pointing inward, or the types of integral flexible filter seals shown in FIG. 29 as integral flexible filter seal 838, and in FIG. 30 as integral flexible filter seal 838a or as integral flexible filter seal 838b. All of the integral flexible filter seals shown in the FIG. 9, FIG. 13a, FIG. 13b, FIG. 16, FIG. 17a, FIG. 20, FIG. 21, FIG. 23, FIG. 28, FIG. 29, and FIG. 30 protrude from the bottom surface of the funnel. The bottom surface of the funnel is shown in FIG. 29 as bottom surface 899 of funnel 830, and it is shown in FIG. 30 as bottom surface 899a of funnel 830a, and as bottom surface 899b of funnel 830b. The integral flexible filter seal could however, protrude from the inner wall of the funnel, or from the outer wall of the funnel. The important feature of the integral flexible filter seal is that can flex to maintain a leak tight seal between a portion of the integral flexible filter seal and the filter seal surface of the base, for varying thickness' of the filter means, and/or for dimension variations of either the funnel or the base, or both. Although integral flexible filter seal 38 shown in FIG. 9 is composed of the same material as the rest of the funnel, the funnel could be molded of a first material such as polystyrene in a first molding cycle, and then the integral flexible filter seal 38 could be molded from a second much softer non-elastomeric material such as polyethylene, polypropylene, or from an elastomeric material such as rubber in a second molding cycle. The section of funnel 30 directly above integral flexible filter seal 38 is bound by inner wall 40, and outer wall 59. Inner wall 40 is preferably conical in shape with a draft angle of approximately ½°, to assist in removal from the mold from which it is molded. However the draft angle could be eliminated, so that the draft angle could be any angle greater than or equal to zero. Outer wall 59 may have the same draft angle as inner wall 40, or it may be vertical. Protruding from outer wall 59 is one or more integral flexible funnel seal rings 37. Each integral flexible funnel seal ring is bounded by side walls 46, and end wall 47. Side walls 46 are preferably tapered to improve moldability, and end wall 47 is preferably round in shape as depicted in FIG. 9. Although one or more integral flexible funnel seal rings 37 are shown in FIG. 9 as being composed of the same material as the rest of the funnel, the funnel could be molded of a first material such as polystyrene in a first molding cycle, and then the one or more integral flexible funnel seal rings 37 could be molded from a second much softer non-elastomeric material such as polyethylene, polypropylene, or from an elastomeric material such as rubber in a second molding cycle. The next section of funnel 30 is conical in shape and is bound by inner wall 31, and outer wall 35. The draft angle of outer wall 35, preferably matches that of inner wall 31 to maintain a uniform wall thickness, with the draft angle of both walls being greater than or equal to 0°. Funnel stop 36 protrudes from outer wall 35 and is bound by side walls 48, and end wall 49. Side walls 48 are preferably tapered to improve moldability. The top section of funnel 30 is bounded by inner wall 32, outer wall 39, and top wall 42. Inner wall 32 is conical in shape and preferably has a draft angle of ½ ° or less. The draft angle of outer wall 39 is preferably the same as the draft angle of outside wall 6 of base 1. Outer wall 39 and outer wall 35 could have the same draft angle in which case outer wall 35 would terminate at top wall 42. Referring to FIG. 8 and FIG. 10, top wall 42 may contain one or more vent slots 33, bounded by side walls 54, and bottom wall 55. Outer wall 39 of funnel 30 contains one or more lid clamp tabs 34, that protrude from outer wall 39. Each lid clamp tab 34 is bounded by side walls 52, bottom wall 56, sloped surface 43, and outer surface 87. Sloped surface 43 may terminate at bottom wall 56, thus eliminating outer surface 87. The outside diameter of outer surface 87 of the one or more lid clamp tabs of funnel 30 should equal the outside diameter of outer surface 23 of the one or more lid clamp tabs of base 1. The one or more lid clamp tabs 34 should be positioned so that the bottom edge of each lid clamp tab is equidistant from top wall 42 of funnel 30. The lid clamp tab could also be in the form of an annular ring.

Figure 11:
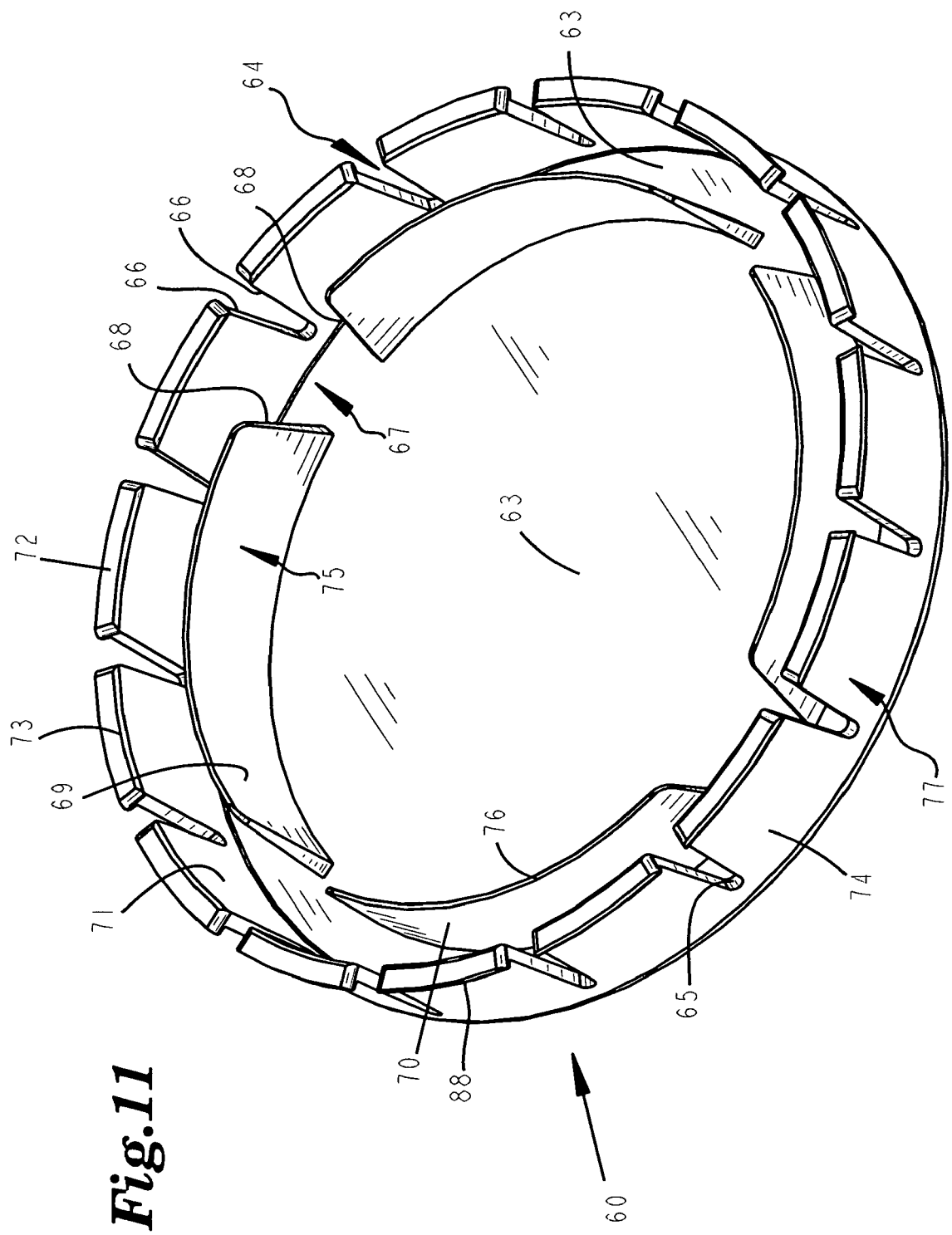
FIG. 11 is a bottom isometric view, of the lid component of the assembly depicted in FIG. 4.
Figure 12:
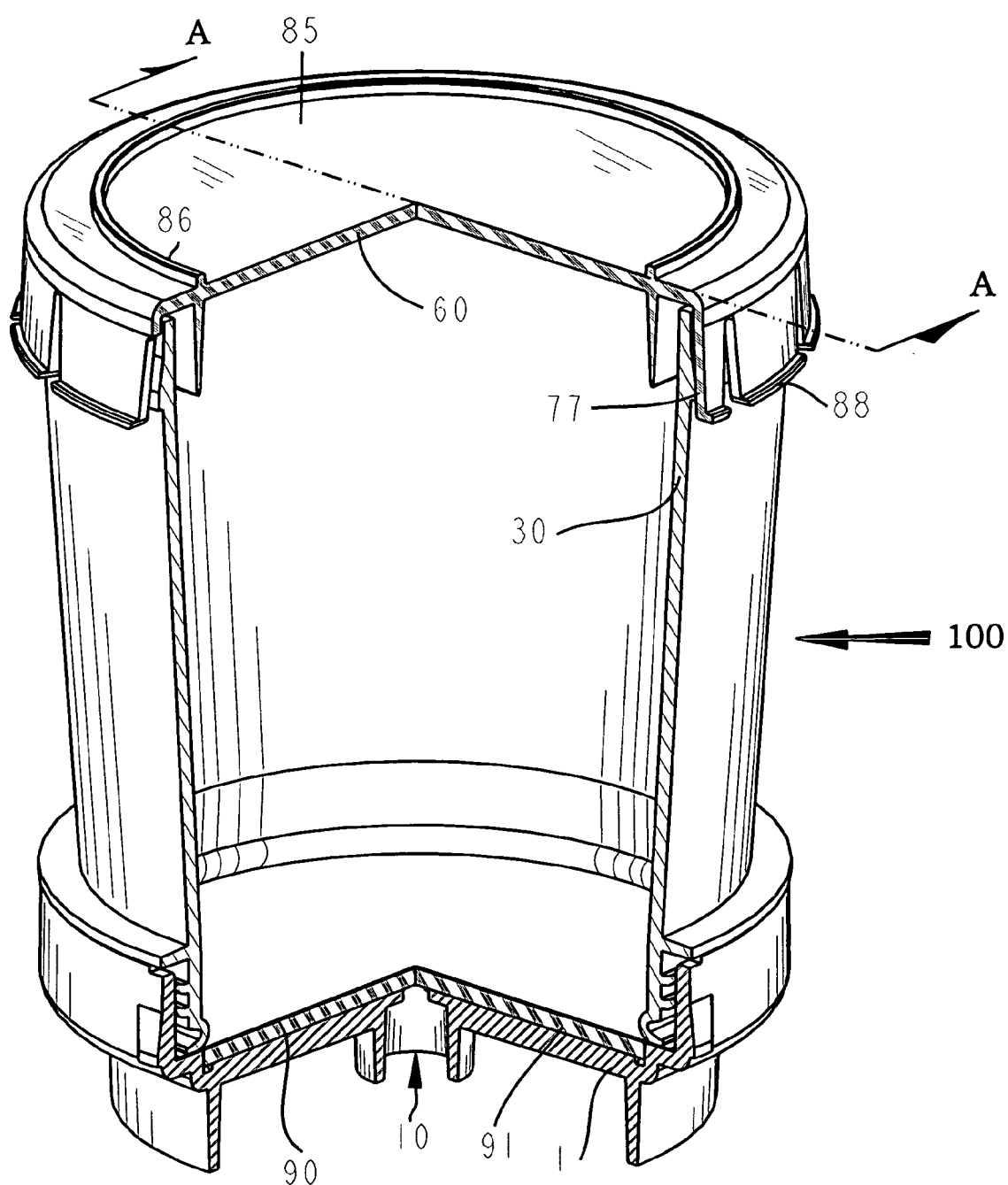
FIG. 12 is an isometric view, having portions thereof removed, of the assembled components that comprise the first embodiment of the filtration apparatus, constructed in accordance with the principles of the present invention, usable for detecting microorganisms and particulates in liquid samples.

Lid 60 is depicted in FIG. 11 and FIG. 12. Lid 60 contains outer wall 77, bounded by outer surface 74, inner surface 71, and bottom surface 72. The draft angle of inner surface 71, and outer surface 74, are preferably the same as the draft angle of outer wall 39 of funnel 30, and the draft angle of outside wall 6 of base 1. Bottom surface 72 may be extended beyond outer surface 74 to form lip 88. Outer wall 77 contains a plurality of slots 64, each slot 64 is bounded by side surfaces 66, and top surface 65. Each slot creates a gap in bottom surface 72 of lid 60. The top surface 65 of slots 64 is preferably offset from inside top surface 63. Filter hold down ring 75 protrudes from inside top surface 63 and is bounded by inner surface 69, outer surface 70, and bottom surface 76. Filter hold down ring 75 may contain one or more slots 67. Nest ring 86 protrudes from outer flat surface 85. The inside diameter of nest ring 86 should be slightly larger than the outside diameter of outer side surface 17, of support ring 29 of base 1, so that the bottom of support ring 29 of base 1 can be nested inside nest ring 86 of lid 60, to enable devices to be stacked on top of each other.

Figure 13A:
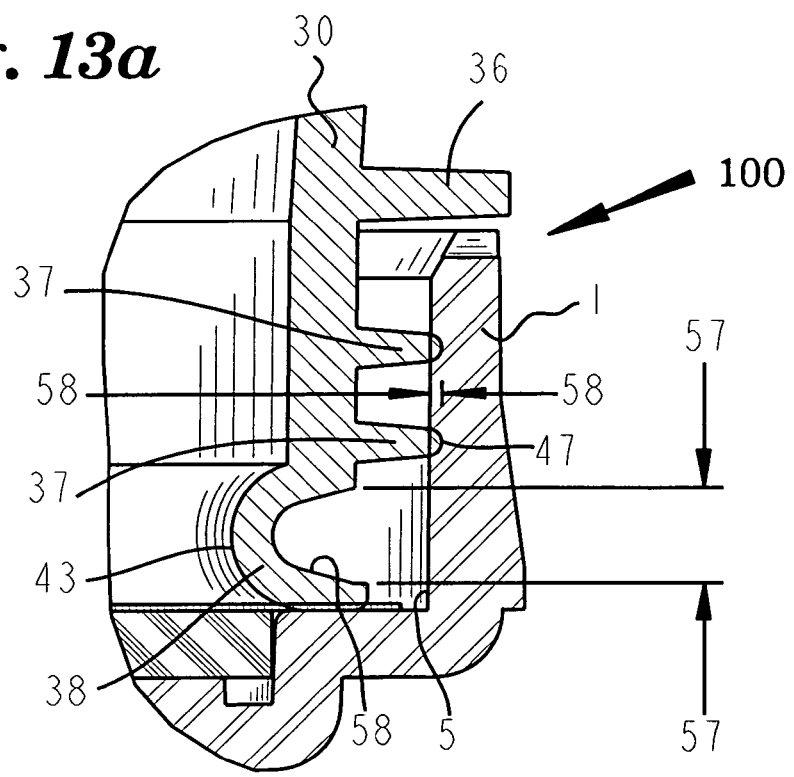
FIG. 13a is a partial cross-sectional view of a bottom portion of the assembly depicted in FIG. 12, with the sealing elements of the funnel shown in their non-deflected state.
Figure 13B:
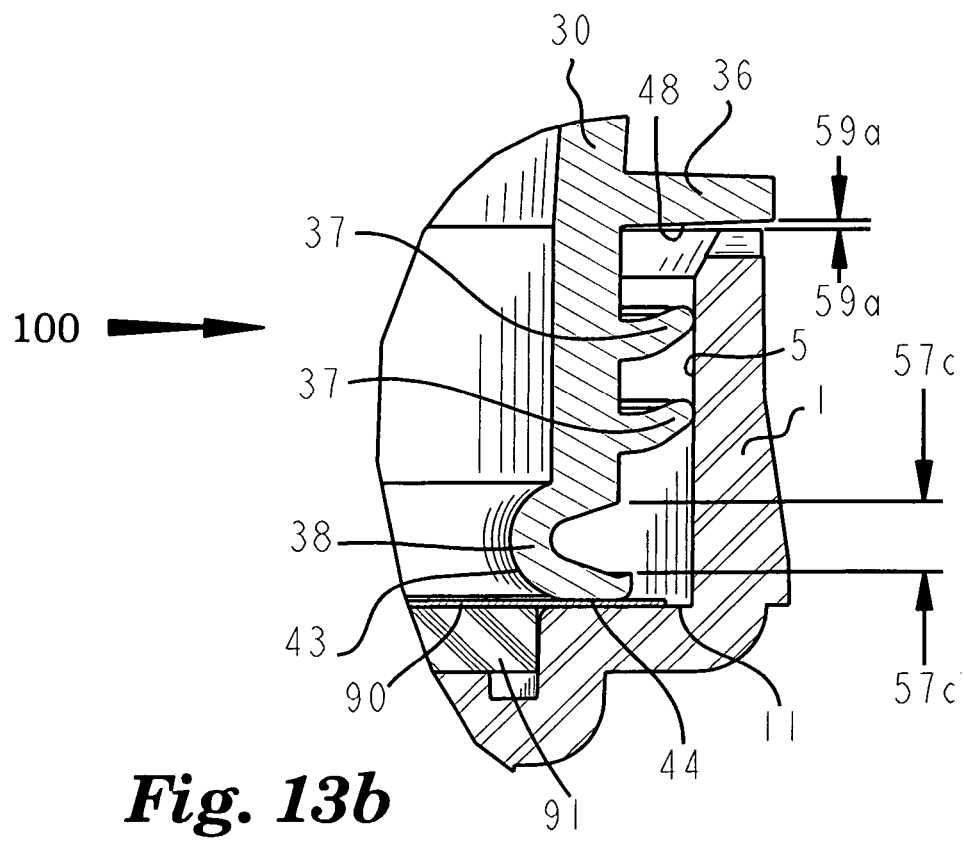
FIG. 13b is a partial cross-sectional view of a bottom portion of the assembly depicted in FIG. 12, with the sealing elements of the funnel shown in their deflected state.

FIG. 12 is an isometric view with portions thereof removed of assembly 100 in its assembled state, shown as the end user would receive it. Referring to FIG. 5, FIG. 6, FIG. 12, FIG. 13a, and FIG. 13b, absorbent pad 91 is positioned in pad well 27, of base 1, and filter means 90 is positioned in funnel well 26 of base 1, with the downstream surface of filter means 90 lying in the same plane as filter seal surface 11 of base 1. FIG. 13a is a partial cross-sectional view of assembly 100, showing theoretically how funnel 30 would fit into base 1, without deflection of the funnel elements. Referring to FIG. 13a, and FIG. 13b, the outside diameter of one or more integral flexible funnel seal ring 37 of funnel 30 must be greater than the inside diameter of inside wall 5 of funnel well 26 of base 1, for the end wall 47 of integral flexible funnel seal ring 37 to seal to inside wall 5 of funnel well 26 of base 1. FIG. 13a shows that if the outside diameter of integral flexible funnel seal ring 37 of funnel 30 is greater than the inside diameter of inside wall 5 of funnel well 26 of base 1, the radial overlap dimension 58 can be calculated as follows:

$$\frac{((\text{outside\_dia\_funnel\_seal\_ring\_37}) - (\text{inside\_dia\_inside\_wall\_5}))}{2} = \text{dimension\_58}$$

If all parts are assumed to be molded within a dimensional tolerance range of ±0.004", and if radial overlap dimension 58 equals 0.002" when the outside diameter of integral flexible funnel seal ring 37 of funnel 30 is at its minimum value, and the inside diameter of inside wall 5 of funnel well 26 of base 1 is at its maximum value, then overlap 58 will equal 0.010" when the outside diameter of integral flexible funnel seal ring 37 is at its maximum value, and the inside diameter of inside wall 5 of funnel well 26 of base 1 is at its minimum value. The one or more integral flexible funnel seal rings allows the funnel to be releasably attached to the base over a much greater range of dimensional tolerances of both the base and the funnel, than an o-ring seal would allow. Dimension 57 is the uncompressed dimension of the open end of C-shaped outer surface 58 of integral flexible filter seal 38 of funnel 30.

FIG. 13b is a partial cross-sectional view of assembly 100, showing how funnel 30 actually fits into base 1. Referring to FIG. 5, FIG. 6, FIG. 9, and FIG. 13b, when the lower portion of funnel 30 is inserted into funnel well 26 of base 1, the one or more integral flexible funnel seal rings 37 are forced to deflect upward as shown in FIG. 13b, thereby releasably attaching funnel 30 to base 1 with an interference fit between end wall 47 of one or more integral flexible funnel seal rings 37 of funnel 30 and inside wall 5 of funnel well 26 of base 1. Chamfer 20 of base 1 guides one or more integral flexible funnel seal rings 37 into funnel well 26 of base 1 during the assembly of the funnel to the base. Funnel 30 is pressed into base 1 until side wall 48 of funnel stop 36 of funnel 30, hits top outer wall 12 of base 1, so that dimension 59a shown in FIG. 13b becomes zero, thus funnel stop 36 limits the distance funnel 30 can be inserted into base 1. Funnel stop 36 also acts as a dust cap to prevent contamination from entering the space between inside wall 5 of base 1 and outer wall 59 of funnel 30. Once funnel 30 is inserted into base 1, with one or more integral flexible funnel seal rings 37 deflected upward as shown in FIG. 13b, the upward deflection of one or more integral flexible funnel seal rings 37 will prevent funnel 30 from accidentally disengaging from base 1. The thickness and diameter of the one or more integral flexible funnel seal rings 37 should be sized so that funnel 30 is releasably attached to base 1 with sufficient force to prevent accidental disengagement of funnel 30 from base 1, but not with enough force to make it difficult for the end user to remove funnel 30 from base 1 when the filtration process is complete. Integral flexible filter seal 38 of funnel 30 is compressed from its uncompressed dimension 57 shown in FIG. 13a, to its compressed dimension 57c, shown in FIG. 13b, thus releasably sealing filter means 90 between filter seal surface 11 of base 1, and bottom surface 44 of integral flexible filter seal 38 of funnel 30. By making dimension 57 sufficiently large, integral flexible filter seal 38 can provide a leak tight seal for any type of filter means with a thickness ranging from a minimum of zero to a maximum of 0.025" or more. Microporous filters and more preferably hydrophilic microporous filters are commonly used in applications for detecting bacteria, yeast, or mold, and range in thickness from 0.001" to 0.012". However in special applications it may be desirable to use a hydrophobic filter and more preferably to use a hydrophobic microporous filter. Funnel stop 36 assures that integral flexible filter seal 38 will not be over compressed. Referring to FIG. 9, dimension 50, and dimension 57, combined with the location of funnel stop 36 relative to bottom surface 44 of integral flexible filter seal 38, will determine the downward force exerted on the top surface of filter means 90, by bottom surface 44 of integral flexible filter seal 38, when funnel 30 is inserted into base 1. If dimension 50 is made sufficiently large to prevent the compression of integral flexible filter seal 38 (i.e. integral flexible filter seal 38 becomes non-flexible), filter means 90 can be releasably sealed between filter seal surface 11 of base 1, and bottom surface 44 of integral flexible filter seal 38 of funnel 30, by making the distance between bottom side wall 48 of funnel stop 36 and bottom surface 44 of integral flexible filter seal 38 greater than the height of inside wall 5 of funnel well 26 of base 1, so that funnel 30 can be inserted into base 1 until bottom surface 44 presses against the top surface of filter means 90. Likewise if integral flexible filter seal 38 is eliminated, so that the bottom surface of funnel 30 as shown in FIG. 9 becomes a horizontal surface between the bottom of inner wall 40 of funnel 30, and the bottom of outer wall 59 of funnel 30, filter means 90 can be releasably sealed between filter seal surface 11 of base 1, and bottom surface of funnel 30, by making the distance between bottom side wall 48 of funnel stop 36 and the bottom surface of funnel 30 greater than the height of inside wall 5 of funnel well 26 of base 1, so that funnel 30 can be inserted into base 1 until the bottom surface of funnel 30 presses against the top surface of filter means 90.

In applications where it is desired to seal filter means 90 to base 1 with a non-releasable seal such as a heat seal, an ultrasonic seal, a solvent seal, a glue seal, or any other type of non-releasable seal, integral flexible filter seal 38 may be eliminated.

Figure 14A:
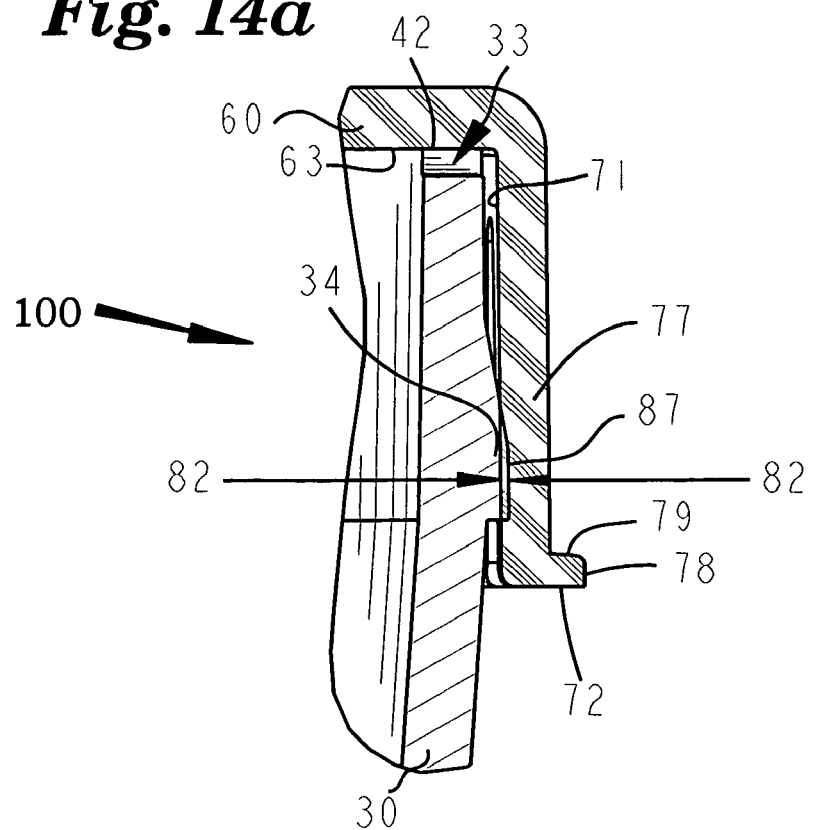
FIG. 14a is a partial cross-sectional view of a top portion of the assembly depicted in FIG. 12, with the sealing elements of the lid shown in their non-deflected state.
Figure 14B:
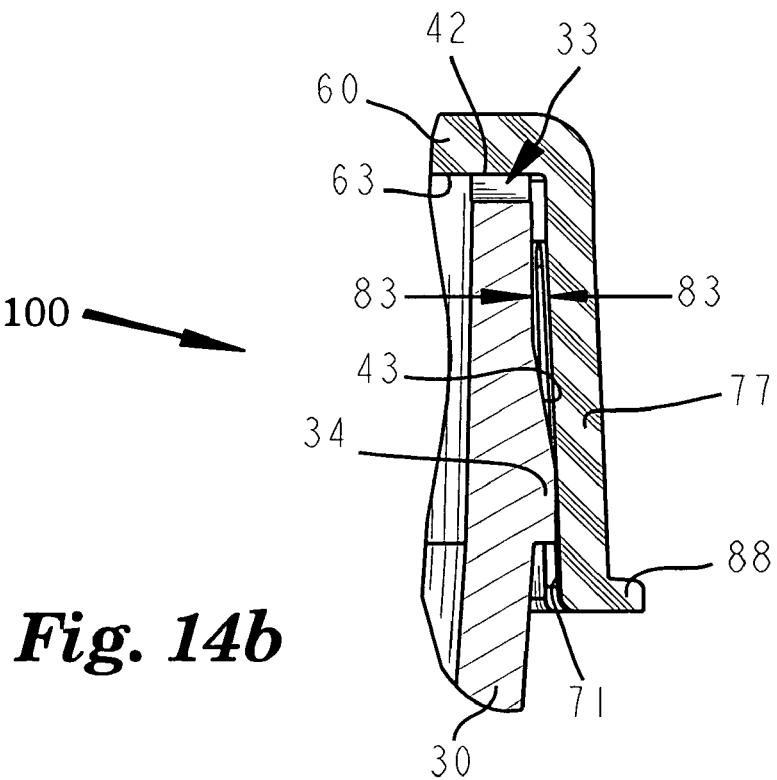
FIG. 14b is a partial cross-sectional view of a top portion of the assembly depicted in FIG. 12, with the sealing elements of the lid shown in their deflected state.

Referring to FIG. 8, FIG. 10, FIG. 11, FIG. 12, FIG. 14a and FIG. 14b, lid 60 is positioned on the top of funnel 30. FIG. 14a shows theoretically how lid 60 fits onto funnel 30, with outer wall 77 of lid 60 in its relaxed position. Referring to FIG. 10, FIG. 14a, and FIG. 14b, the outside diameter of outer surface 87 of each lid clamp tab 34 of funnel 30 must be greater than the inside diameter of inner surface 71 of lid 60, for lid 60 to fit on funnel 30 with an interference fit, to assure that lid 60 will not accidentally fall off of funnel 30. FIG. 14a shows that if the outside diameter of outer surface 87 of one or more lid clamp tabs 34 of funnel 30 is greater than the inside diameter of inner surface 71 of lid 60, the radial overlap dimension 82 can be calculated as follows:

$$\frac{(\text{outside\_dia\_lid\_clamp\_tab\_34}) - (\text{inside\_dia\_inner\_surface\_71})}{2} = \text{dimension\_82}$$

If all parts are assumed to be molded within a dimensional tolerance range of ±0.004", and if radial overlap dimension 82 equals 0.002" when the outside diameter of outer surface 87 of one or more lid clamp tabs 34 is at its minimum value, and the inside diameter of inner surface 71 of lid 60 is at its maximum value, then overlap 82 will equal 0.010" when the outside diameter of outer surface 87 of one or more lid clamp tabs 34 is at its maximum value, and the inside diameter of inner surface 71 of lid 60 is at its minimum value.

FIG. 14*b* shows how lid 60 actually fits onto funnel 30. When lid 60 is properly positioned on funnel 30, inside top surface 63 of lid 60 will be in contact with top wall 42 of funnel 30, and each segment of outer wall 77 of lid 60 that is in contact with a lid clamp tab 34 of funnel 30, will be bent out so that inner surface 71 of lid 60 is in contact with a outer surface 87 of a corresponding lid clamp tab 34. The height of inner surface 71 of outer wall 77 of lid 60 should be equal to or greater than the distance between top wall 42 of funnel 30 and the bottom edge of each lid clamp tab 34 of funnel 30, and equal to or greater than the distance between top outer wall 12 of base 1 and the bottom edge of each lid clamp tab 4 of base 1 (shown in FIG. 5). Because outer wall 77 of lid 60 is segmented by slots 64, each lid clamp tab 34 of funnel 30 will force one and possibly two segments (two segments if lid 60 is aligned so that a slot 64 of lid 60 rests against outer surface 87 of a lid clamp tab 34) to bend outward when lid 60 is positioned on the top of funnel 30. The maximum width of slot 64 of lid 60 must be less than the width of outer surface 87 of lid clamp tab 34 of funnel 30. By increasing the number of slots 64 of lid 60, the length of each segment of outer wall 77 of lid 60 between adjacent slots 64 will be reduced. As the length of each segment is reduced, the curvature of each segment will be reduced, therefore, the flexibility of each segment will be increased, thus enabling the segment to bend outward without breaking, even when the lid 60 is molded from stiff materials such as polystyrene, acrylic, polysulfone, or polycarbonate. As lid 60 is placed on funnel 30, sloped surface 43 of lid clamp tab 34 initially contacts the bottom of inner surface 71 of lid 60. Then as lid 60 is further pressed onto funnel 30, sloped surface 43 causes inner surface 71 of the appropriate segment of outer wall 77 of lid 60 to bend outward gradually until lid 60 is fully seated on funnel 30, and inner surface 71 of said segment of outer wall 77 of lid 60 is in contact with outer surface 87 of the corresponding lid clamp tab 34. Alternately, the bottom portion of inner surface 71 of the lid may be sloped, and the top surface (i.e. surface 43) of the lid clamp tab may be horizontal, as described in the description of the eleventh embodiment and shown in FIGS. 58 and 59. If either the top surface of the one or more lid clamp tabs, or the bottom of the inner surface of the appropriate segments of the lid, or both include a sloped surface, with the value of the angle of the slope of at least one of these surfaces (as defined in the eleventh embodiment) being sufficiently greater than zero degrees, the corresponding segment of the outer wall of the lid will be forced to bend outward as described above as the lid is pressed onto the funnel, until the lid is fully seated on the funnel with the bottom surface of the lid being disposed below the top of the end surface of the one or more lid clamp tabs, and more preferably with the bottom surface of the lid being disposed below the bottom surface of the one or more lid clamp tabs. This arrangement of segmented outer wall 77 of lid 60 being press fitted onto one or more lid clamp tabs 34 of funnel 30 allows the funnel and lid to be molded within a dimensional tolerance range of ±0.004" or greater, while providing an adequate interference fit between the lid and funnel to prevent accidental disengagement of the lid from the funnel, while also allowing the end user to place the lid onto the funnel, or to remove the lid from the funnel with one hand. The firmness of the interference fit can be adjusted by increasing the number of lid clamp tabs 34 to decrease the firmness, or by decreasing the number of lid clamp tabs 34 to increase the firmness, while keeping all other variables constant. In the upper limit the lid clamp tab could be made as a single annular lid clamp tab that sweeps 360° around the funnel or base. The dimensional tolerance range of 0.004" is well within the normal production range of dimensional tolerances.

Referring to FIG. 8, FIG. 11, and FIG. 14*b*, when lid 60 is positioned on funnel 30 as described above, the interior of funnel 30 is in air flow communication with the outside atmosphere through one or more vent slots 33 of funnel 30, and gap 83 between inner wall 71 of lid 60 and outer wall 39 of funnel 30. One or more slots 33 could be replaced by one or more grooves in inside top surface 63 of lid 60.

Referring to FIG. 5, FIG. 7, FIG. 10, FIG. 15*a* and FIG. 15*b*, when the filtration process is complete funnel 30 is removed from base 1, and lid 60 is removed from funnel 30, lid 60 is then placed onto base 1. Lid 60 will fit on base 1 the same as it fits on funnel 30. The nominal diameter of outer surface 23 of one or more lid clamp tabs 4 of base 1, should be the same as the nominal diameter of outer surface 87 of one or more lid clamp tabs 34 of funnel 30. Assuming that the dimensional tolerance range of base 1 is ±0.004", the above analysis of how lid 60 fits on funnel 30 applies to how lid 60 fits on base 1, with outer surface 23 of each lid clamp tab 4 of base 1, corresponding to outer surface 87 of each lid clamp tab 34 of funnel 30, and with sloped surface 13 of each lid clamp tab 4 of base 1, corresponding to sloped surface 43 of each lid clamp tab 34 of funnel 30.

Figure 15B:
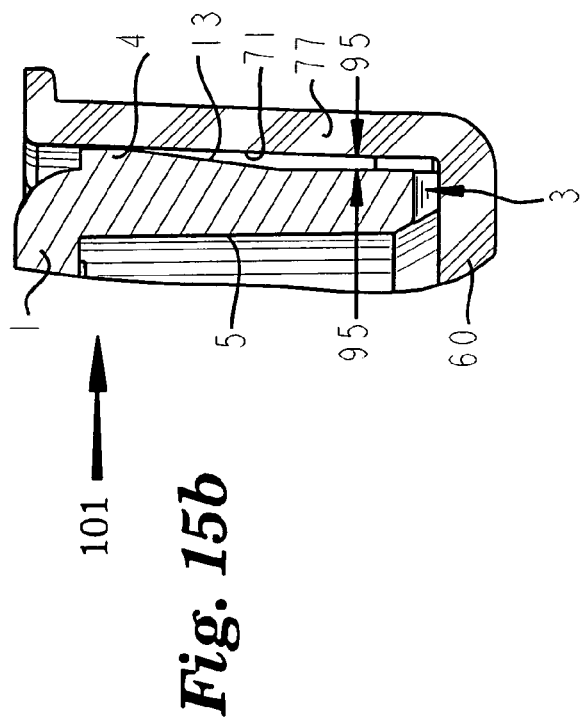
FIG. 15b is a magnified partial cross-sectional view of the assembly shown in FIG. 15a, showing the sealing means between the base and lid, and the venting means between the base and lid.

Referring to FIG. 5, and FIG. 15*b*, when lid 60 is positioned on base 1 as described above, the interior of base 1 is in air flow communication with the outside atmosphere through one or more vent slots 3 of base 1, and gap 95 between inner wall 71 of lid 60 and outside wall 6 of base 1. One or more slots 3 could be replaced by one or more grooves in inside top surface 63 of lid 60. In applications where it is not desired to vent the interior of base 1 during incubation, vent slots 3 could be eliminated.

Figure 15A:
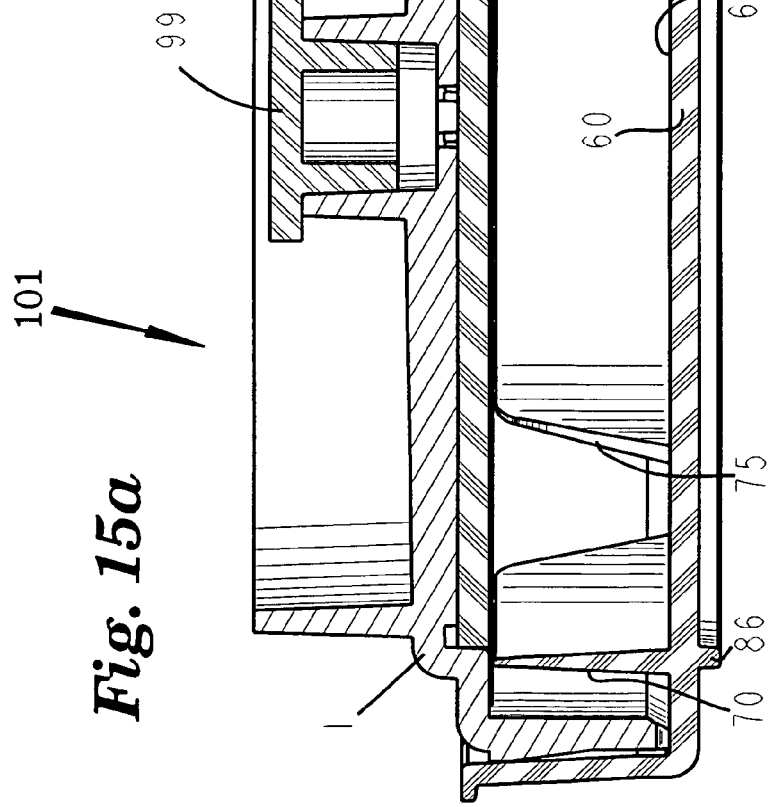
FIG. 15a is a cross-sectional view of the assembled components that comprise the first embodiment of the filtration apparatus, constructed in accordance with the principles of the present invention, without the funnel section, with the remaining components assembled in the petri dish mode, with said assembly shown inverted.

Referring to FIG. 11 and FIG. 15*a*, when funnel 30 has been removed from base 1, and lid 60 has been placed onto base 1, bottom surface 76 of filter hold down ring 75 of lid 60 holds filter means 90 in place so that the upstream surface of absorbent pad 91 remains in contact with the downstream surface of filter means 90, even when assembly 101 is inverted as shown in FIG. 15*a*. If the filter means is sealed to the base with a non-releasable seal (shown in FIG. 20 and FIG. 21) such as a heat seal, an ultrasonic seal, a solvent seal, or a glue seal, then filter hold down ring 75 of lid 60 can be eliminated, because the non-releasable seal will keep the upstream surface of absorbent pad 91 in contact with the downstream surface of filter means 90.

Referring to FIG. 5, FIG. 12 and FIG. 15*a*, the end user will receive the filtration apparatus (i.e. assembly 100) assembled as shown in FIG. 12. Filter means 90 should be a microporous filter, and more preferably a hydrophilic microporous filter with a pore size of 0.45µ or less in applications where it is desired to count cultured bacteria, cultured yeast, or cultured mold. However, in special applications it may be desirable to use a hydrophobic filter. A hydrophobic or hydrophilic microporous filter may also be used in applications where it is desired to count particulates, or in applications where it is desired to clarify a solution by filtration. However, in applications where particulates are being counted, or in applications where it is desired to clarify a solution by filtration, filter means 90 may be a hydrophobic or hydrophilic screen filter or depth filter. In the following description of the use of assembly 100 it will be assumed that filter means 90 is a hydrophilic microporous filter, and that absorbent pad 91 is a hydrophilic absorbent pad. The filtration apparatus will preferably be purchased sterile, and will be removed from its packaging and operated in a clean environment (i.e. a laminar flow hood known in the art). The operator will remove lid 60 from funnel 30, and then add a quantity of liquid to be tested to the interior of funnel 30. The liquid will wet filter means 90. A vacuum source is then connected to outlet port 10 of base 1. Outlet port 10 is in fluid flow communication with pad well 27 of base 1, hence the pressure in pad well 27 is the same as the pressure in outlet port 10 (positive or negative). The negative pressure (i.e. vacuum) in pad well 27 of base 1 will suck the liquid in funnel 30 through filter means 90, and then through absorbent pad 91, into pad well 27, into outlet port 10, and then into the vacuum source. This will continue until all of the liquid in funnel 30 has been drawn through filter means 90, and through absorbent pad 91, and until pad well 27 has been emptied. Normally the pore size of filter means 90 is small enough (i.e. approximately 0.45 µm) that the negative pressure of the vacuum does not exceed its bubble point, hence the pores of filter means 90 remain wet. However most if not all of the liquid in absorbent pad may be drawn out because of the large nominal pore size of the absorbent pad. When the filtration step is complete, the vacuum source should be turned off, and the negative pressure in outlet port 10, and hence pad well 27 should be vented to atmospheric pressure. In most applications where it is desired to detect bacteria, yeast or mold, the liquid to be tested will be water based, therefore in these applications filter 90 and absorbent pad 91 should be hydrophilic.

Referring to FIG. 12, once the filtration step is complete, the user may proceed in one of three ways. The first option is to add a quantity of liquid growth media to funnel 30, and then to momentarily reapply the vacuum to outlet port 10 of base 1. The vacuum will draw the liquid growth media through filter means 90, and then into absorbent pad 91, with any excess liquid growth media going into the vacuum source. It is important that the user turn off the vacuum source and vent outlet port 10 as soon as the level of the liquid growth media in funnel 30 reaches the top surface of filter means 90, to prevent the vacuum source from sucking the liquid growth media out of absorbent pad 91. The pores of filter means 90 will remain wet with liquid growth media because the bubble point of filter means 90 exceeds the pressure differential applied to filter means 90 by the vacuum source (i.e. vacuum pump). If the vacuum is left on too long the liquid growth media will be sucked out of absorbent pad 91 because of its large nominal pore size, and the subsequent incubation step will give a false result. One way to prevent keeping the vacuum source on to long during the step of adding liquid growth media to the apparatus as just described, is to provide the user with a vacuum pump controller that contains a continuous on/off switch to turn the vacuum pump on or off during the filtration step, and a second pulse switch that turns the vacuum pump on for a predetermined time interval (regardless of how long the user presses the pulse switch) to be used during the step of adding the liquid growth media. The controller should be designed to prevent the user from initiating a second pulse before the first time interval has been completed, this will prevent the user from accidentally turning on the vacuum pump to long, and thus sucking the liquid growth media from absorbent pad 90. The controller may be designed to prevent the start of a second pulse until the first time interval has been completed, and until an additional delay time interval has also been completed. The predetermined time interval of the vacuum pump controller would be set at the factory so that the end user would have to press the pulse switch one or more times to draw the liquid growth media into filter means 90, and into absorbent pad 91, without sucking the liquid growth media out of absorbent pad 91. The user will now remove lid 60 from funnel 30, and then remove funnel 30 from base 1, and then discard funnel 30, and then place lid 60 onto base 1, and then insert outlet port plug 99 into outlet port 10 of base 1, and then place assembly 101 into an incubator, inverted as shown in FIG. 15a. After the proper incubation time assembly 101 will be removed from the incubator, and the top surface of filter means 90 will be examined for growth of bacteria colonies, yeast colonies, or mold colonies. A grided filter as shown in FIG. 4 may be used to assist in colony counting.

Referring to FIG. 5, FIG. 11, FIG. 12 and FIG. 15a, once the filtration step is complete the second option the user has is to remove lid 60 from funnel 30, and then remove funnel 30 from base 1, and then discard funnel 30, and then place lid 60 onto base 1, and then invert assembly 101, as shown in FIG. 15a. Bottom surface 76 of filter hold down ring 75 of lid 60 holds filter means 90 in place so that the top surface of absorbent pad 91 remains in contact with the bottom surface of filter means 90, when assembly 101 is inverted as shown in FIG. 15a. If the filter means is sealed to the base with a non-releasable seal such as a heat seal, a ultrasonic seal, a solvent seal, or a glue seal, then filter hold down ring 75 of lid 60 can be eliminated, because the non-releasable seal will keep the upstream surface of absorbent pad 91 in contact with the downstream surface of filter means 90. At this point outlet port 10 of base 1 will be open (i.e. outlet port plug 99 will not be inserted in outlet port 10 as shown in FIG. 15a). A quantity of liquid growth media will now be dispensed into outlet port 10 of base 1. The liquid growth media will flow from outlet port 10 of base 1, into pad well 27 of base 1, and then into absorbent pad 91. Because the pores of filter means 90 remain wetted from the previous filtration step (because the bubble point pressure of filter means 90 is greater than the pressure differential that was applied to filter means 90 by the vacuum), air bubbles may get trapped in absorbent pad 91, as absorbent pad 91 is wetted with the liquid growth media. If an air bubble is trapped at the interface between filter means 90, and absorbent pad 91, the following incubation step may produce a false negative in the region of filter means 90 above said air bubble. The user will now insert outlet port plug 99 into outlet port 10 of base 1, and then place assembly 101 into an incubator, inverted as shown in FIG. 15a. After the proper incubation time assembly 101 will be removed from the incubator, and the top surface of filter means 90 will be examined for growth of bacteria colonies, yeast colonies, or mold colonies. A grided filter as shown in FIG. 4 may be used to assist in colony counting.

Referring to FIG. 12 if a compression seal is used to seal filter means 90 to base 1 with a releasable seal, then, once the filtration step is complete the third option the user has is to remove lid 60 from funnel 30, and then remove funnel 30 from base 1, and then discard funnel 30 and lid 60, and then remove filter means 90 from base 1 and place filter means 90 into a petri dish (known in the art) containing the desired growth media for incubation and colony counting.

Figure 16:
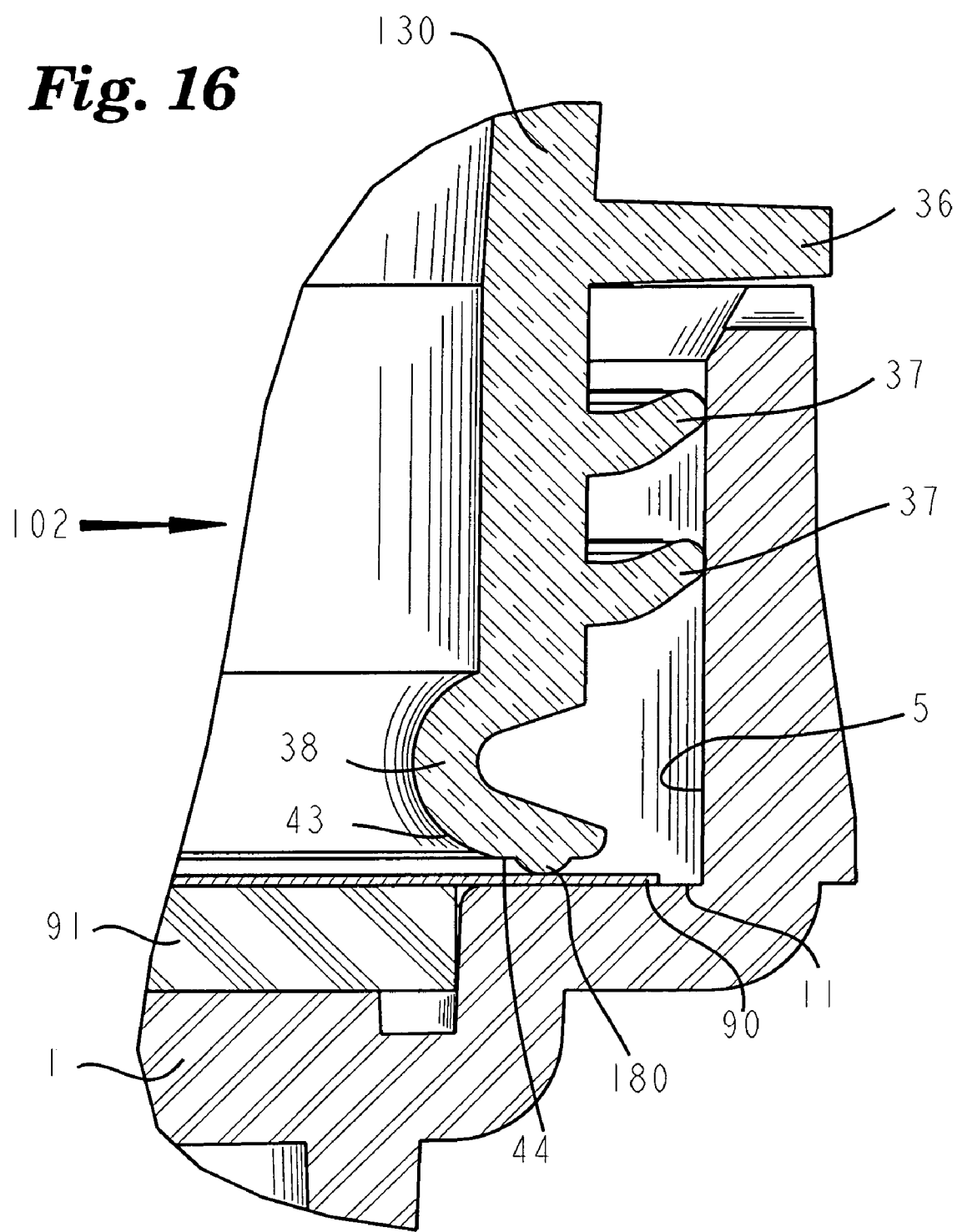
FIG. 16 is a partial cross-sectional view of the bottom portion of a second embodiment of the filtration apparatus, constructed in accordance with the principles of the present invention, usable for detecting microorganisms and particulates in liquid samples, with the sealing elements of the funnel shown in their deflected state.

A second embodiment of the filtration apparatus constructed in accordance with the principles of the present invention, is shown in FIG. 16. This embodiment shown as assembly 102 contains the same component parts as the first embodiment described above, with the exception that funnel 30 is replaced with funnel 130. The features of funnel 130 that are identical to those of funnel 30, have been given the same reference numbers as the corresponding feature of funnel 30. In addition to containing all of the features that funnel 30 contains, funnel 130 contains seal bead 180, which protrudes from bottom surface 44, of integral flexible filter seal 38. Although seal bead 180 as illustrated in FIG. 16 is circular in shape, it could be formed from any other shape such as rectangular, elliptical, ect. When funnel 130 is inserted into base 1, integral flexible filter seal 38 of funnel 130 will be compressed as explained above for funnel 30. Hence filter means 90 will be sealed between filter seal surface 11 of base 1, and the bottom of seal bead 180 of funnel 130. The circular shape of seal bead 180 as shown in FIG. 16, and its small contact area with filter means 90, and the spring force applied to seal bead 180 from the compressed integral flexible filter seal 38 of funnel 130 provide a leak tight seal around the outer periphery of filter means 90.

Figure 17:
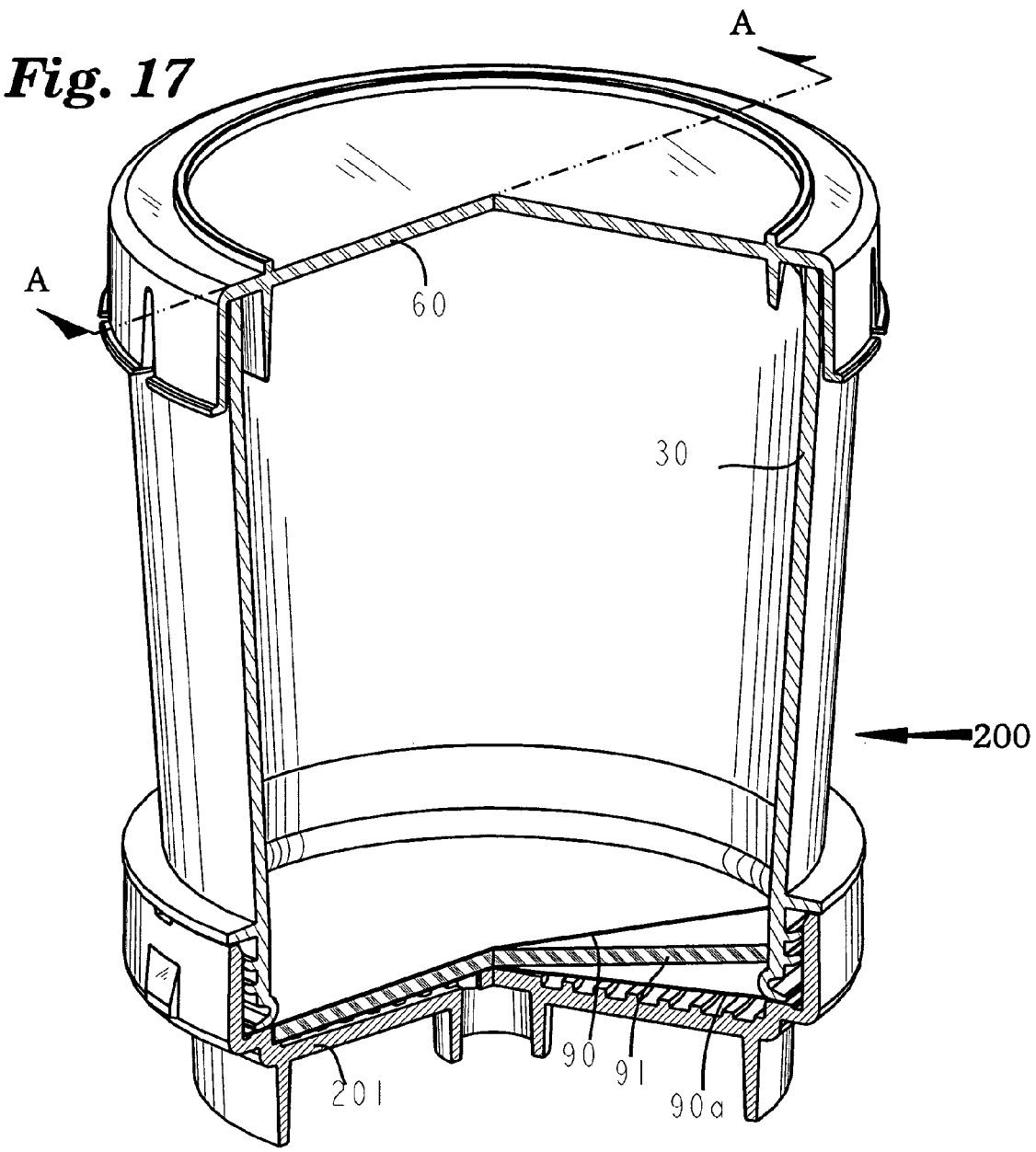
FIG. 17 is an isometric view, having portions thereof removed, of the assembled components that comprise the third embodiment of the filtration apparatus, constructed in accordance with the principles of the present invention, usable for detecting microorganisms and particulates in liquid samples.
Figures 18, 18A:
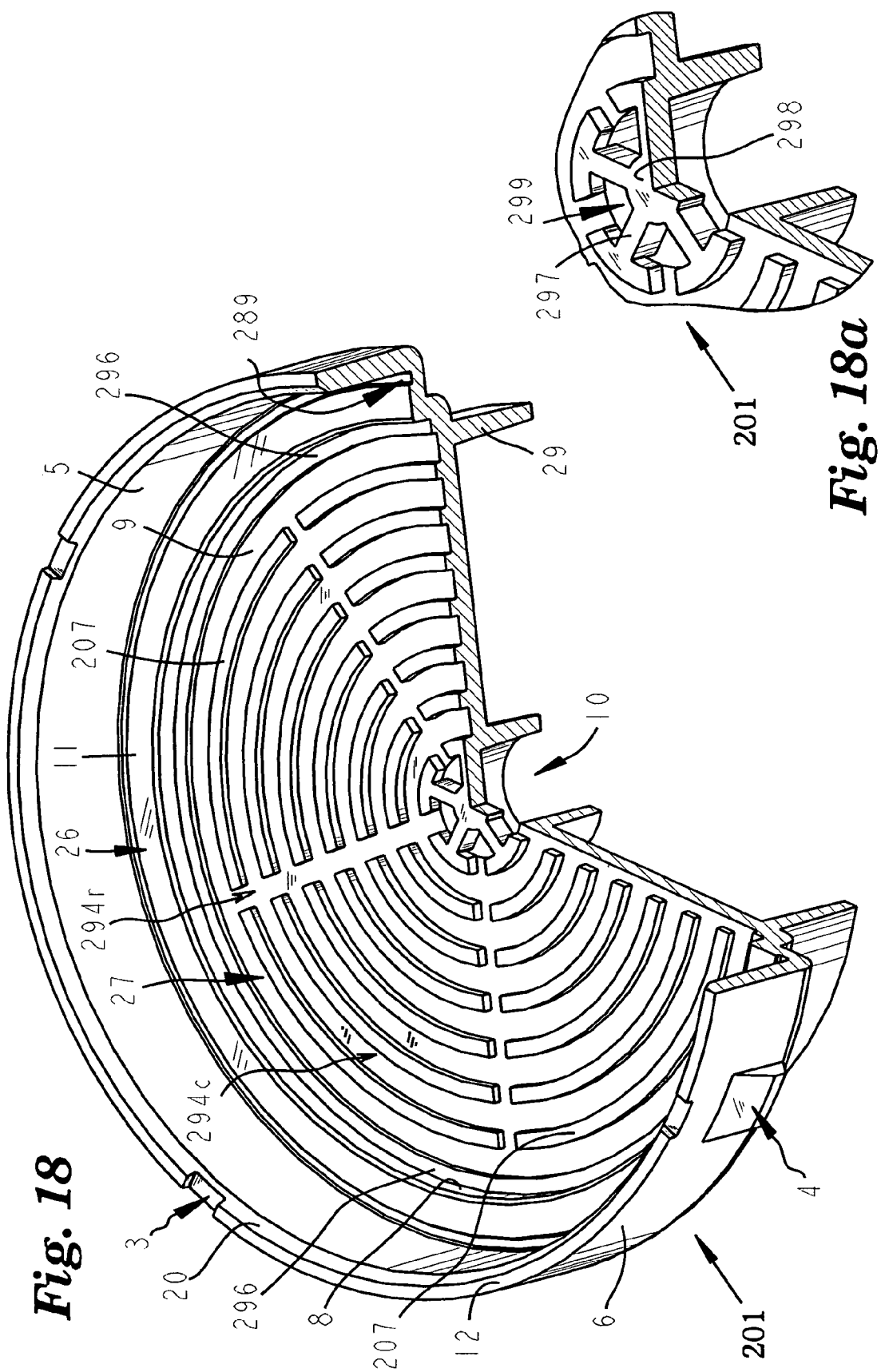
FIG. 18 is an isometric view, having portions thereof removed, of the base component of the assembly depicted in FIG. 17.
FIG. 18a is a magnified partial isometric view of the center portion of the base component depicted in FIG. 18.

An third embodiment of the filtration apparatus constructed in accordance with the principles of the present invention, is shown in FIG. 17. Assembly 200 shown in FIG. 17 contains, base 201, funnel 30 (alternately funnel 130 could replace funnel 30), lid 60, filter means 90 (preferably a microporous filter and for most applications more preferably a hydrophilic microporous filter, although in special applications a hydrophobic microporous filter may be used), absorbent pad 91 (preferably a hydrophilic absorbent pad for most applications, although in special applications a hydrophobic absorbent pad may be used), and lower filter means 90a (preferably a microporous filter and for most applications more preferably a hydrophilic microporous filter, although in special applications a hydrophobic microporous filter may be used). Referring to FIG. 18 and FIG. 18a, base 201 contains funnel well 26, bounded by filter seal surface 11, and inside wall 5. Inside wall 5 contains chamfer 20. Base 201 also contains a pad well 27, bounded by lower inside wall 8, and bottom inside surface 9. The outer edge of filter seal surface 11 contains groove 289. Base 201 contains outlet port 10. Bottom inside surface 9 may slope downward from its outside periphery toward outlet port 10. Outlet port 10 is in fluid flow communication with pad well 27. Base 201 also contains a means to support lower filter means 90a, shown here by circular filter support ribs 207, which protrude upward from bottom inside surface 9. Circular filter support ribs 207 are interrupted by one or more radial drain channels 294r. Circular drain channels 294c (i.e. the space between adjacent circular filter support ribs 207), are in fluid flow communication with radial drain channels 294r. Base 201 also contains a means to support the portion of lower filter means 90a that bridges outlet port 10, shown in FIG. 18, and FIG. 18a, as central filter support hub 298, and one or more radial filter support ribs 297 which attach central filter support hub 298 to the inner most circular filter support rib 207. One or more passages 299 place one or more radial drain channels 294r in fluid flow communication with outlet port 10. The top surface of filter support ribs 207 preferably lie in a horizontal plane, said plane being located below filter seal surface 11, a distance approximately equal to the sum of the thickness of absorbent pad 91, plus the thickness of lower filter means 90a.

Figure 17A:
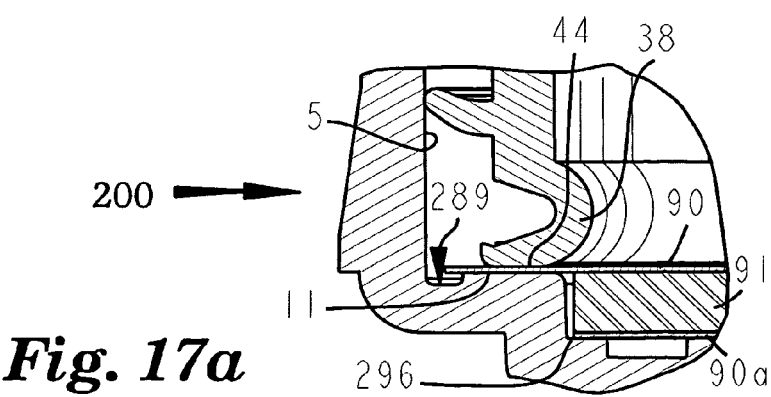
FIG. 17a is a partial cross-sectional view of the bottom portion of the assembly depicted in FIG. 17, showing the filter sealing means, and a means to assist in removing the filter means from the base.

Although circular filter support ribs 207 are shown as segmented circular ribs, any filter support structure that provides sufficient support for lower filter means 90a, and that provides the proper drainage of filtered liquid from pad well 27 to outlet port 10 may be used. Top outer wall 12 of base 201 contains one or more vent slots 3 that correspond to vent slots 3 of base 1. Outside wall 6 of base 1 contains one or more lid clamp tabs 4, that protrude from outside wall 6, that correspond to clamp tabs 4 of base 1. Base 201 also contains support ring 29 corresponding to support ring 29 of base 1. Support ring 29 supports base 201 when base 201 is placed on a flat surface. Outlet port 10 is in fluid flow communication with pad well 27. The outer most circular filter support rib containing seal surface 296 is not interrupted. Referring to FIG. 17 and FIG. 17a, lower filter means 90a is placed into pad well 27 of base 201, so that the downstream surface of lower filter means 90a rests on and is supported by circular filter support ribs 207, central filter support hub 298, and one or more radial filter support ribs 297. The downstream surface of the outer periphery of lower filter means 90a rests on seal surface 296 of the uninterrupted outer most circular support rib. Absorbent pad 91 is placed into pad well 27 of base 201 on top of lower filter means 90a. Filter means 90 is placed into funnel well 26, with the downstream surface of filter means 90 lying in the same plane as filter seal surface 11 of base 201. Referring to FIG. 17a, the outer periphery of filter means 90 is sealed between bottom surface 44 of integral flexible filter seal 38 of funnel 30, and filter seal surface 11 of base 201, and the outer periphery of lower filter means 90a is sealed between seal surface 296 of base 201, and the outer periphery of the bottom face of absorbent pad 91. Alternately, the outer periphery of lower filter means 90a could be non-releasably sealed to seal surface 296 using a heat seal, an ultrasonic seal, a solvent seal, a glue seal or any other type of leak tight seal. Likewise, filter means 90 could be non-releasably sealed to filter seal surface 11 using a heat seal, an ultrasonic seal, a solvent seal, a glue seal or any other type of leak tight seal.

The end user will receive the filtration apparatus (i.e. assembly 200) assembled as shown in FIG. 17. The filtration apparatus will preferably be purchased sterile, and will be removed from its packaging and operated in a clean environment (i.e. a laminar flow hood known in the art). The operator will remove lid 60 from funnel 30, and then add a quantity of liquid to be tested to the interior of funnel 30. The lid will then preferably be repositioned on the top of funnel 30. The liquid will wet filter means 90 and absorbent pad 91. A vacuum source is then connected to outlet port 10 of base 201. Outlet port 10 is in fluid flow communication with one or more radial drain channels 294r of pad well 27 of base 201, through one or more passages 299 of pad well 27 of base 201, and circular drain channels 294c of pad well 27 of base 201 are in fluid flow communication with one or more radial drain channels 294r of pad well 27 of base 201, hence the pressure in pad well 27 is the same as the pressure in outlet port 10 (positive or negative). The negative pressure (i.e. vacuum) in pad well 27 of base 201 will suck the liquid in funnel 30 through filter means 90, and then through absorbent pad 91, and then through lower filter means 90a, into pad well 27, into outlet port 10, and then into the vacuum source. This will continue until all of the liquid in funnel 30 has been drawn through filter means 90, and through absorbent pad 91, and through lower filter means 90a, until pad well 27 has been emptied. Normally the pore size of filter means 90 is small enough (i.e. approximately 0.45 μm) that the negative pressure of the vacuum does not exceed its bubble point, hence the pores of filter means 90 remain wet. The pore size of lower filter means 90a should be just small enough that the negative pressure of the vacuum does not exceed its bubble point (i.e. between 0.8 µm and 1.2 µm), hence the pores of lower filter means 90*a* will also remain wet, as will absorbent pad 91. When the filtration step is complete, the vacuum source should be turned off, and the negative pressure in outlet port 10, and hence pad well 27 should be vented to atmospheric pressure. In most applications where it is desired to detect bacteria, yeast or mold, the liquid to be tested will be water based, therefore in these applications filter 90, filter 90*a*, and absorbent pad 91 should be hydrophilic.

Referring to FIG. 17, once the filtration step is complete, the user will add a quantity of liquid growth media to funnel 30, and then reapply the vacuum to outlet port 10 of base 201. The vacuum will draw the liquid growth media through filter means 90, and then through absorbent pad 91, and then through lower filter means 90*a*, with any excess liquid growth media going into the vacuum source. Because the bubble points of both filter means 90, and lower filter means 90*a* are greater than the negative pressure applied by the vacuum source, filter means 90, absorbent pad 91, and lower filter means 90*a*, will all remain wetted with liquid growth media regardless of how long the vacuum source is kept on. The user will now remove lid 60 from funnel 30, then remove funnel 30 from base 201, then discard funnel 30, then place lid 60 onto base 201, then insert outlet port plug 99 (not shown) into outlet port 10 of base 201, and then place the resultant assembly into an incubator, inverted as described above for the first embodiment. After the proper incubation time the assembly will be removed from the incubator, and the top surface of filter means 90 will be examined for growth of bacteria colonies, or yeast colonies, or mold colonies. Filter means 90 may be a grided filter to assist the user in colony counting.

In some applications it is desired to skip the step of adding liquid growth media. Instead it is desired to remove filter means 90, from base 201 of the third embodiment (or base 1 of the first or second embodiment), and place filter means 90 into a separate petri dish (not shown) that contains a growth media for the incubation step. Referring to FIG. 17*a* and FIG. 18, if the outside diameter of filter means 90 is smaller than the outside diameter of groove 289 of base 201, then filter means 90 may be placed into funnel well 26 of base 201 so that the central axis of filter means 90 is aligned with the central axis of funnel well 26 of base 201, or filter means 90 may be placed into funnel well 26 of base 201 so that a portion of the outside edge of filter means 90 contacts a portion of the bottom of inside wall 5 of funnel well 26 of base 201, or filter means 90 may be placed into funnel well 26 of base 201 somewhere in-between these two extremes. The outside diameter of filter means 90 should be made small enough so that regardless of the position of filter means 90 in funnel well 26 of base 201, the user will be able to remove filter means 90 from base 201 (after funnel 30 has been removed from base 201), by placing the tip of a forceps into groove 289 of base 201 at a point where filter means 90 does not cover groove 289, then grabbing the outer periphery of filter means 90 with the forceps and removing filter means 90 from base 201 with the forceps, so that filter means 90 may be placed into a separate petri dish. However, the outside diameter of filter means 90 should be large enough so that regardless of the position of filter means 90 in funnel well 26 of base 201, the outer periphery of filter means 90 will be sealed between bottom surface 44 of integral flexible filter seal 38 of funnel 30 and filter seal surface 11 of base 201. Groove 289 could be also added to the base any other embodiment described in this application.

Figure 19:
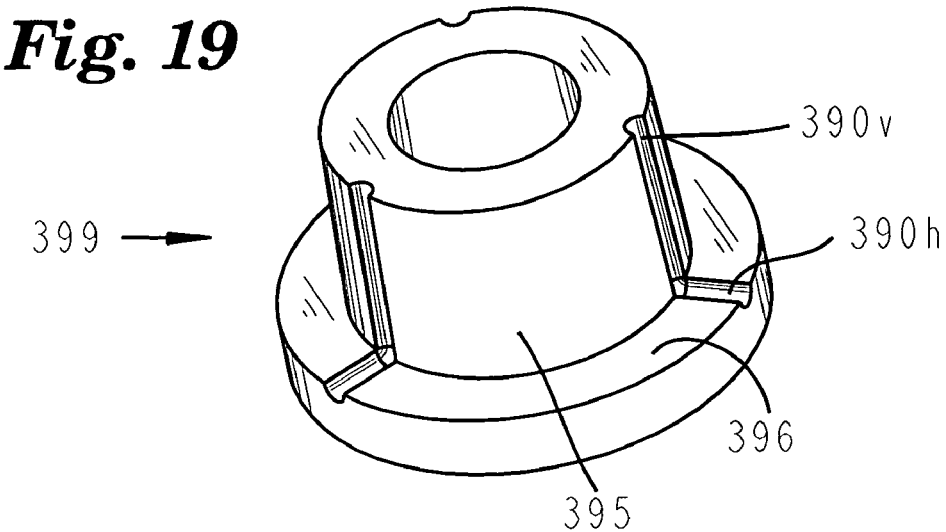
FIG. 19 is a isometric view of a vented plug for the outlet port of the base component.

Vented outlet port plug 399, shown in FIG. 19 contains one or more grooves 390*v*, and an equal number of corresponding grooves 390*h*. Otherwise vented outlet port plug 399 is identical to outlet port plug 99 shown in FIG. 15*a*. Referring to FIG. 6, FIG. 15*a*, and FIG. 19, outlet port plug 99 can be replaced by vented outlet port plug 399. With vented outlet port plug 399 inserted into outlet port 10 of base 1, surface 395 of vented outlet port plug 399 will be press fitted into outlet tube inside surface 15 of base 1, and surface 396 of vented outlet port plug 399 will be releasably sealed to outlet tube bottom surface 2 of base 1, and one or more grooves 390*v*, and corresponding one or more grooves 390*h* will place the outside atmosphere in air flow communication with pad well 27 of base 1. There are two advantages to using vented outlet port plug 399. The first advantage is that as vented outlet port plug 399 is inserted into outlet port 10 of base 1 (after the step of adding liquid growth media), it is impossible to create a positive pressure in pad well 27 of base 1, because of the vent grooves on vented outlet port plug 399. When outlet port plug 99 (the non-vented outlet port plug) is press fitted into outlet port 10 of base 1 (after the step of adding liquid growth media), a positive pressure may be developed in pad well 27 of base 1, this positive pressure may dislodge a portion of the downstream surface of filter means 90 from a portion of the upstream surface of absorbent pad 91, possibly preventing colony growth in the dislodged portion of filter means 90 during the incubation process. A second advantage of using vented outlet port plug 399 is that pad well 27 is kept at atmospheric pressure during the incubation step. This will facilitate the flow of liquid growth media from absorbent pad 91, into the pores of filter means 90, to enhance colony growth on the top surface of filter means 90. Vented outlet port plug 399 may also be used with base 201 in the same manner that it is used with base 1.

Figure 20:
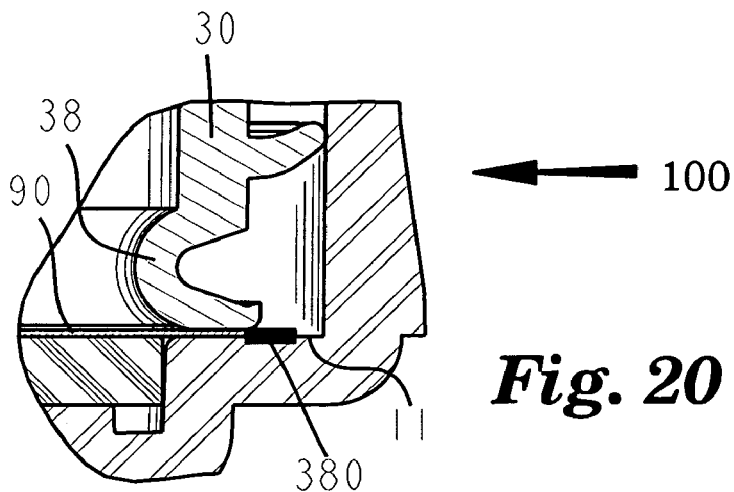
FIG. 20 is a partial cross-sectional view of the bottom portion of the assembly depicted in FIG. 12, showing the filter means permanently sealed to the base.
Figure 21:
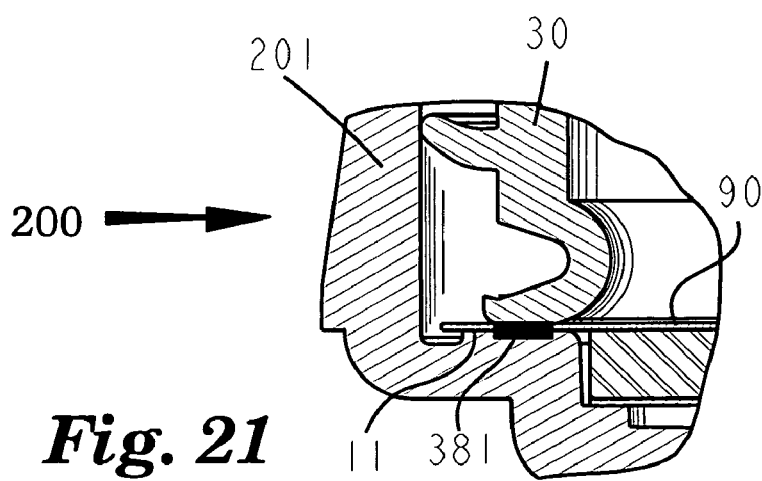
FIG. 21 is a partial cross-sectional view of the bottom portion of the assembly depicted in FIG. 17, showing the filter means permanently sealed to the base.

A fourth embodiment of the filtration apparatus constructed in accordance with the principles of the present invention, is shown in FIG. 20 and FIG. 21. Filter means 90 is permanently sealed with a non-releasable seal to the base of the apparatus in the fourth embodiment. The fourth embodiment can use the same component parts as the first embodiment, or as the second embodiment, or as the third embodiment, or any combination thereof. FIG. 20 using the components of assembly 100, shows that the outer periphery of filter means 90 may be permanently sealed to filter seal surface 11, of base 1, or of base 201, using seal 380 outside of the seal provided by integral flexible filter seal 38 of funnel 30. Seal 380 may be a heat seal, an ultrasonic seal, a solvent seal, a glue seal or any other type of leak tight seal. FIG. 21 using the components of assembly 200, shows that the outer periphery of filter means 90 may be permanently sealed to filter seal surface 11, of base 1, or of base 201, using seal 381 below the seal provided by integral flexible filter seal 38 of funnel 30. Seal 381 may be a heat seal, an ultrasonic seal, a glue seal or any other type of leak tight seal.

Figure 22:
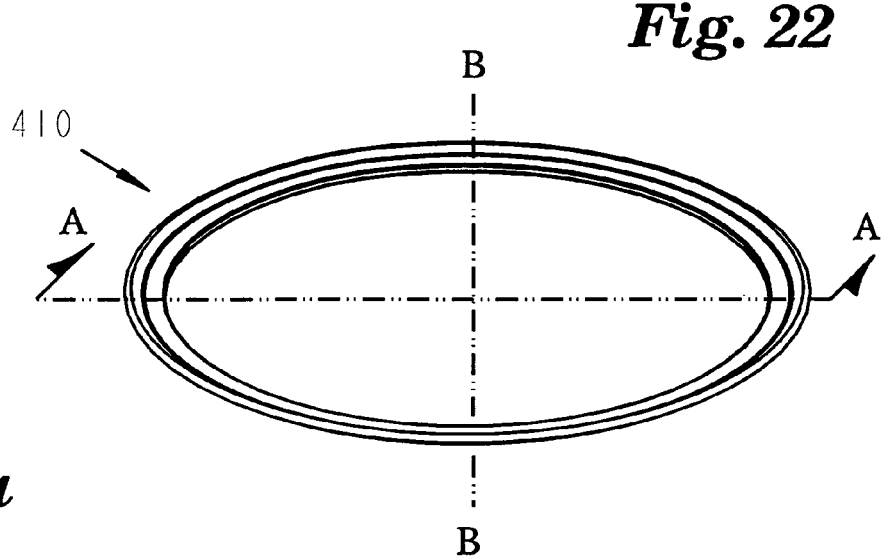
FIG. 22 is an isometric view of a filter seal ring.
Figure 22A:
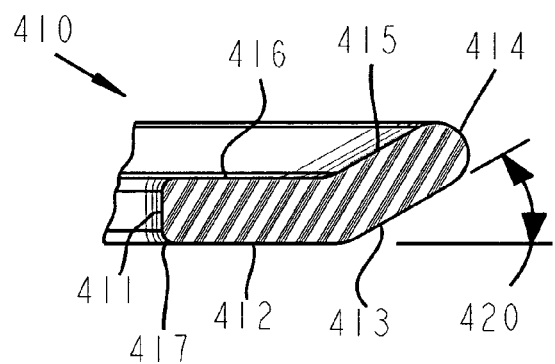
FIG. 22a is a partial cross-sectional view of the seal ring depicted in FIG. 22.
Figure 23:
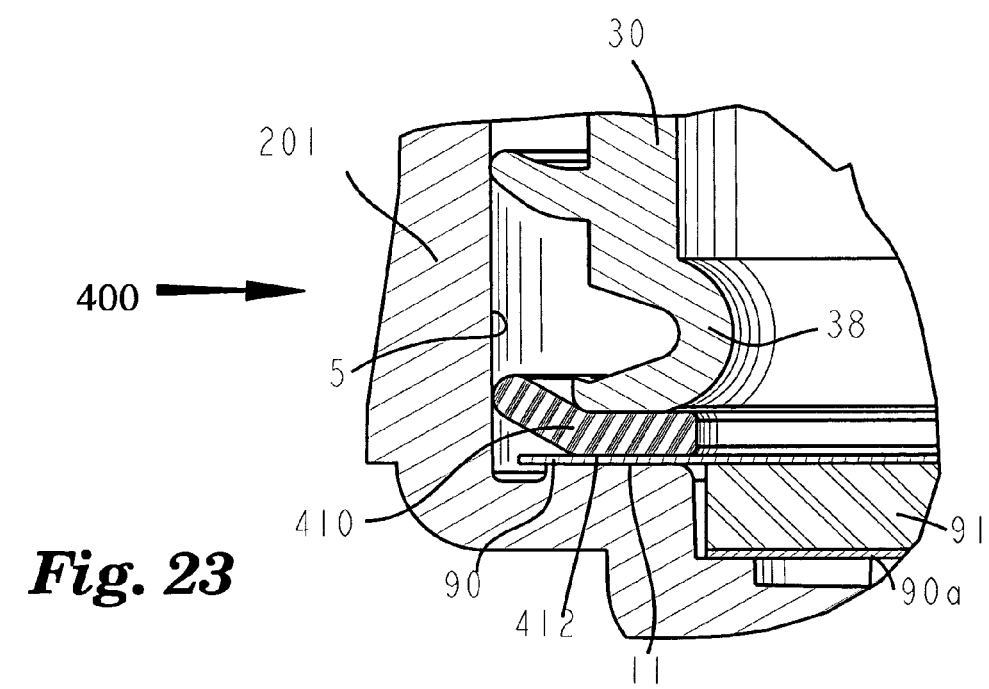
FIG. 23 is a partial cross-sectional view of an assembly incorporating the filter seal ring depicted in FIG. 22.

A fifth embodiment of the filtration apparatus constructed in accordance with the principles of the present invention, is shown in FIG. 22, FIG. 22*a*, and FIG. 23. Filter means 90 is permanently sealed to the apparatus in the fifth embodiment. The fifth embodiment can use the same component parts as the first embodiment, or as the second embodiment, or as the third embodiment, or any combination thereof. FIG. 22 shows filter seal ring 410. FIG. 22*a* shows a partial cross-section of filter seal ring 410, taken through section A-A, shown in FIG. 22. Referring to FIG. 22*a*, the bottom of filter seal ring 410 contains filter seal surface 412, and surface 413. Surface 413 is adjacent to filter seal surface 412, and sloped at an angle 420 relative to filter seal surface 412. Surface 416 of filter seal ring 410 is parallel to filter seal surface 412, and surface 415 is parallel to surface 413. End surface 414 is preferably rounded as shown. Surface 411 of filter seal ring 410 preferably contain round 417. Filter seal ring 410 is formed by revolving the section shown in FIG. 22a about axis B-B, shown in FIG. 22. Assembly 400 shown in FIG. 23 uses the same component parts as assembly 200 shown in FIG. 17. Assembly 400 could, however, use the component parts of assembly 100 shown in FIG. 12, or the component parts of assembly 102 shown in FIG. 16. Filter means 90 of assembly 400 is permanently sealed between filter seal surface 412 of filter seal ring 410, and filter seal surface 11 of base 201. End surface 414 of filter seal ring 410 is press fitted to inside wall 5 of funnel well 26 of base 201. Assembly 400 is assembled by the manufacturer by first inserting the necessary filter means and absorbent pad into base 201, and then press fitting filter seal ring 410 into the base. Filter seal ring 410 is preferably molded from a flexible plastic such as polypropylene, or polyethylene, but could be molded from a rigid non-elastomeric material such as styrene, acrylic, polycarbonate, or from similar materials. The outside diameter of filter seal ring 410 must be larger than the inside diameter of inside wall 5 of base 201, or of base 1 when seal ring 410 is press fitted into base 201. The prior analysis of dimensional tolerances between integral flexible funnel seal rings 37 of funnel 30, and inside wall 5 of base 1, applies to the fit between filter seal ring 410 and inside wall 5 of base 1, or of base 201. As filter seal ring 410 is pressed into base 1, or base 201, angle 420 of filter seal ring 410 will increase so that end surface 414 of filter seal ring 410 conforms to inside wall 5 of base 1, or of base 201. After the filter seal ring has been pressed into the base, the funnel is then pressed into the base so that the bottom face of integral flexible filter seal 38 of funnel 30 presses against surface 416 of filter seal ring 410. The filter seal ring provides a liquid tight seal. The seal ring could be made from other shapes such as an annular ring that does not contain sloped surfaces 413 and 415, and the seal ring could also be sealed to the base using a heat seal, an ultrasonic seal, a solvent seal, a glue seal, or any other type of seal, in which case it would not be necessary to have a press fit between the seal ring and the base.

Figure 24:
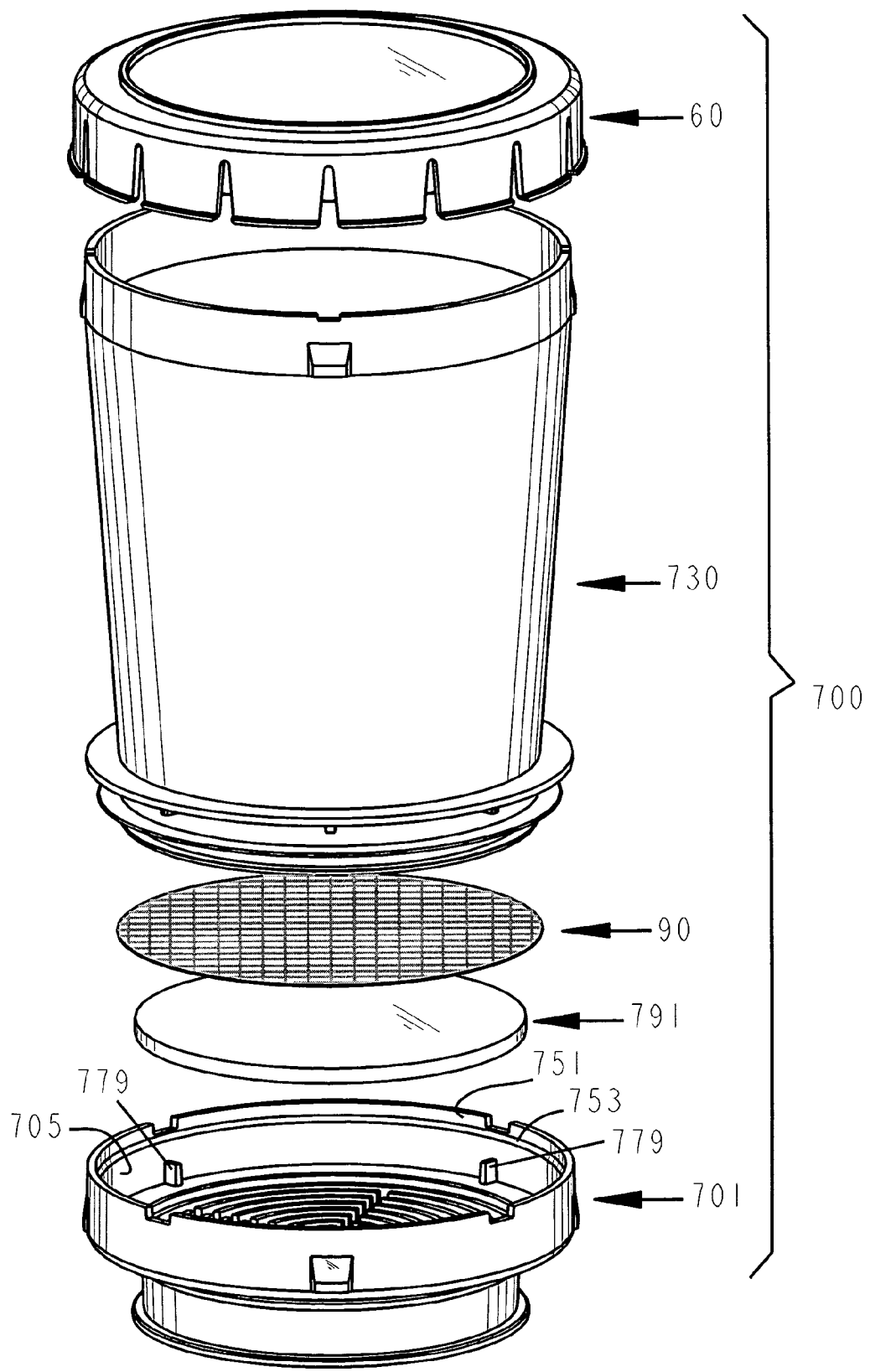
FIG. 24 is an exploded isometric view of the components that comprise the sixth embodiment of the filtration apparatus, constructed in accordance with the principles of the present invention, usable for detecting microorganisms and particulates in liquid samples.
Figure 25:
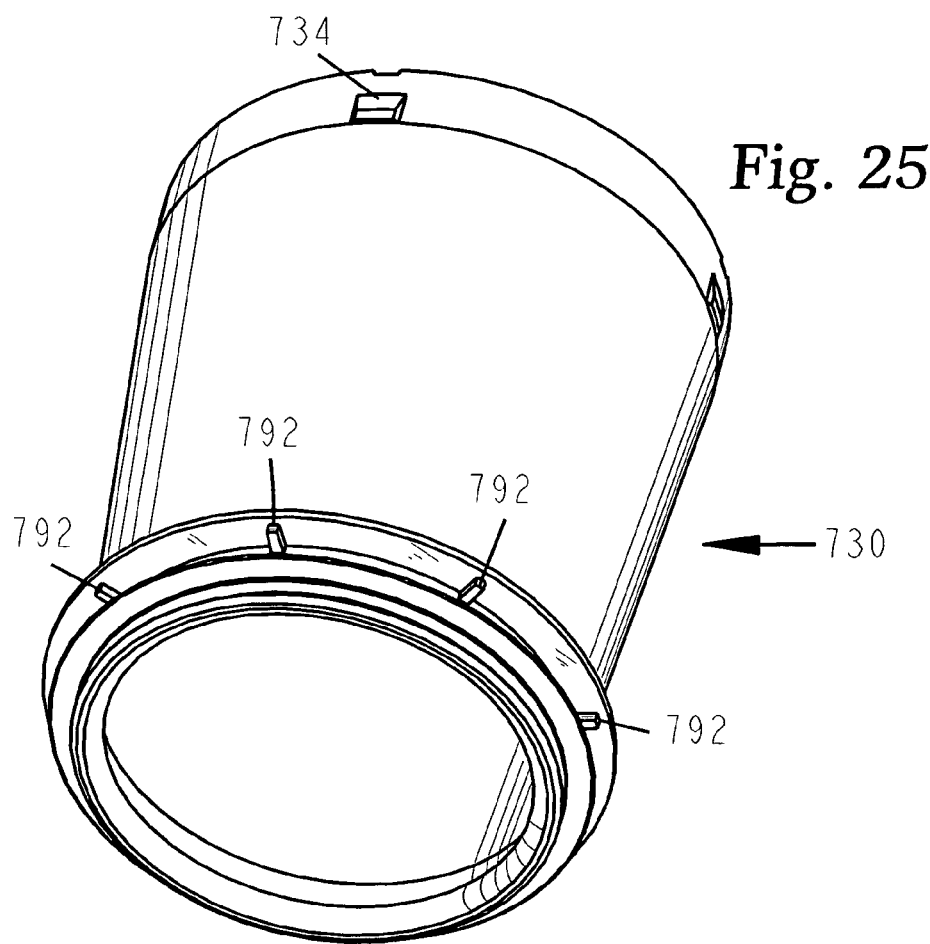
FIG. 25 is an isometric view of the funnel element of the apparatus shown in FIG. 24.

A sixth embodiment of the filtration apparatus constructed in accordance with the principles of the present invention, is shown in FIG. 24 through FIG. 28. FIG. 24 is an exploded view of assembly 700. Assembly 700 contains base 701, absorbent pad 791 (in most applications preferably a hydrophilic absorbent pad), filter means 90 (preferably a microporous filter, and in most applications more preferably a hydrophilic microporous filter), funnel 730, and lid 60. Base 701 is the same as base 201 shown in FIG. 18 with the exception that base 701 contains three or more filter centering tabs 779 (preferably equally spaced around the periphery of inside wall 705), and a counter bore defined by side wall 751, and chamfer 753. Absorbent pad 791 is the same as absorbent pad 91 shown in FIG. 17, with the exception that absorbent pad 791 is thicker than absorbent pad 91. Absorbent pad 791 may be comprised of two or more thin layers of absorbent pad material. Funnel 730 is the same as funnel 30 shown in FIG. 8, FIG. 12, and FIG. 17, with the exception that funnel 730 contains funnel centering tabs 792. Although funnel 730 is shown with one integral flexible funnel seal ring 737, more than one integral flexible funnel seal ring could be used. Lid 60 is the same as lid 60 shown in FIG. 17.

Figure 26:
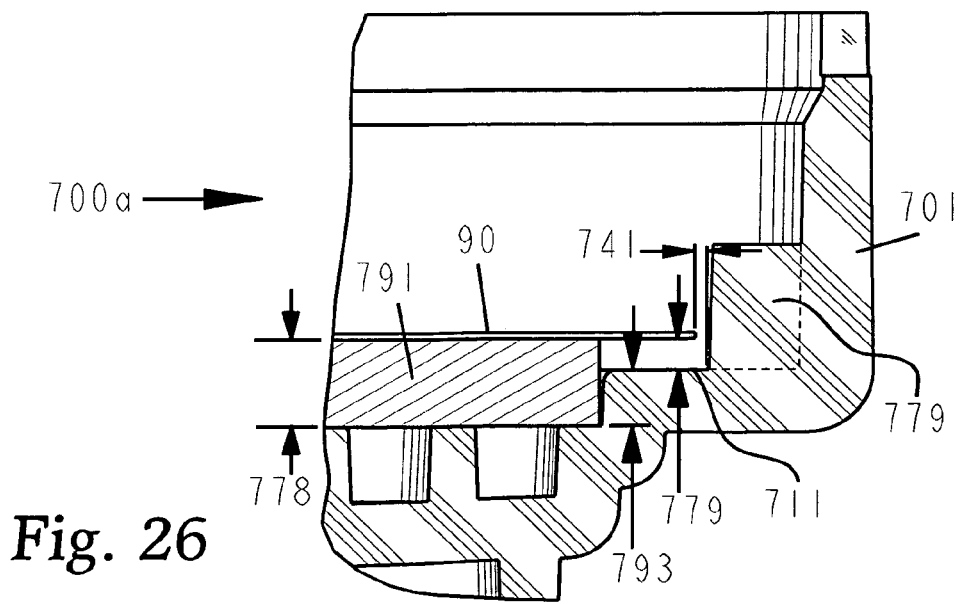
FIG. 26 is a partial cross-sectional view of a sub-assembly of the base, absorbent pad, and filter elements of the apparatus shown in FIG. 24.

FIG. 26 shows sub-assembly 700a with absorbent pad 791 positioned in pad well 27 of base 701 (pad well 27 is shown in FIG. 18 and described above), and with filter means 90 positioned on top of absorbent pad 791 and centered in base 701 by three or more filter centering tabs 779. Referring to FIG. 26, the diameter of filter means 90 may be made slightly smaller than the inside diameter of filter centering tabs 779 so that a small gap 741 will exist between one or more filter centering tabs and filter means 741. This small difference in diameter makes it easier to place filter means 90 into base 701. FIG. 26 shows that the thickness 778 of absorbent pad 791 is substantially greater than the height 793 of pad well 27 of base 701. Therefore when the filter means 90 is positioned on top of absorbent pad 791 as shown in FIG. 26, a gap 779 will exist between the downstream side of filter means 90 and filter seal surface 711 of base 701.

Figure 27:
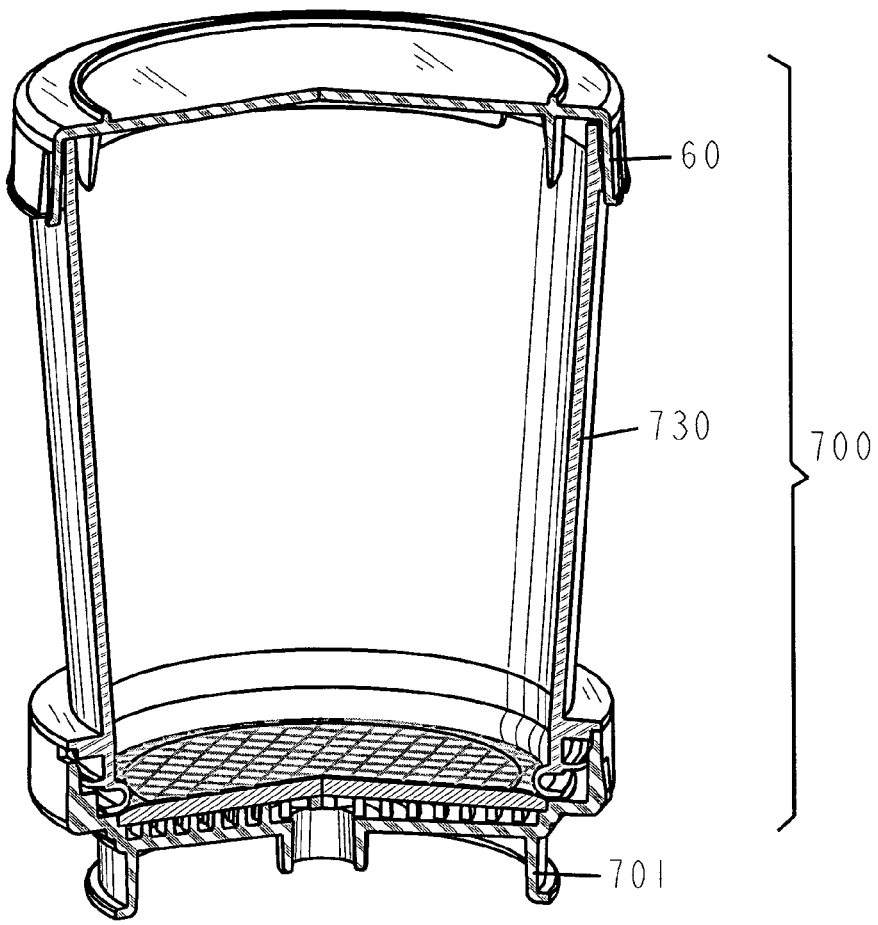
FIG. 27 is an isometric view, having portions thereof removed, of the assembled filtration apparatus shown in FIG. 24.

FIG. 27 shows assembly 700 in the assembled state. FIG. 28 is a partial cross-sectional view of a portion of assembly 700 showing in detail how funnel 730 is assembled to base 701. The counter bore at the upper part of inside wall 705 of base 701, defined by side wall 751 and chamfer 753, allows integral flexible funnel seal ring 737 of funnel 730 (in its un-deflected state) to be easily located and centered in the top portion of base 701. Chamfer 753 then guides integral flexible funnel seal ring 737 of funnel 730 as it is deflected and pressed into the lower portion of inside wall 705, to attain the press fit shown in FIG. 28. With funnel 730 seated in base 701 as shown in FIG. 28, one or more integral flexible funnel seal rings 737 of funnel 730 will secure funnel 730 to base 701, and three or more funnel centering tabs 792 will be positioned in the counter bore of inside wall 705 of base 701, defined by side wall 751 and chamfer 753. Funnel centering tabs 792 keep funnel 730 centered in base 701. With funnel 730 seated in base 701, bottom surface 744 of integral flexible filter seal 738 of funnel 730, and inner surface 743 of integral flexible filter seal 738 of funnel 730, push down on the outer periphery of filter means 90, so that the outer periphery of filter means 90 is sealed with a compression seal between bottom surface 744 of integral flexible filter seal 738 of funnel 730, and filter seal surface 711 of base 701. Because absorbent pad 791 is substantially thicker than the height of pad well 27 of base 701 (as explained above), the outer periphery of absorbent pad 791 will be compressed by filter means 90 which is in turn compressed by the lower portion of inner surface 743 of filter seal 738, as shown in FIG. 28. Compressed absorbent pad 791 exerts an upward force on filter means 90, thus keeping filter means 90 in tension and wrinkle free. Alternately the outer periphery of filter means 90 may be non-releasably sealed to filter seal surface 711 (using a heat seal, an ultrasonic seal, a solvent seal, a glue seal, or any other type of non-releasable leak tight seal) before funnel 730 is inserted into base 701, in which case the outer periphery of absorbent pad 791 will be compressed by filter means 90. Compressed absorbent pad 791 will exert an upward force on filter means 90, thus keeping filter means 90 in tension and wrinkle free.

The end user will use assembly 700 the same as assembly 200 is used, as explained above. When the liquid to be tested is added to funnel 730, filter means 90 and absorbent pad 791 will be wetted. If the liquid to be tested is water based, then filter means 90 and absorbent pad 791 should be hydrophilic, but if the liquid to be tested is non-water based it may be desirable that filter means 90 and absorbent pad 791 be hydrophobic. Because filter means 90 is very thin it will not swell appreciably in thickness, but will expand in diameter as it is wetted. If the spring force of integral flexible filter seal 738 of funnel 730 is great enough to prevent filter means 90 from expanding radially between bottom surface 744 of integral flexible filter seal 738 of funnel 730, and filter seal surface 711 of base 701, or if a non-releasable seal is used to seal filter means 90 to base 701, filter means 90 will wrinkle if an absorbent pad with a thickness approximately equal to the height of pad well 27 is used (as described in the previous embodiments of the present invention). This wrinkling will prevent portions of the downstream surface of filter means 90 from contacting the upstream surface of absorbent pad 791, which in turn will impede colony growth during the incubation cycle. However, when an absorbent pad that has a thickness that is substantially greater than the height of the pad well is used as shown in FIG. 26 and FIG. 28 (with a releasable or non-releasable seal between filter means 90 and base 701), filter means 90 will start out in tension (i.e. wrinkle free) when dry, and will remain in tension as absorbent pad 791 swells in thickness as it becomes wet. Because the thickness of absorbent pad 791 is much greater than the thickness of filter means 90, absorbent pad 791 will swell much more in thickness than filter means 90 will, thereby keeping filter means 90 in tension and wrinkle free when both the filter means and the absorbent pad are wet. This will assure uniform contact between the downstream surface of filter means 90 and the upstream surface of absorbent pad 791, thus assuring proper incubation of any colonies trapped on the upstream surface of filter means 90, during the incubation cycle. Absorbent pad 791 should be made thick enough to assure that filter means 90 remains wrinkle free throughout the filtration process, but not so thick to cause a brittle filter means to fracture in the region where it is compressed.

Any of the above assemblies can be used to detect particulates in a liquid sample. The procedure is the same with the exception that the addition of liquid growth media, and incubation step are not necessary.

Figure 31:
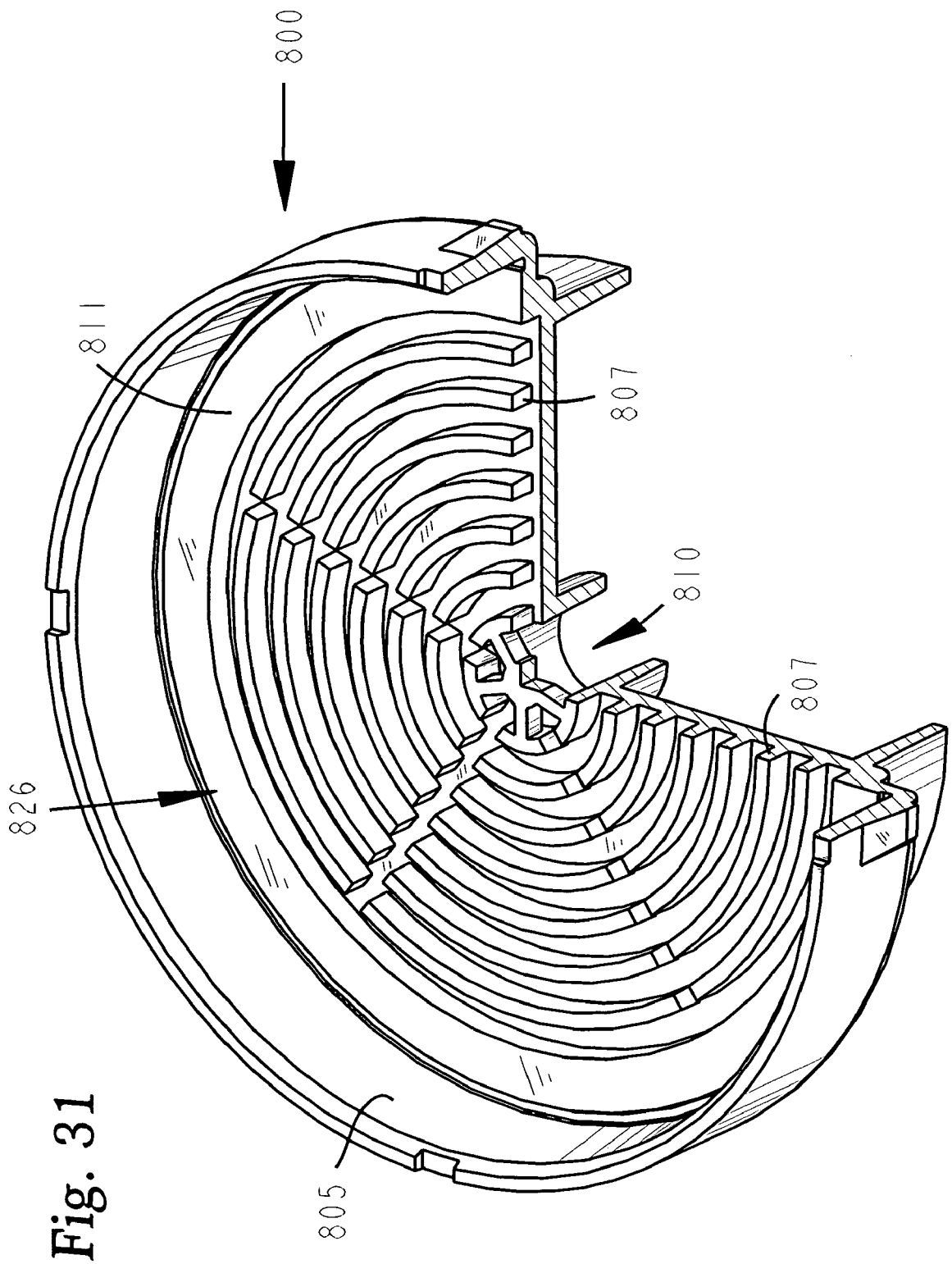
FIG. 31 is an isometric view, having portions thereof removed, of the base component of the assembly depicted in FIG. 29.
Figure 32:
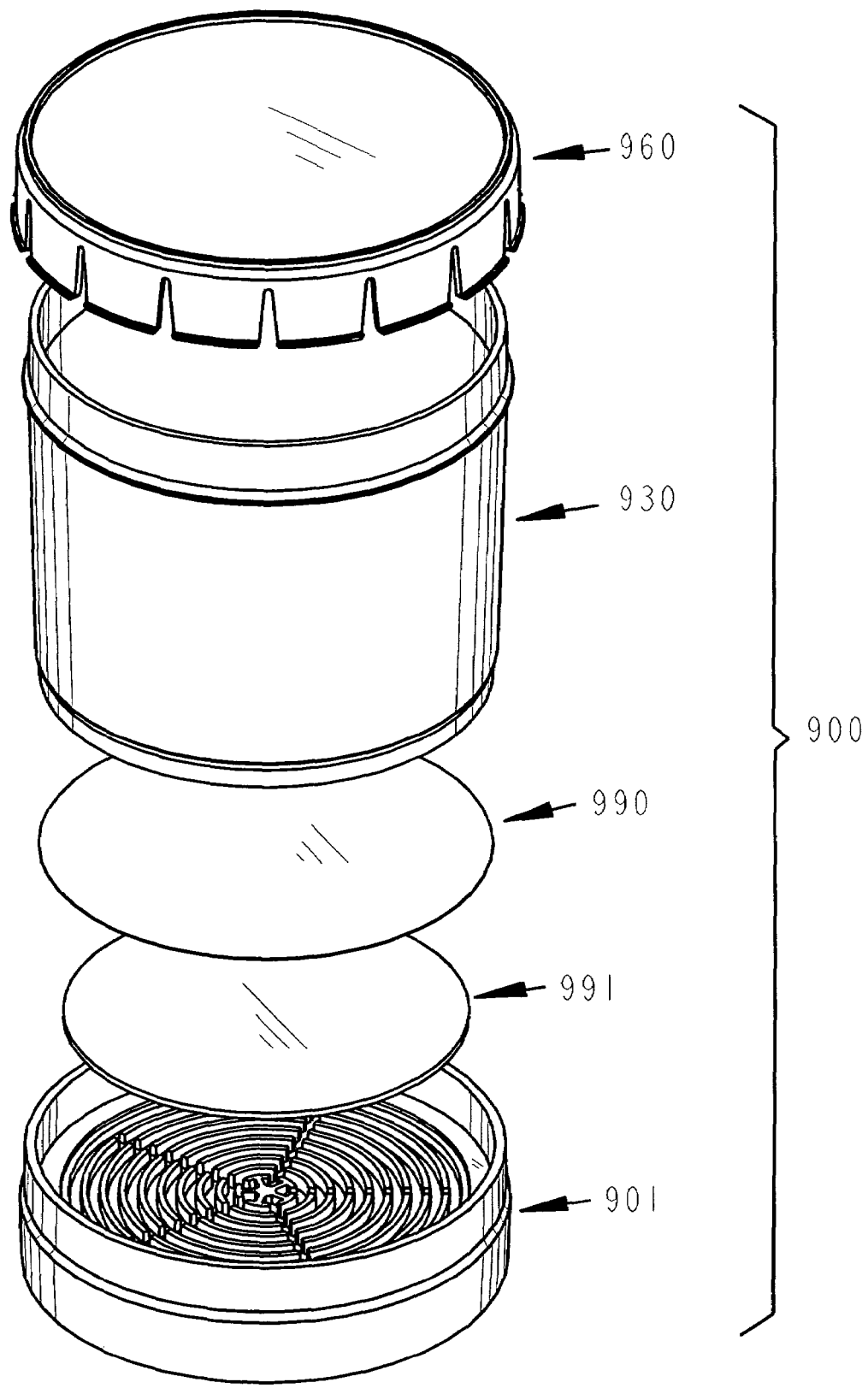
FIG. 32 is an exploded isometric view of the components that comprise the eighth embodiment of the filtration apparatus, constructed in accordance with the principles of the present invention, usable for detecting microorganisms and particulates in liquid samples.
Figure 33A:
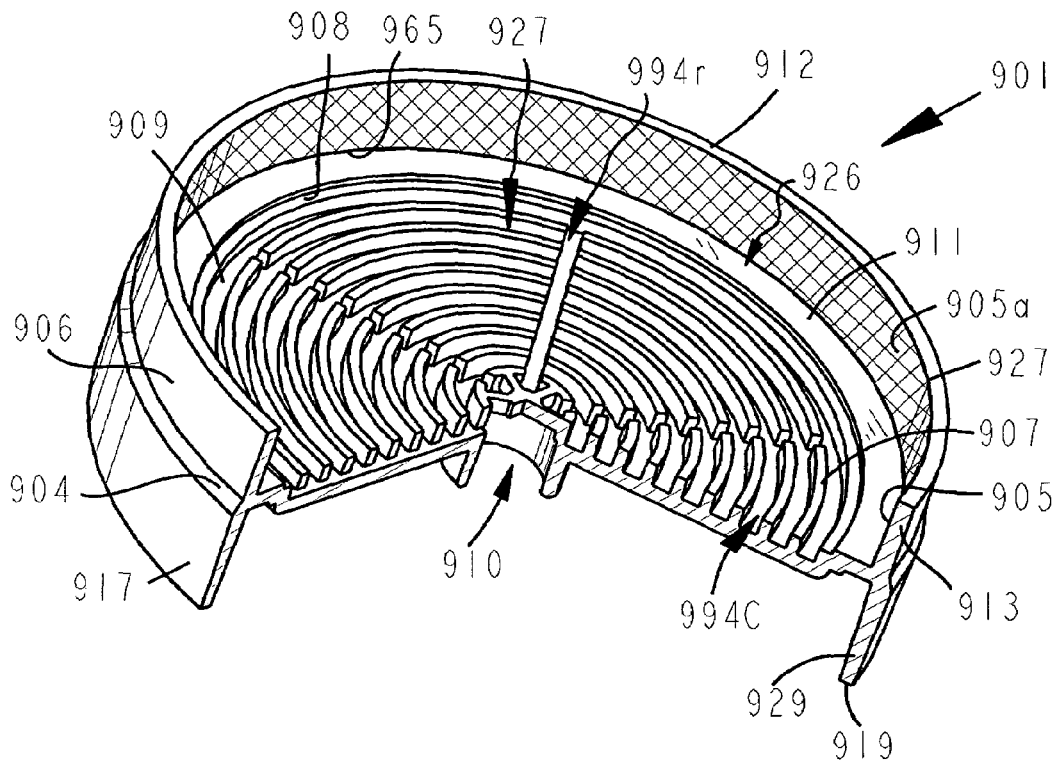
FIG. 33a is an isometric view, having portions thereof removed, of the base component of the assembly depicted in FIG. 32.
Figure 33B:
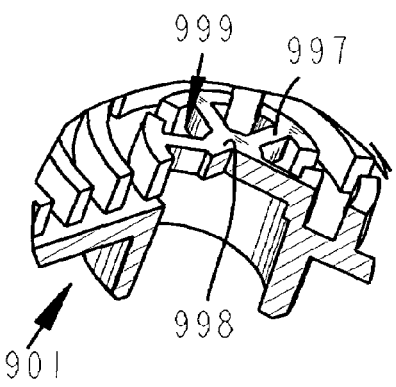
Figure 33C:
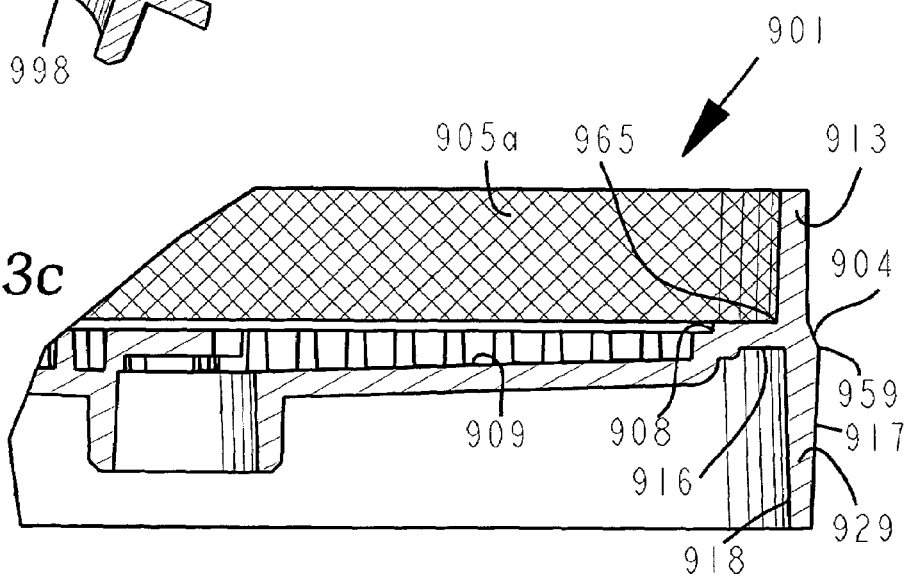

A seventh embodiment of the filtration apparatus constructed in accordance with the principles of the present invention, is shown in FIG. 29 and FIG. 31. Funnel 830 is press fitted into funnel well 826 of base 801 with an interference fit between outer wall 859 of funnel 830 and inside wall 805 of base 801. In this embodiment the one or more integral flexible funnel seal rings are eliminated. Funnel 830 contains integral flexible filter seal 838, disposed around the bottom edge of funnel 830. Base 801 does not contain a pad well for an absorbent pad disposed in the bottom of funnel well 26. A filter means 890 is compression sealed between bottom surface 844 of integral flexible filter seal 838 of funnel 830, and filter seal surface 811 of base 801. The filter means may be a microporous filter, a screen filter, or a depth filter, and may be either hydrophilic or hydrophobic. The filter means is supported by a filter support means shown as filter support ribs 807 disposed in the bottom of the funnel well. The filter support means could be any filter support arrangement that provides the proper support for the filter means, and that also provides a fluid flow communication means between the downstream side of the filter means, and outlet port 810. The voids around filter support ribs 807 are in fluid flow communication with outlet port 810. Although the apparatus shown in FIG. 29 does not compensate for the range of dimensional tolerances between outer wall 859 of funnel 830, and inside wall 805 of base 801, as a funnel with one or more integral flexible funnel seal rings would, it does provides more compensation than the prior art because of integral flexible filter seal 838. The greater the range of flexing of integral flexible filter seal 838 (i.e. the greater the distance that the integral flexible filter seal can be compressed), the greater the compensation will be.

The apparatus shown in FIG. 29 could be used to count bacterial colonies, yeast colonies, or mold colonies, from a liquid sample as follows: The end user will receive the filtration apparatus (i.e. assembly 800) assembled as shown in FIG. 29. The filtration apparatus will preferably be purchased sterile, and will be removed from its packaging and operated in a clean environment (i.e. a laminar flow hood known in the art). The operator will remove the lid (not shown) from funnel 830, and then add a quantity of liquid to be tested to the interior of funnel 830. The liquid will wet filter means 890. A vacuum source is then connected to outlet port 810 of base 801. The vacuum source will cause the liquid in the funnel to be filtered through filter means 890, with the downstream liquid being sucked into the vacuum source. For this type of application the filter means should be a microporous filter with a pore size of 0.45μ or smaller, and more preferably a hydrophilic microporous filter. The bacteria, yeast, or mold in the liquid sample will be trapped on the upstream surface of filter means 890. Funnel 830 will then be removed from base 805, then filter means 890 will be removed from base 801 as described above, then filter means 890 will be placed into a petri dish that contains the proper growth media (not shown). The petri dish will then be placed into an oven for incubation of the bacteria, or of the yeast, or of the mold. When the incubation cycle is complete the colonies can be counted.

The apparatus shown in FIG. 29 could be used to count particulates in a liquid sample as follows: The end user will receive the filtration apparatus (i.e. assembly 800) assembled as shown in FIG. 29. The filtration apparatus will preferably be purchased sterile, and will be removed from its packaging and operated in a clean environment (i.e. a laminar flow hood known in the art). The operator will remove the lid (not shown) from funnel 830, and then add a quantity of liquid to be tested to the interior of funnel 830. The liquid will wet filter means 890. A vacuum source is then connected to outlet port 810 of base 801. The vacuum source will cause the liquid in the funnel to be filtered through filter means 890, with the downstream liquid being sucked into the vacuum source. For this type of application the filter means could be a microporous filter, a screen filter, or a depth filter, although a microporous filter is preferable with a pore size small enough to trap the smallest particles that are desired to be counted. For water based liquids the filter should be hydrophilic, and for solvent based liquids the filter should be hydrophobic. When the filtration is complete, the particles to be counted will be trapped on the upstream surface of the filter means, where they can be counted either in the funnel, or alternately the funnel can be carefully removed from the base, and then the trapped particles can be counted with the filter in the base, or the filter could be carefully removed from the base for counting.

The vacuum filtration apparatus shown in FIG. 29 could use a funnel without an integral flexible filter seal 838, in which case the filter means 890 would be sealed with a compression seal between filter seal surface 811 of base 801, and bottom surface 899 of funnel 830. In any of the previous embodiments, the integral flexible filter seal could also be eliminated, and the filter means could be sealed between the seal surface of the appropriate base and the bottom surface of the appropriate funnel. Also in any of the previous embodiments where it is not desired to remove the filter from the base after filtration, the filter means could be sealed to the base with a non-releasable seal, such as a heat seal, an ultrasonic seal, a solvent seal, a glue seal, or any other leak tight non-releasable seal.

An eight embodiment of the filtration apparatus constructed in accordance with the principles of the present invention, is shown in FIG. 32 through FIG. 38*d*. Referring to FIG. 33*a*, FIG. 33*b*, and FIG. 33*c*, base 901 contains funnel well 926, bounded by filter seal surface 911, and inner surface 905 of side wall 913, with side wall 913 disposed above and substantially perpendicular to filter seal surface 911. However, the base could contain a groove like groove 289 of base 201, shown in FIG. 18, in which case a portion of the side wall would be disposed above and substantially perpendicular to the filter seal surface. Inner surface 905 may contain a draft angle to improve moldability of the base. Inner surface 905 is preferably textured to increase its coefficient of friction, as shown by the cross-hatching 905a on inner surface 905 in FIG. 33a and FIG. 33c. Base 901 also contains a pad well 927, bounded by lower inside wall 908, and bottom inside surface 909. Base 901 contains outlet port 910. Bottom inside surface 909 may slope downward from its outside periphery toward outlet port 910. Outlet port 910 is in fluid flow communication with pad well 927. Base 901 also contains a means to support absorbent pad 991, shown here by circular filter support ribs 907, which protrude upward from bottom inside surface 909. Circular filter support ribs 907 are interrupted by one or more radial drain channels 994r. Circular drain channels 994c (i.e. the space between adjacent circular filter support ribs 907), are in fluid flow communication with radial drain channels 994r. Base 901 also contains a means to support the portion of absorbent pad 991 that bridges outlet port 910, shown in FIG. 33a, and FIG. 33b, as central filter support hub 998, and one or more radial filter support ribs 997 which attach central filter support hub 998 to the inner most circular filter support rib 907. One or more passages 999 place one or more radial drain channels 994r in fluid flow communication with outlet port 910. The top surface of filter support ribs 907 preferably lie in a horizontal plane, said plane being located below filter seal surface 11, a distance that is preferably less than or equal to the thickness of absorbent pad 991. Although circular filter support ribs 907 are shown as segmented circular ribs, any filter support structure that provides sufficient support for absorbent pad 991, and that provides the proper drainage of filtered liquid from pad well 927 to outlet port 910 may be used. Base 901 may also contain support ring 929 corresponding to support ring 29 of base 1. Support ring 929 supports base 901 when base 901 is placed on a flat surface. Outlet port 910 is in fluid flow communication with pad well 927. The outer most circular filter support rib is preferably not interrupted. Base 901 is preferably made from a pliable material such as low density polyethylene, high density polyethylene, or polypropylene, but is not limited to these materials. Although it is preferred to make base 901 circular as shown, it could be made in another shape such as square or rectangular.

FIG. 34a, FIG. 34b, and FIG. 34c show funnel 930. Funnel 930 contains outside wall 935. The bottom of outside wall 935 may contain step 936 and chamfer 937. Referring to FIG. 34b, step 936 has a bottom outside diameter D2 that is preferably smaller than the outside diameter D3 of outside wall 935. Chamfer 937 acts as a transition between step 936 and outside wall 935. Step 936 and outside wall 935 may contain an outward taper (i.e. their respective diameters may increase with height). The top portion 939 of outside wall 935 may contain an inward taper (i.e. its diameter may decrease with height). As will be seen later the portion of outside wall 935 that fits into base 901 preferably contains texture 933 (shown by cross-hatching in FIG. 34a) to increase its coefficient of friction. Funnel 930 may also contains lid clamp ring 934. Referring to FIG. 34c, lid clamp ring 934 contains sloped surface 943, end surface 987, and bottom surface 952. Sloped surface 943 may terminate at bottom surface 952, thus eliminating end surface 987. Funnel 930 also contains inner wall 931 and filter seal surface 945. The bottom of inner wall 931 may contain chamfer 922. Chamfer 922 increases the surface area of filter seal surface 945. Inner wall 931 is preferably tapered so that its diameter increases with height. The top portion 932 of inner wall 931 may contain a different taper than the lower portion of inner wall 931. Funnel 930 is shown circular in shape to match base 901. If base 901 is made from another shape such as square or rectangular, then funnel 930 must be made of the same shape to match base 901.

Figure 35A:
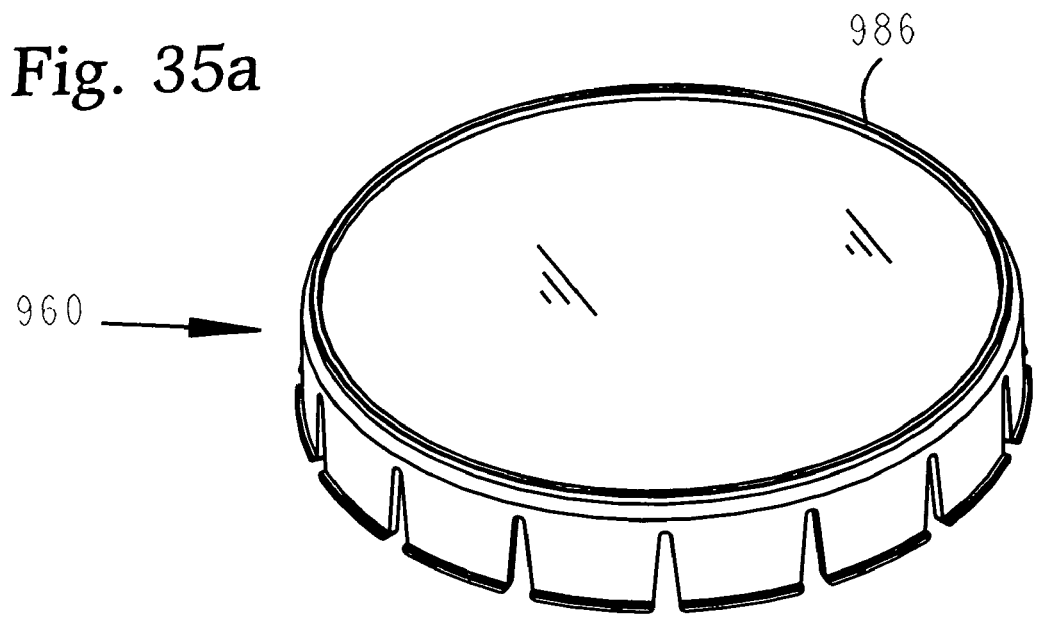
FIG. 35a is a top isometric view, of the lid component of the assembly depicted in FIG. 32.
Figure 35B:
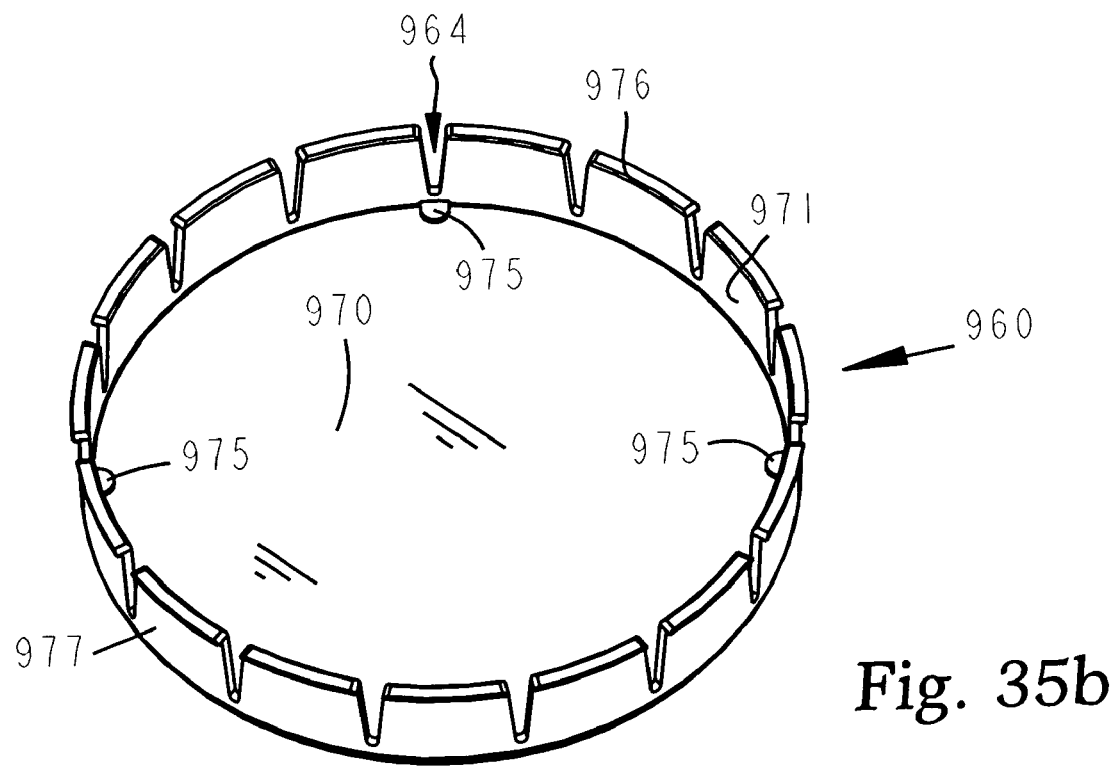
FIG. 35b is a bottom isometric view, of the lid component of the assembly depicted in FIG. 32.

Referring to FIGS. 35a and 35b, lid 960 is identical to lid 60 shown in FIG. 11 with the following exceptions. Lid 960 does not contain filter hold down ring 75 shown in FIG. 11, and lid 960 contains one or more lid vent tabs 975, while lid 60 does not contain one or more lid vent tabs 975. If base 901 is made from another shape such as square or rectangular, then lid 960 must be made of the same shape to match base 901.

Figure 36A:
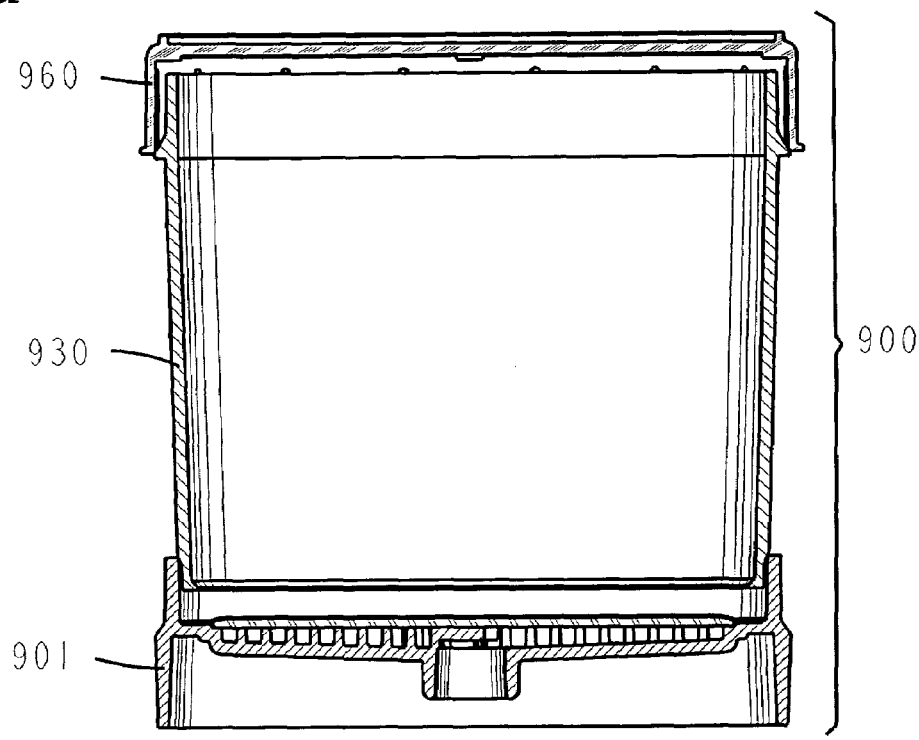
FIG. 36a is a cross-sectional view of the components that comprise the eighth embodiment of the filtration apparatus, shown in their pre-assembled state.

FIG. 36a shows assembly 900 in its pre-assembled state with base 901 containing absorbent pad 991, with filter element 990 non-releasably sealed to base 901, said seal being a heat seal, an ultrasonic seal, a solvent seal, a glue seal, or any other type of leak tight non-releasable seal. FIG. 36a shows absorbent pad 991 with a thickness greater than the height of pad well 927 of base 901 shown in FIG. 33a. Referring to FIG. 36c, the outer periphery of filter element 990 is sealed to base 901 with non-releasable seal 981. Because absorbent pad 991 is thicker than the height of pad well 927 of base 901 (as explained above), the outer periphery of absorbent pad 991 will be compressed by filter means 990. Compressed absorbent pad 991 exerts an upward force on filter means 990, thus keeping filter means 990 in tension and wrinkle free. Non-releasable seal 981 compresses absorbent pad 991 to keep filter means 990 in tension and wrinkle free, just as a compression seal does as described above with reference to FIG. 28.

Referring to FIG. 36a, and FIG. 36c, funnel 930 is placed onto base 901 in its pre-assembled state. If diameter D2 shown in FIG. 34b is less than the inside diameter of inner surface 905 of side wall 913 of base 901, and diameter D3 also shown in FIG. 34b, is greater than the inside diameter of inner surface 905 of side wall 913 of base 901, then the funnel can easily be positioned onto the base with step 936 of funnel 930 inserted into funnel well 926 of base 901 (shown in FIG. 33a) with chamfer 937 of funnel 930 resting on edge 927 of top outer wall 912 of base 901, with the central axis of funnel 930 aligned with the central axis of base 901. Base 901 must be made of a more pliable material than funnel 930 as will become evident later. For example, if base 901 is made from a material such as low density polyethylene, high density polyethylene, or polypropylene, then funnel 930 could be made from a clear material such as polystyrene, polycarbonate, or acrylic; or if base 901 is made from low density polyethylene, then funnel 930 could be made from materials such as polystyrene, polycarbonate, acrylic, or polypropylene, but the material combinations are not limited to those just listed.

Figure 36C:
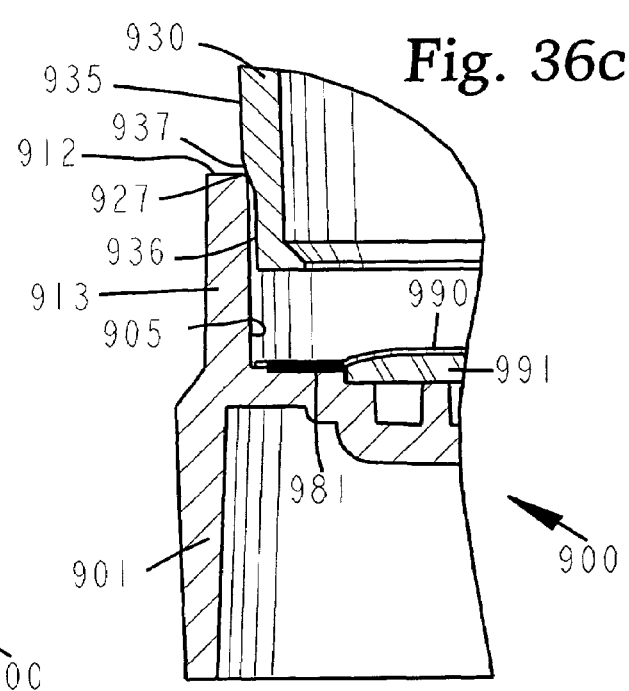
FIG. 36c is a partial cross-sectional view of the funnel and base depicted in FIG. 36a, shown in their pre-assembled state.
Figure 37A:
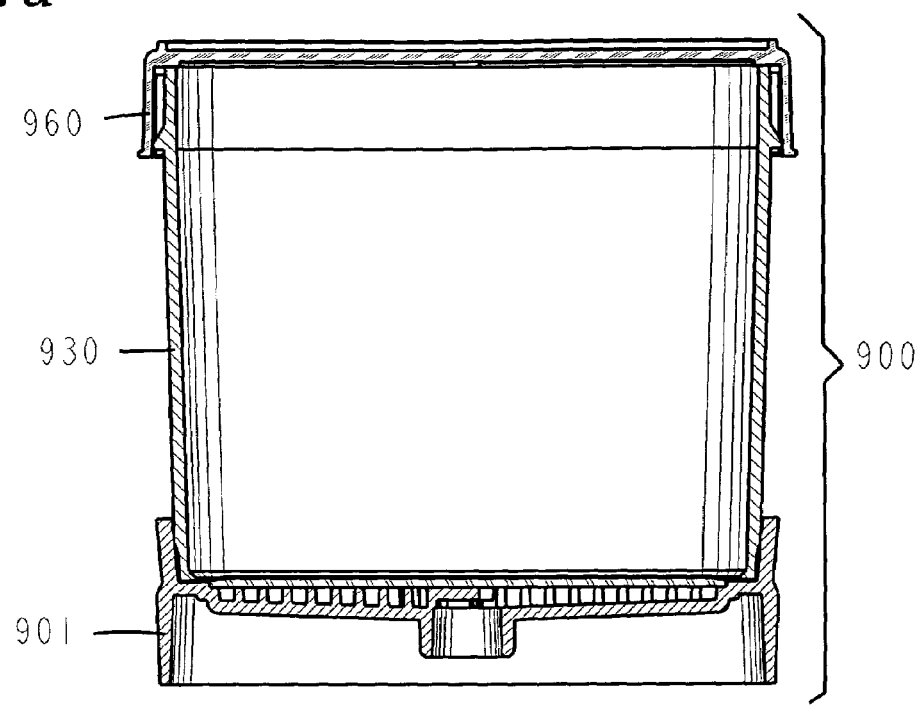
FIG. 37a is a cross-sectional view of the components that comprise the eighth embodiment of the filtration apparatus, shown in their assembled state.
Figure 37B:
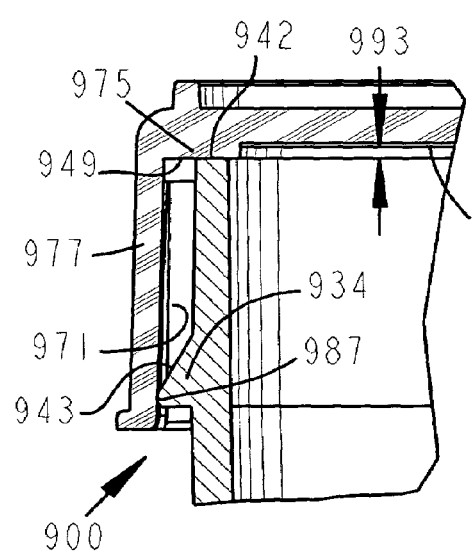
FIG. 37b is a partial cross-sectional view of the funnel and lid depicted in FIG. 37a, shown in their assembled state.
Figure 37C:
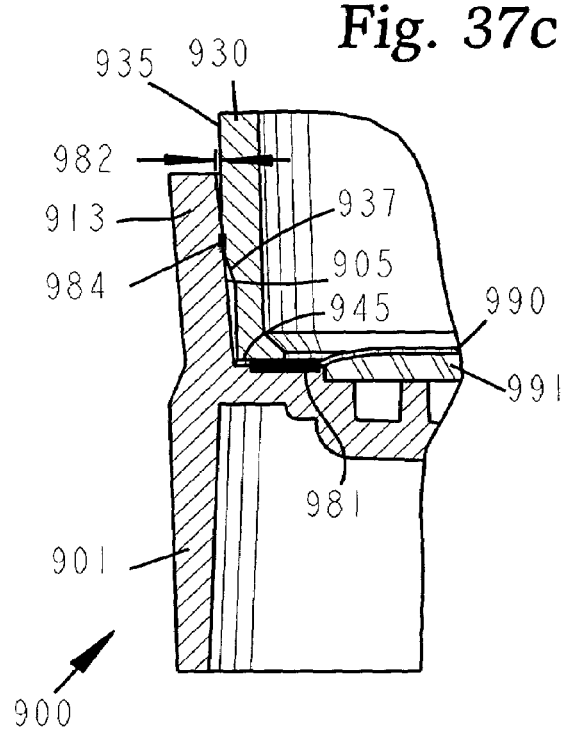
FIG. 37c is a partial cross-sectional view of the funnel and base depicted in FIG. 37a, shown in their assembled state.

FIG. 37a and FIG. 37c show the vacuum filtration apparatus (i.e. assembly 900) with funnel 930 releasably attached to base 901. This is accomplished by pushing funnel 930 down into base 901 from its pre-assembled state (shown in FIG. 36a and FIG. 36c) to its assembled state shown in FIG. 37a and FIG. 37c, thereby releasably attaching funnel 930 to base 901. With funnel 930 releasably attached to base 901, the bottom portion of outside wall 935 of funnel 930 forces side wall 913 of base 901 to deflect outward as shown in FIG. 37c, thereby creating an interference fit between the bottom portion of outside wall 935 of funnel 930 and inner surface 905 of side wall 913 of base 901. It is therefore necessary that the base be made of a material that is sufficiently pliable to allow the funnel to be inserted into the base as just described, and to deflect the side wall of the base outward. Although the interference fit between the bottom portion of outside wall 935 of funnel 930 and inner surface 905 of side wall 913 of base 901 will be adequate if the bottom portion of outside wall 935 of funnel 930 and inner surface 905 of side wall 913 of base 901 are made smooth, the strength of the interference fit will be improved if either the bottom portion of outside wall 935 of funnel 930 contains texture 933 or if the inner surface 905 of side wall 913 of base 901 contains texture 905a, or if both surfaces are textured. By making the base and funnel from the proper combination of materials, such as high density polyethylene for the base and styrene for the funnel, and by making the parts with the proper wall thickness, both the base and the funnel can be made to tolerances of ±0.004" while providing an adequate interference fit between the base and funnel, and also allowing the funnel to be fully inserted into the base so that the filter means can be reliably sealed with a compression seal between the filter seal surface of the base and the filter seal surface of the funnel.

If the angle of the bottom portion of outside wall 935 of funnel 930 is less than the deflected angle of side wall 913 of base 901, as shown in FIG. 37c, then the interference fit between the bottom portion of outside wall 935 of funnel 930 and inner surface 905 of side wall 913 of base 901 will occur only at region 984 at the lower part of outside wall 935 of funnel 930 that is inserted into base 901, and a gap 982 will exist between outside wall 935 of funnel 930 and the top part of inner surface 905 of side wall 913 of base 901 as shown in FIG. 37c.

Again referring to FIG. 37c, with funnel 930 fully seated into base 901, filter seal surface 945 of funnel 930 will press against the upstream surface of filter element 990. If it is desired to use a releasable seal between filter element 990 and base 901, non-releasable seal 981 could be eliminated, and filter element 990 could be releasably sealed with a compression seal between filter seal surface 945 of funnel 930, and filter seal surface 911 of base 901. If a releasable seal is used then it would be preferable that the inner edge of filter seal surface 945 of base 901 extend inward from its location shown in FIG. 37c to the inner edge of filter seal surface 911 of base 901 shown in FIG. 33a.

Figure 36B:
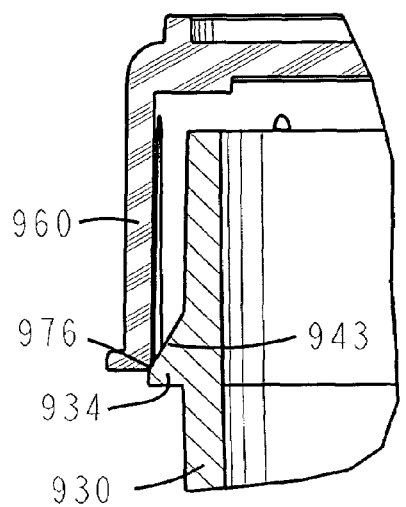
FIG. 36b is a partial cross-sectional view of the funnel and lid depicted in FIG. 36a, shown in their pre-assembled state.

Referring to FIG. 36a and FIG. 36b, lid 960 is shown in its pre-assembled state with edge 976 of lid 960 resting on surface 943 of lid clamp ring 934 of funnel 930. Surface 943 is preferably sloped as shown in FIG. 36b. Referring to FIG. 37a and FIG. 37b, lid 960 is shown in its assembled state releasably attached to funnel 930 with an interference fit between the bottom portion of inner surface 971 of lid 960 and outer edge 987 of lid clamp ring 934 of funnel 930, with surface 949 of one or more lid vent tabs 975 in contact with top wall 942 of funnel 930. Referring to FIG. 35b and FIG. 37b, with lid 960 in its assembled state on funnel 930, a gap 993 will exist between top wall 942 of funnel 930, and inside top surface 970 of lid 960 at all points on top wall 942 of funnel 930 that do not contact a lid vent tab 975 of lid 960. When lid 960 is properly positioned on funnel 930, all segments of outer wall 977 of lid 960 will contact lid clamp ring 934 of funnel 930, and will be bent out so that inner surface 971 of lid 960 is in contact with outer surface 987 of lid clamp ring 934. The height of inner surface 971 of outer wall 977 of lid 960 should be equal to or greater than the distance between top wall 942 of funnel 930 and the bottom surface 952 of lid clamp ring 934 of funnel 930, and equal to or greater than the distance between top outer wall 912 of base 901 and edge 959 of base 901 (shown in FIG. 38d). Because outer wall 977 of lid 960 is segmented by slots 964, lid clamp ring 934 of funnel 930 will force all segments to bend outward when lid 960 is positioned on the top of funnel 930. By increasing the number of slots 964 of lid 960, the length of each segment of outer wall 977 of lid 960 between adjacent slots 964 will be reduced. As the length of each segment is reduced, the curvature of each segment will be reduced, therefore, the flexibility of each segment will be increased, thus enabling the segment to bend outward without breaking, even when the lid 960 is made from stiff materials such as polystyrene, polycarbonate, or acrylic. As lid 960 is placed on funnel 930, surface 943 of lid clamp ring 934 initially contacts edge 976 of lid 960. Then as lid 960 is further pressed onto funnel 930, surface 943 causes inner surface 971 of outer wall 977 of lid 960 to bend outward gradually until lid 960 is fully seated on funnel 930, and inner surface 971 of outer wall 977 of lid 960 is in contact with end surface 987 of lid clamp ring 934. This arrangement of segmented outer wall 977 of lid 960 being press fitted onto lid clamp ring 934 of funnel 930 allows the funnel and lid to be made within a dimensional tolerance range of ±0.004" or greater, while providing an adequate interference fit between the lid and funnel to prevent accidental disengagement of the lid from the funnel, while also allowing the end user to place the lid onto the funnel, or to remove the lid from the funnel with one hand. The firmness of the interference fit can be adjusted by increasing the diameter of lid clamp ring 934 to increase the firmness, or by decreasing the diameter of lid clamp ring 934 to reduce the firmness, while keeping all other variables constant. The dimensional tolerance range of ±0.004" is well within the normal production range of dimensional tolerances. It should be noted that in some applications, such as counting particulates in a liquid sample the filtration apparatus may be used without the lid.

The end user will use the vacuum filtration apparatus shown as assembly 900 the same as assembly 100, assembly 200, and assembly 700 were used, as explained above. When the liquid to be tested is added to funnel 930, filter means 990 and absorbent pad 991 will be wetted. Because filter means 990 is very thin it will not swell appreciably in thickness, but will expand in diameter as it is wetted. Filter means 990 will wrinkle if an absorbent pad with a thickness approximately equal to the height of pad well 927 is used (as described in the previous embodiments of the present invention). This wrinkling will prevent portions of the downstream surface of filter means 990 from contacting the upstream surface of absorbent pad 991, which in turn will impede colony growth during the incubation cycle. However, when an absorbent pad that has a thickness that is substantially greater than the height of the pad well is used as shown in FIG. 37a and FIG. 37c (with a releasable or non-releasable seal between filter means 990 and base 901), filter means 990 will start out in tension (i.e. wrinkle free) when dry, and will remain in tension as absorbent pad 991 swells in thickness as it becomes wet. Because the thickness of absorbent pad 991 is sufficiently greater than the thickness of filter means 990, absorbent pad 991 will swell much more in thickness than filter means 990 will, thereby keeping filter means 990 in tension and wrinkle free when both the filter means and the absorbent pad are wet. Filter means 990 will remain in tension and wrinkle free throughout the filtration cycle while a vacuum is applied to outlet port 910, and remain in tension and wrinkle free when the filtration cycle is complete and outlet port 910 has been vented to atmosphere. This will assure uniform contact between the downstream surface of filter means 990 and the upstream surface of absorbent pad 991, thus assuring proper incubation of any colonies trapped on the upstream surface of filter means 990, during the incubation cycle. Absorbent pad 991 should be made thick enough to assure that filter means 990 remains wrinkle free throughout the filtration process, but not so thick to cause a brittle filter means to fracture in the region where it is compressed. If the liquid to be tested is water based it is preferable that filter means 990 and absorbent pad 991 be hydrophilic, however if the liquid to be tested is a solvent it is preferable that filter means 990 and absorbent pad 991 be hydrophobic.

Once the filtration step is complete, the user may proceed in one of four ways. The first option is to add a quantity of liquid growth media to funnel 930, and then to momentarily reapply the vacuum to outlet port 910 of base 901. The vacuum will draw the liquid growth media through filter means 990, and then into absorbent pad 991, with any excess liquid growth media going into the vacuum source. It is important that the user turn off the vacuum source and vent outlet port 910 as soon as the level of the liquid growth media in funnel 930 reaches the top surface of filter means 990, to prevent the vacuum source from sucking the liquid growth media out of absorbent pad 991. The pores of filter means 990 will remain wet with liquid growth media because the bubble point of filter means 990 exceeds the pressure differential applied to filter means 990 by the vacuum source (i.e. vacuum pump). If the vacuum is left on too long the liquid growth media will be sucked out of absorbent pad 991 because of its large nominal pore size, and the subsequent incubation step will give a false result. The user will now remove lid 960 from funnel 930, and then remove funnel 930 from base 901, and then discard funnel 930, and then place lid 960 onto base 901, and then insert outlet port plug 99 (shown in FIG. 15a) into outlet port 910 of base 901, and then place assembly 900a into an incubator, inverted as shown in FIG. 38b. If the filter means is sealed to the base with a releasable seal such as a compression seal, then filter hold down ring 75 of lid 60 (shown in FIG. 11) must be added to lid 960 to keep filter element 990 and absorbent pad 991 in place during incubation as described in the first embodiment of the present invention. After the proper incubation time assembly 900a will be removed from the incubator, and the top surface of filter means 990 will be examined for growth of bacteria colonies, yeast colonies, mold colonies, or the like. A grided filter as shown in FIG. 4 may be used to assist in colony counting.

Figure 38A:
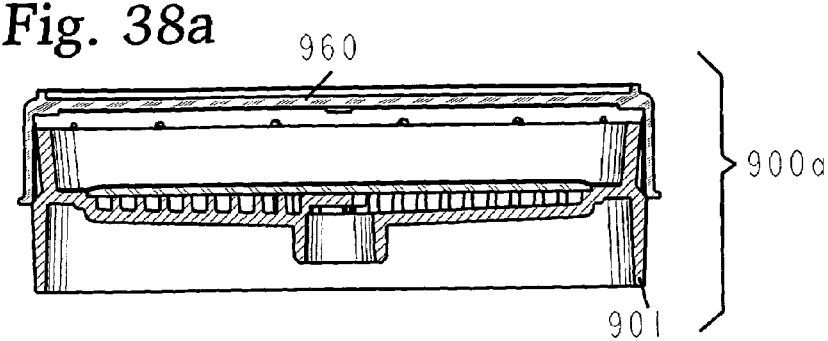
FIG. 38a is a cross-sectional view of the components that comprise the eighth embodiment of the filtration apparatus, constructed in accordance with the principles of the present invention, without the funnel section, with the remaining components pre-assembled in the petri dish mode.
Figure 38B:
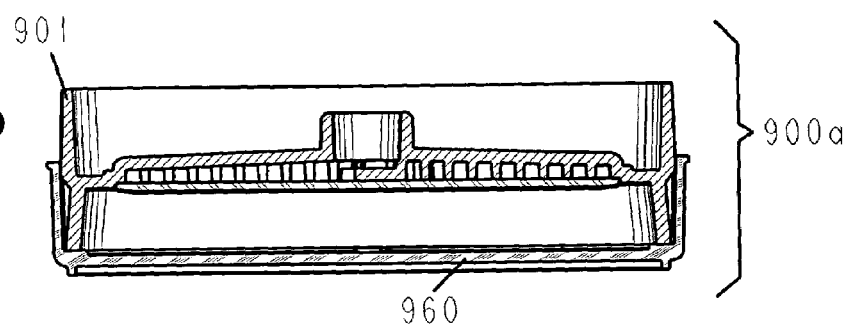
FIG. 38b is a cross-sectional view of the assembled components that comprise the eighth embodiment of the filtration apparatus, constructed in accordance with the principles of the present invention, without the funnel section, with the remaining components assembled in the petri dish mode, with said assembly shown inverted.
Figure 38C:
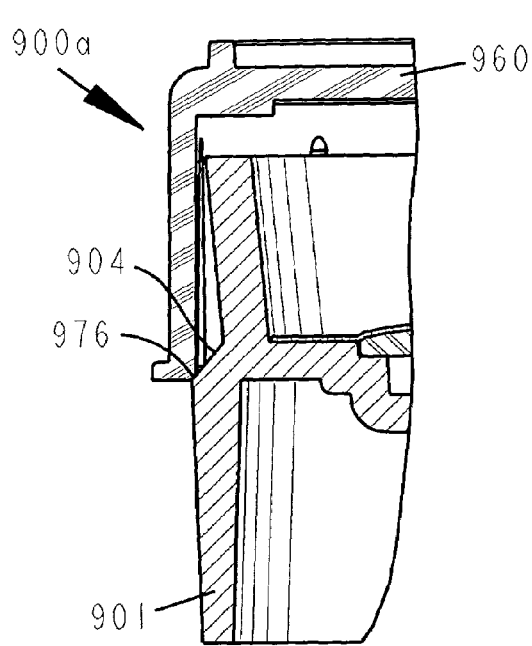
Figure 38D:
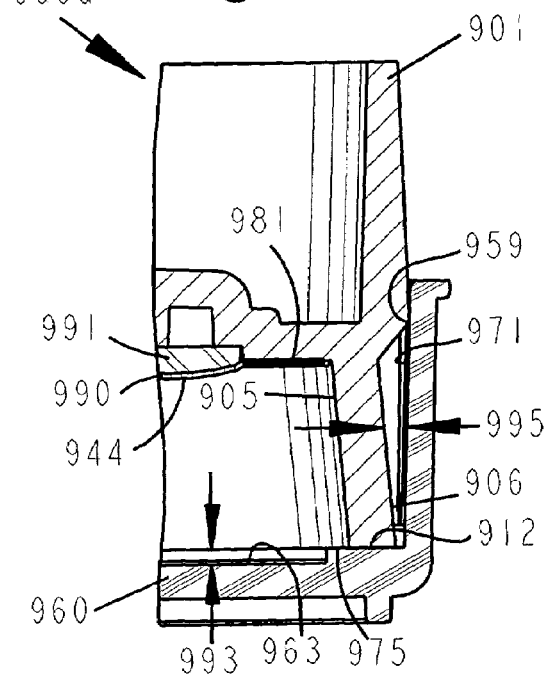
FIG. 38d is a partial cross-sectional view of the assembled components shown in FIG. 38b.

FIG. 38a and FIG. 38c show assembly 900a with lid 960 in its pre-assembled state on base 901 after funnel 930 has been removed from base 901. In the pre assembled state edge 976 of lid 960 rests on surface 904 of base 901. FIG. 38b and FIG. 38d show assembly 900a with lid 960 in its assembled state on base 901 after funnel 930 has been removed from base 901. Referring to FIG. 38d, in the assembled state the lower portion of inner surface 971 of lid 960 is releasably attached to edge 959 of base 901 with an interference fit. The outside diameter of edge 959 of base 901 must be greater than the deflected outside diameter of top outer wall 912 of base 901 as shown in FIG. 38d and greater than or equal to the outside diameter of end surface 987 of lid clamp ring 934 of funnel 930 (shown in FIG. 37b). Lid 960 will fit on base 901 the same as it fits on funnel 930. The nominal diameter of edge 959 of base 901, should be equal to or greater than the nominal diameter of end surface 987 of lid clamp ring 934 of funnel 930. Assuming that the dimensional tolerance range of base 901 and lid 960 are ±0.004", the above analysis of how lid 960 fits on funnel 930 applies to how lid 960 fits on base 901, with the diameter of edge 959 of base 901, corresponding to end surface 987 of lid clamp ring 934 of funnel 930, and with surface 904 of base 901, corresponding to surface 943 of lid clamp ring 934 of funnel 930.

Once the filtration step is complete the second option the user has is to remove lid 960 from funnel 930, and then remove funnel 930 from base 901, and then discard funnel 930, and then place lid 960 onto base 901 as described above, and then invert assembly 900a, as shown in FIG. 38b and FIG. 38d. If the filter means is sealed to the base with a releasable seal such as a compression seal, then filter hold down ring 75 of lid 60 (shown in FIG. 11) must be added to lid 960 to keep filter element 990 and absorbent pad 991 in place during incubation as described in the first embodiment of the present invention. At this point outlet port 910 of base 901 will be open (i.e. outlet port plug 99 shown in FIG. 15a will not be inserted in outlet port 910). A quantity of liquid growth media will now be dispensed into outlet port 910 of base 901. The liquid growth media will flow from outlet port 910 of base 901, into pad well 927 of base 901, and then into absorbent pad 991. Because the pores of filter means 990 remain wetted from the previous filtration step (because the bubble point pressure of filter means 990 is greater than the pressure differential that was applied to filter means 990 by the vacuum), air bubbles may get trapped in absorbent pad 991, as absorbent pad 991 is wetted with the liquid growth media. If an air bubble is trapped at the interface between filter means 990, and absorbent pad 991, the following incubation step may produce a false negative in the region of filter means 990 above said air bubble. The user will now insert outlet port plug 99 into outlet port 910 of base 901 as explained above, and then place assembly 900a into an incubator, inverted as shown in FIG. 38b. After the proper incubation time assembly 900a will be removed from the incubator, and the top surface of filter means 990 will be examined for growth of bacteria colonies, yeast colonies, or mold colonies. A grided filter as shown in FIG. 4 may be used to assist in colony counting.

If a compression seal is used to seal filter means 990 to base 901 with a releasable seal, then, once the filtration step is complete the third option the user has is to remove lid 960 from funnel 930, and then remove funnel 930 from base 901, and then discard funnel 930 and lid 960, and then remove filter means 990 from base 901 and place filter means 990 into a petri dish (known in the art) containing the desired growth media for incubation and colony counting.

In applications where it is not necessary to incubate, such as applications where particulates in the unfiltered liquid are being counted, the fourth option the user has is to remove the lid, and possibly remove the funnel and then count the particles trapped on the upstream surface of the filter means. In this type of application it may not be necessary to use a lid in the first place.

Referring to FIG. 35b and FIG. 38d, with the lid attached to the top of the base section, the lid, base section assembly 900a becomes a petri dish. The interior of this petri dish is in air flow communication with the outside atmosphere through a gap 993 between the top outer wall 912 of base 901 and the inside top surface 970 of lid 960, through a gap 995 between the outside surface 906 of side wall 913 of base 901 and the inner surface 971 of lid 960, through at least one slot in the side wall of lid 960. Gap 993 shown in FIG. 38d exists between top outer wall 912 of base 901, and inside top surface 970 of lid 960 at all points on top outer wall 912 of base 901 that do not contact a lid vent tab 975 of lid 960. Referring to FIG. 5, FIG. 11, and FIG. 15b, the gap between the top outer wall 12 of base 1 and the inside top surface 63 of lid 60 is one or more vent slots 3. Although lid 960 and lid 60 have a plurality of slots in their outer wall to make the outer wall flexible, a lid without these slots could be used, in which case at least one through hole could be used to place the gap between the outside wall of base and the inner surface of lid in air flow communication with the outside atmosphere. By placing the interior of petri dish (formed by the lid base assembly) in air flow communication with the outside atmosphere, condensation on the inside top surface of the lid will be minimized. Alternately if a lid without slots or a hole in the side wall of the lid is used, a groove in the inner surface of the side wall of the lid, or a groove in side wall of the base in contact with the inner surface of the side wall of the lid could be used to place gap 993 in air flow communication with the outside atmosphere.

Referring to FIG. 37*c*, if the draft angle of outside wall 935 of funnel 930 is less than the deflected angle of side wall 913 of base 901, then only the bottom part of the portion of outside wall 935 of funnel 930 that is inserted into base 901 will push against inner surface 905 of side wall 913 of base 901 causing side wall 913 of base 901 to deflect outward, thereby creating an interference fit between the bottom portion of outside wall 935 of funnel 930 and inner surface 905 of side wall 913 of base 901, only at region 984 at the lower part of the portion of outside wall 935 of funnel 930 that is inserted into base 901; and a gap 982 will exist between the upper part of inner surface 905 of side wall 913 of base 901 and outside wall 935 of funnel 930.

Figure 39A:
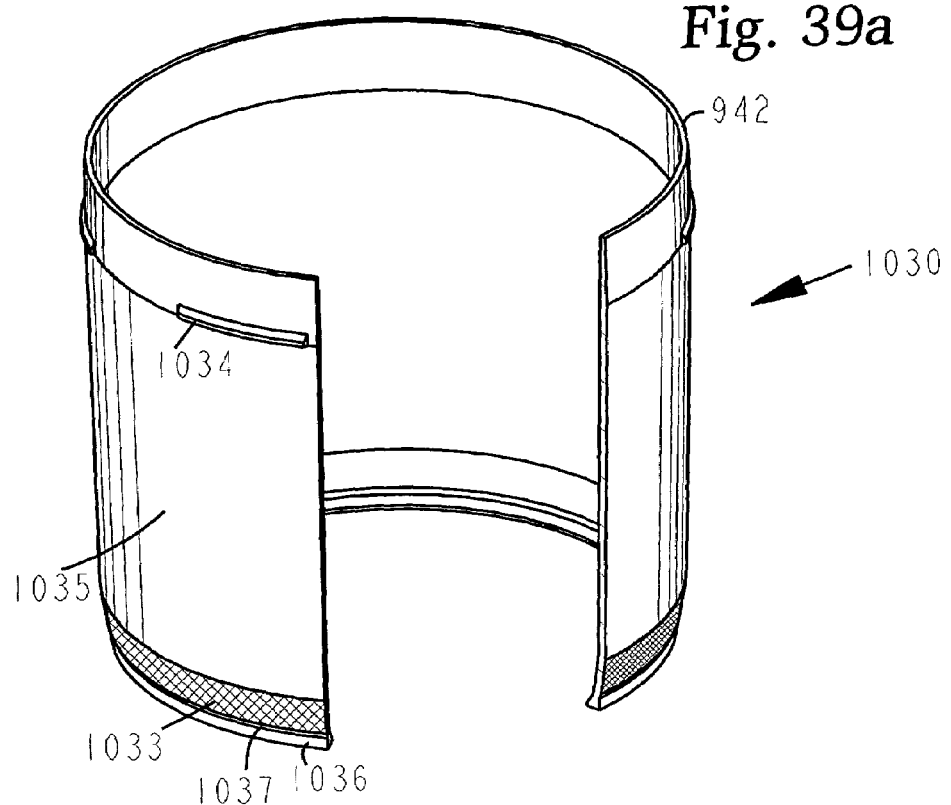
FIG. 39a is an isometric view, having portions thereof removed, of the funnel component of the assembly depicted in FIG. 40b.

A ninth embodiment of the filtration apparatus constructed in accordance with the principles of the present invention is shown in FIG. 39*a* through FIG. 41*d*. The ninth embodiment eliminates the gap 982 (shown in FIG. 37*c*) between the funnel and base. FIG. 40*b* shows the filtration apparatus as assembly 1000 in the assembled state containing base 1001, funnel 1030, and filter element 990. FIG. 40*a* shows assembly 1000 in the pre-assembled state. Base 1001 is identical to base 901 with the exception that pad well 927 has been eliminated, therefore the same reference numbers are used to designate the features of base 1001 as were used to designate the features of base 901. Base 901 could replace base 1001 in assembly 1000 in which case absorbent pad 991 would be added to assembly 1000. Assembly 1000 could also include lid 60 or lid 960. Referring to FIG. 39*a* and FIG. 39*b*, funnel 1030 is the same as funnel 930 with the following exceptions. The draft angle A1 of the bottom portion of outside wall 1035 is equal to or greater than the minimum deflected angle of inner surface 905 of side wall 913 of base 1001, and lid clamp ring 934 of funnel 930 is replaced with segmented lid clamp ring 1034 of funnel 1030. The draft angle of the upper part of outside wall 1035 of funnel 1030 may or may not be equal to that of the bottom portion of outside wall 1035. Preferably the bottom portion of outside wall 1035 that is inserted into the base contains textured surface 1033.

Figure 39B:
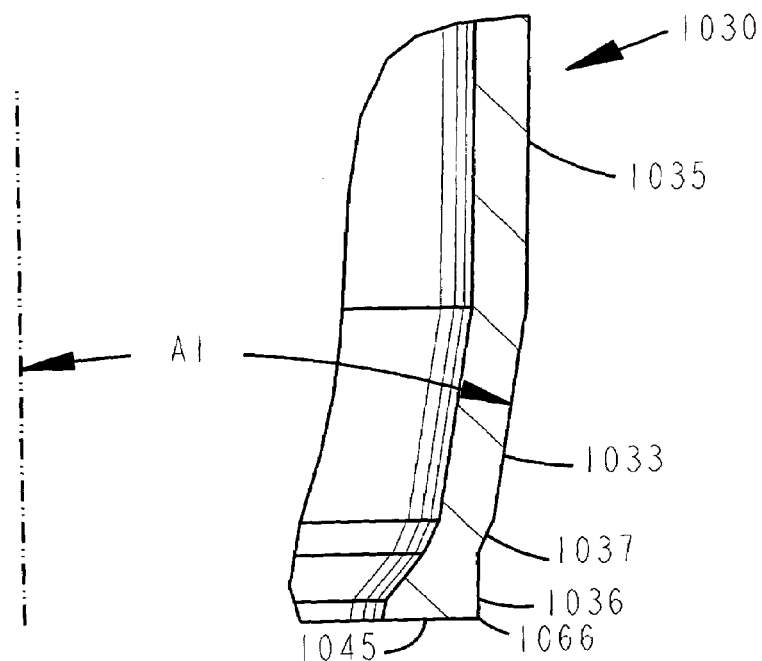
Figure 40A:
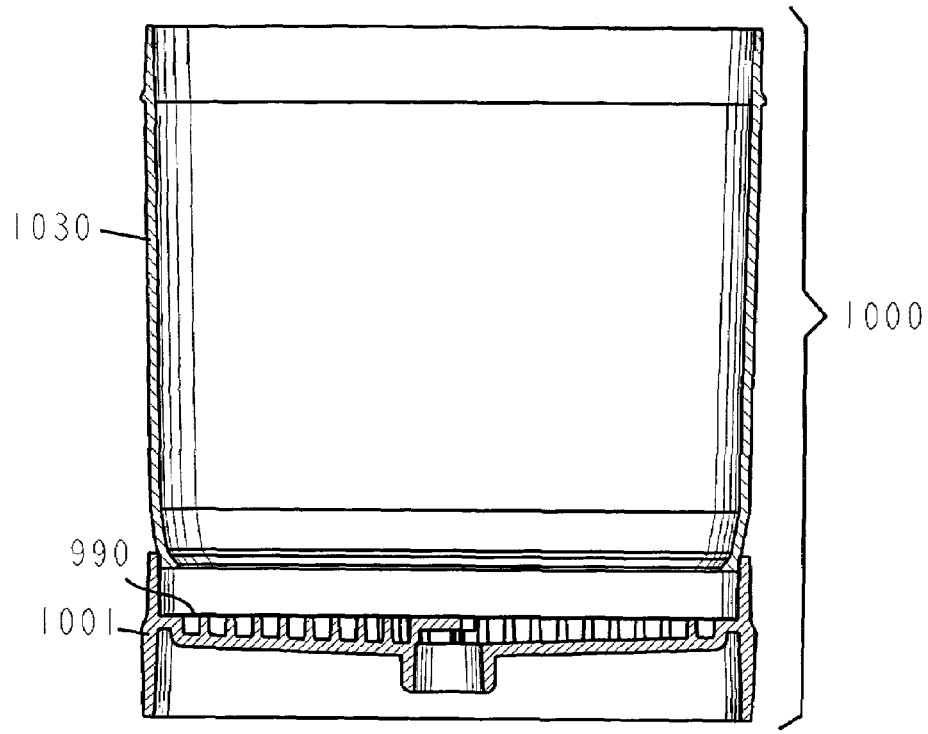
FIG. 40a is a cross-sectional view of the components that comprise the ninth embodiment of the filtration apparatus, constructed in accordance with the principles of the present invention, shown in their pre-assembled state.
Figure 40B:
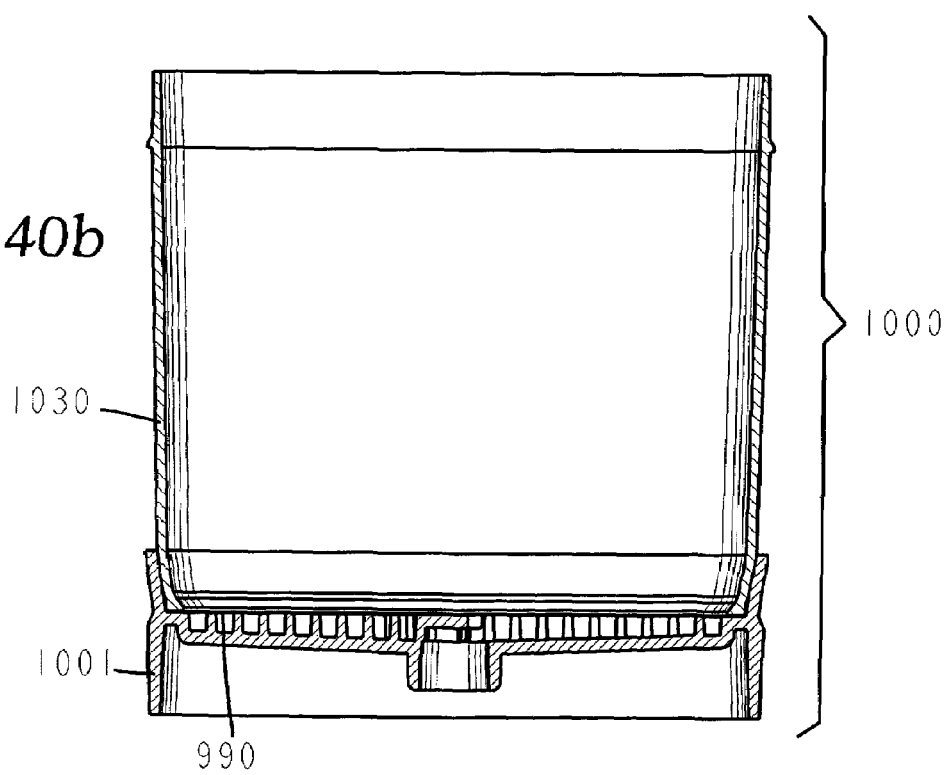
FIG. 40b is a cross-sectional view of the components that comprise the ninth embodiment of the filtration apparatus, constructed in accordance with the principles of the present invention, shown in their assembled state.
Figure 41A:
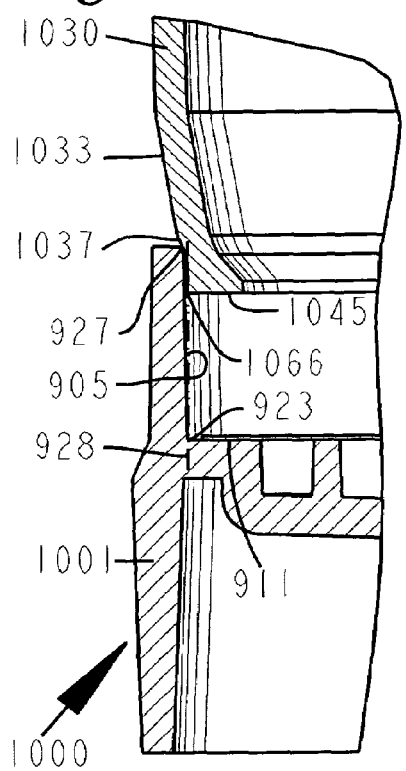
FIG. 41a is a partial cross-sectional view of a bottom portion of the pre-assembly depicted in FIG. 40a with maximum interference between the base and funnel.
Figure 41B:
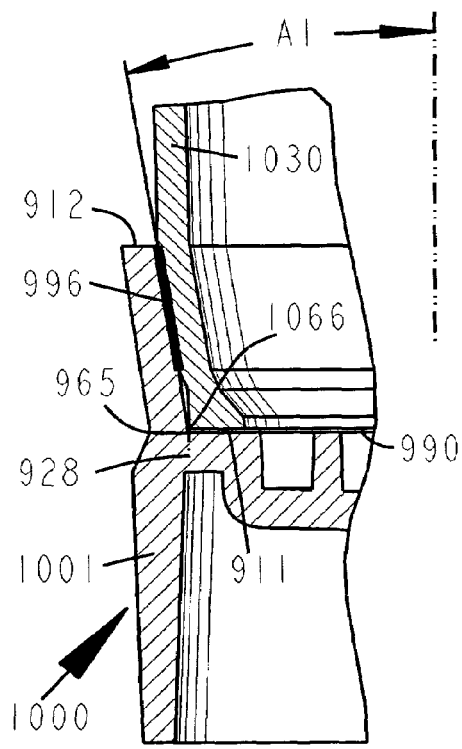
FIG. 41b is a partial cross-sectional view of a bottom portion of the assembly depicted in FIG. 40b with maximum interference between the base and funnel.

FIG. 41*a* shows the bottom portion of assembly 1000 in the pre-assembled state with the maximum interference between base 1001 and funnel 1030. Referring to FIG. 39*b* and FIG. 41*a*, with the maximum interference between base 1001 and funnel 1030, vertical centerline 928 intersects corner 923 of base 1001 between inner surface 905 of base 1001 and filter seal surface 911 of base 1001. Vertical centerline 928 also intersects corner 1066 of funnel 1030 between step 1036 of funnel 1030 and filter seal surface 1045 of funnel 1030. In the pre-assembled state chamfer 1037 of funnel 1030 rests on edge 927 of base 1001. FIG. 41*b* shows the bottom portion of assembly 1000 in the assembled state with the maximum interference between base 1001 and funnel 1030. By making draft angle A1 of the bottom portion of outside wall 1035 of funnel 1030 equal to or greater than the minimum deflected angle of inner surface 905 of side wall 913 of base 1001, the entire part of the bottom portion of outside wall 1035 of funnel 1030 below top outside wall 912 of base 1001 will contact inner surface 905 of side wall 913 of base 1001 to form an interference fit in region 996, thereby maximizing the surface area of the interference fit, thereby maximizing the strength of the interference fit. The minimum deflected angle of inner surface 905 of side wall 913 of base 1001 is defined as the minimum angle at which the entire part of the bottom portion of outside wall 1035 of funnel 1030 below top outside wall 912 of base 1001 will contact inner surface 905 of side wall 913 of base 1001 to form an interference fit in region 996. With funnel 1030 fully seated in base 1001 as shown in FIG. 41*b*, filter element 990 will be releasably sealed with a compression seal between filter seal surface 1045 of funnel 1030 and filter seal surface 911 of base 1001. Filter element 990 could alternately be sealed to base 1001 with a non-releasable seal such as a heat seal, an ultrasonic seal, a glue seal, a solvent seal, or any other type of leak tight non-releasable seal.

Figure 41C:
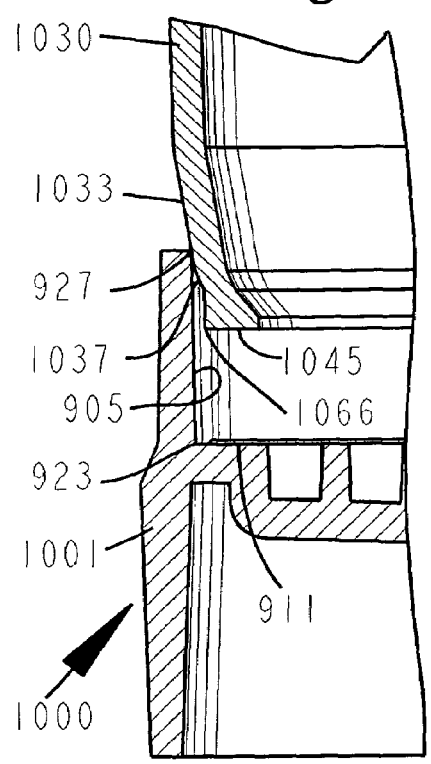
FIG. 41c is a partial cross-sectional view of a bottom portion of the pre-assembly depicted in FIG. 40a with minimum interference between the base and funnel.
Figure 41D:
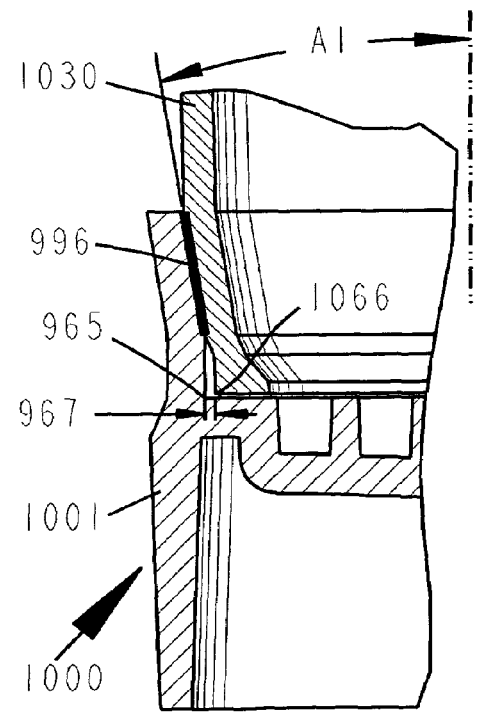
FIG. 41d is a partial cross-sectional view of a bottom portion of the assembly depicted in FIG. 40b with minimum interference between the base and funnel.

FIG. 41*c* shows the bottom portion of assembly 1000 in the pre-assembled state with the minimum interference between base 1001 and funnel 1030. Referring to FIG. 39*b* and FIG. 41*c*, with the minimum interference between base 1001 and funnel 1030, the bottom portion of outside wall 1035 of funnel 1030 rests on edge 927 of base 1001. FIG. 41*d* shows the bottom portion of assembly 1000 in the assembled state with the minimum interference between base 1001 and funnel 1030. By making draft angle A1 of the bottom portion of outside wall 1035 of funnel 1030 equal to or greater than the minimum deflected angle of inner surface 905 of side wall 913 of base 1001, the entire part of the bottom portion of outside wall 1035 below top outside wall 912 of base 1001 will contact inner surface 905 of side wall 913 of base 1001 to form an interference fit in region 996, thereby maximizing the surface area of the interference fit, thereby maximizing the strength of the interference fit. The only difference between assembly 1000 shown in FIG. 41*b* with maximum interference between base 1001 and funnel 1030, and assembly 1000 shown in FIG. 41*d* with minimum interference between base 1001 and funnel 1030 is the level relative to filter seal surface 911 of base 1001 at which side wall 913 of base 1001 begins to deflect outward, with minimum interference the level is higher. With funnel 1030 fully seated in base 1001 as shown in FIG. 41*d*, filter element 990 will be releasably sealed with a compression seal between filter seal surface 1045 of funnel 1030 and filter seal surface 911 of base 1001. Filter element 990 could alternately be sealed to base 1001 with a non-releasable seal such as a heat seal, an ultrasonic seal, a glue seal, a solvent seal, or any other type of leak tight non-releasable seal. Gap 967 shown in FIG. 41*d* is the maximum allowable tolerance on radius between base 1001 and funnel 1030 while still maintaining an interference fit over the entire region 996. The maximum tolerance on diameter as referred to above is two times the value of gap 967. The maximum allowable tolerance will be determined by the type of materials used, and by the thickness of side wall 913 of base 901 or of base 1001. By making the base and funnel from the proper combination of materials, such as high density polyethylene for the base and styrene for the funnel, and by making the parts with the proper wall thickness, both the base and the funnel can be made to tolerances of ±0.004" while providing an adequate interference fit between the base and funnel, and also allowing the funnel to be fully inserted into the base so that the filter means can be reliably sealed with a compression seal between the filter seal surface of the base and the filter seal surface of the funnel.

Figure 42A:
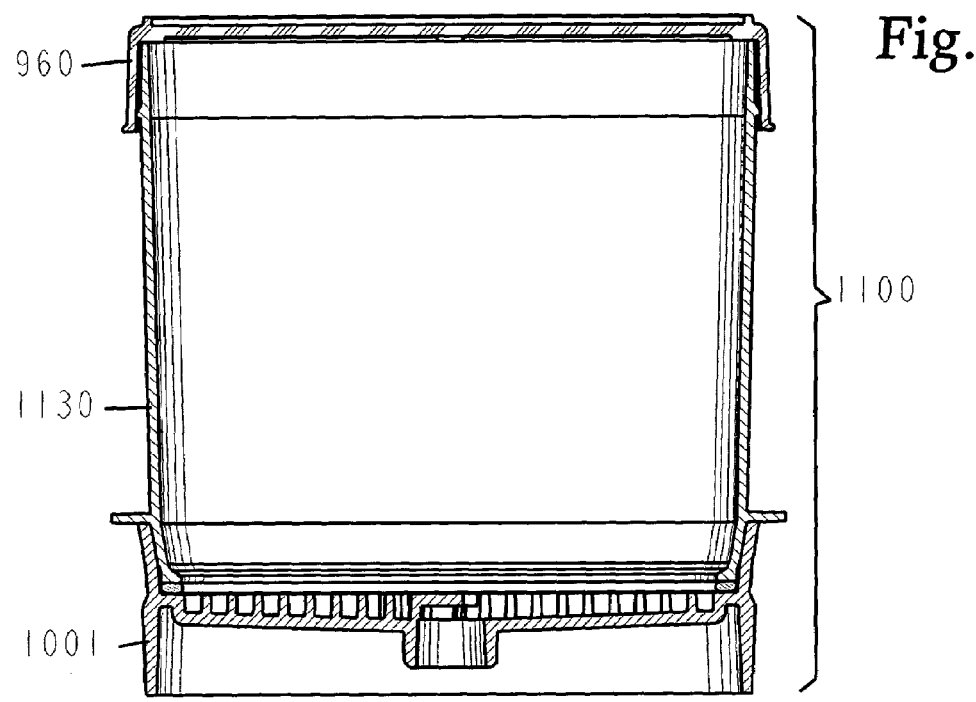
FIG. 42a is a cross-sectional view of the components that comprise the tenth embodiment of the filtration apparatus, constructed in accordance with the principles of the present invention, shown in their assembled state.
Figure 42B:
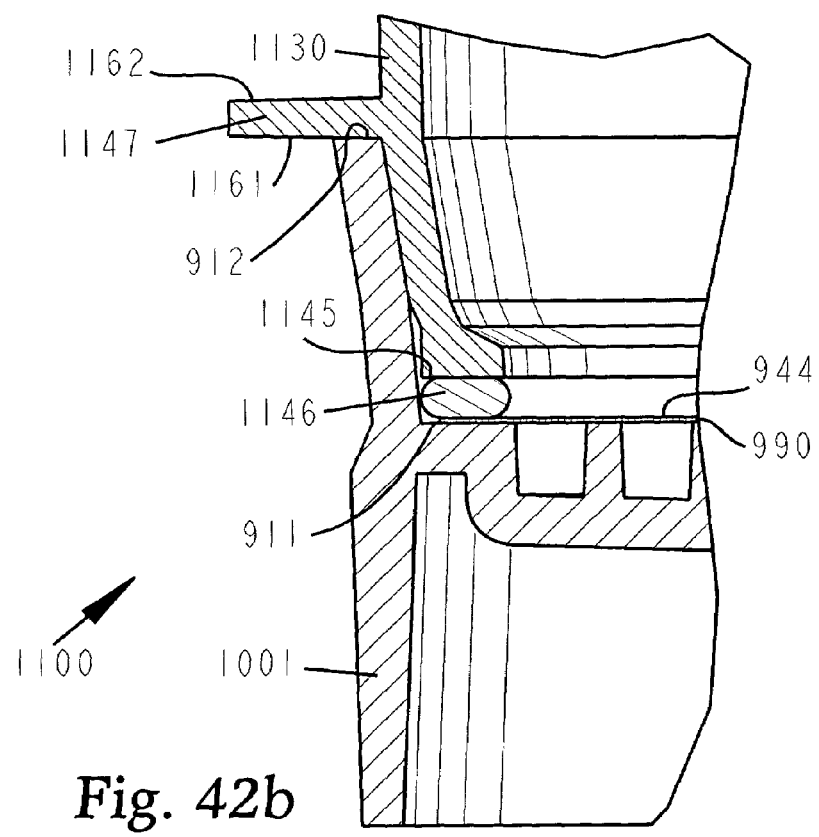

A tenth embodiment of the filtration apparatus constructed in accordance with the principles of the present invention, is shown in FIG. 42*a* and FIG. 42*b*. The filtration apparatus shown as assembly 1100 contains base 1001, funnel 1130, and lid 960. Base 1001 is identical to base 901 with the exception that pad well 927 has been eliminated, therefore the same reference numbers are used to designate the features of base 1001 as were used to designate the features of base 901. Base 901 could replace base 1001 in assembly 1100 in which case absorbent pad 991 would be added to assembly 1100.

Lid 60 could replace lid 960 in assembly 1100, or the lid could be eliminated. Funnel 1130 contains all of the features of funnel 1030 plus the additional feature of funnel stop 1147. Funnel 930 or funnel 1030 could replace funnel 1130 in assembly 1100. Assembly 1100 also contains pliable sealing means 1146. Pliable sealing means 1146 is preferably made from a compressible elastomeric material such as silicon rubber, Viton, Buna, or the like. However a compressible non-elastomeric such as Teflon or polyethylene or polypropylene could also be used. Pliable sealing means 1146 could be an o-ring, or a gasket. Pliable sealing means 1146 could also be an integral part of funnel 1130, in which case funnel 1130 would be molded from a first material such as styrene, acrylic, polycarbonate, or polypropylene, and pliable sealing means 1146 would be molded from a pliable material such as polyurethane.

Referring to FIG. 42*b*, with funnel 1130 fully seated in base 1001 with an interference fit between base 1001 and funnel 1130, as described above, and with pliable sealing means 1146 compressed, filter element 990 is sealed to base 1001 with a releasable compression seal between filter seal surface 911 of base 1001 and the bottom surface of pliable sealing means 1146, and the bottom surface 1145 of funnel 1130 is sealed with a releasable compression seal to the top surface of pliable sealing means 1146. With bottom surface 1161 of funnel stop 1147 resting on top outer wall 912 of base 1001, funnel stop 1147 prevents pliable sealing means 1146 from being over compressed. However, funnel stop 1147 could be eliminated. Because pliable sealing means 1146 can be made from a soft material that will flex in all directions, this type of seal is better suited to seal very thin non-compressible filter means such as polycarbonate microporous membrane filters.

Pliable sealing means 1146 could also be used in any of the previous embodiments of the present invention, or with any filtration apparatus in which the funnel is attached to the base with an interference fit. For example pliable sealing means could be used in the first embodiment (shown in FIG. 12 and FIG. 13*b*) with pliable sealing means 1146 being placed between bottom surface 44 of funnel 30 and the upstream surface of filter means 90. Pliable sealing means 1146 could also be used in the first embodiment if integral flexible filter seal 38 were eliminated from funnel 30, in which case pliable sealing means 1146 would be placed between the bottom surface of funnel 30 and the upstream surface of filter means 90. Pliable sealing means could also be used in the sixth embodiment (shown in FIG. 24 through FIG. 28) as just described with pliable sealing means 1146 being centered by the three or more filter centering tabs 779. In the sixth embodiment pliable sealing means 1146 will push down on the outer periphery of filter means 90, so that the outer periphery of filter means 90 is sealed with a compression seal between bottom surface of pliable sealing means 1146, and filter seal surface 711 of base 701. Because absorbent pad 791 is substantially thicker than the height of pad well 27 of base 701 (as explained above), the outer periphery of absorbent pad 791 will be compressed by filter means 90 which is in turn will be compressed by pliable sealing means 1146. Compressed absorbent pad 791 exerts an upward force on filter means 90, thus keeping filter means 90 in tension and wrinkle free.

Figure 43A:
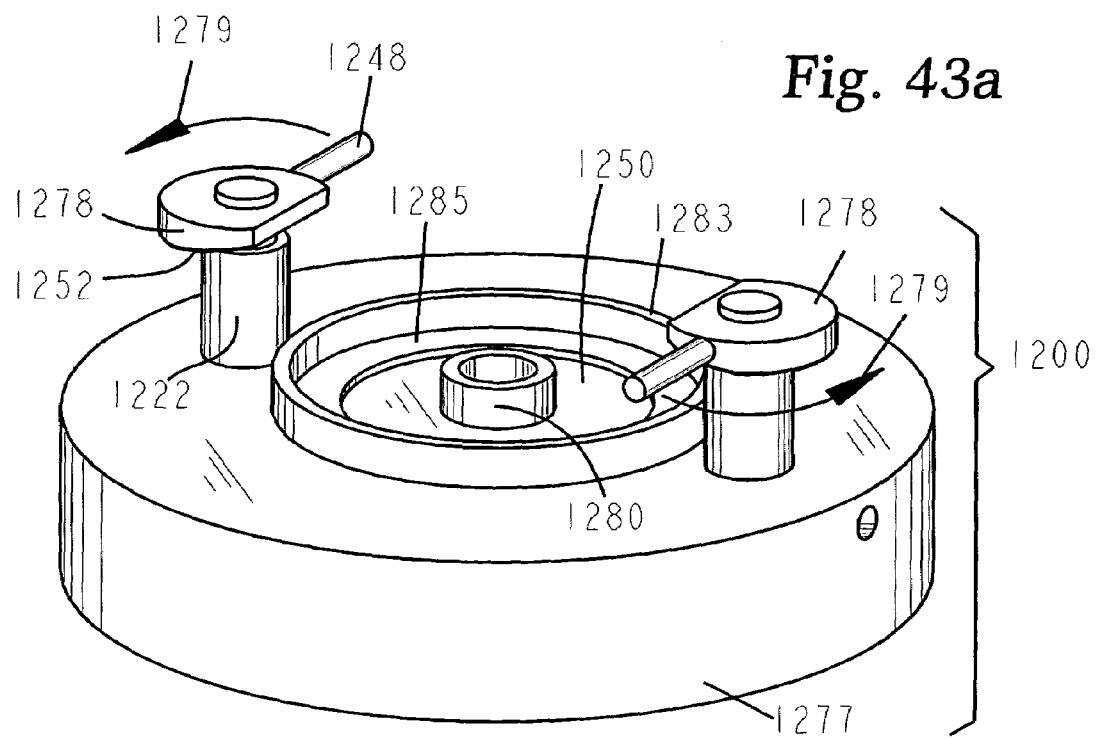
FIG. 43a is an isometric view of a vacuum base to be used with a vacuum filtration apparatus.
Figure 43B:
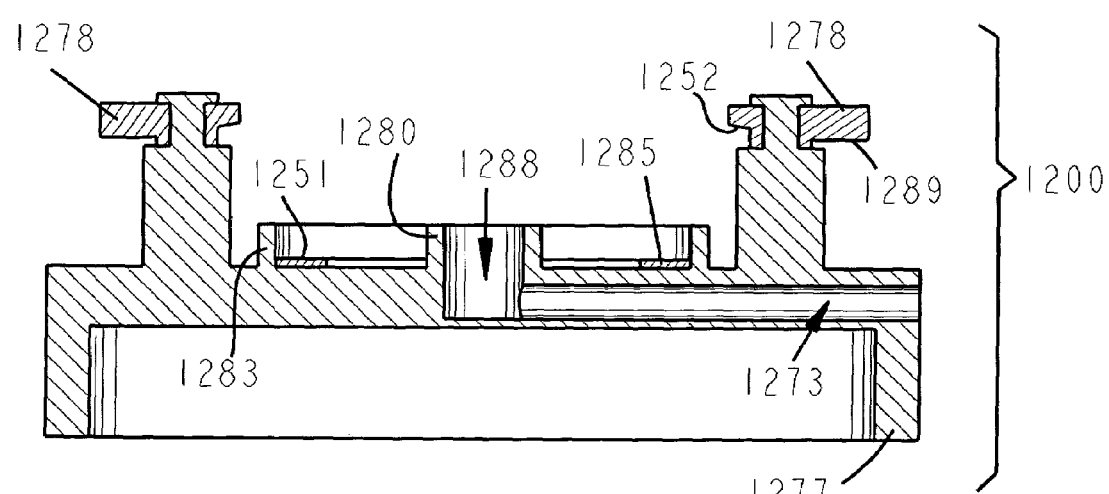

FIG. 43*a* and FIG. 43*b* show vacuum base assembly 1200 to be used with a vacuum filtration apparatus as will be explained below. Vacuum base assembly 1200 contains a vacuum base 1277. Vacuum base 1277 contains vacuum port 1288 disposed in wall 1250 of vacuum base 1277, with wall 1250 disposed substantially horizontal. Vacuum port 1288 is located on wall 1250 of vacuum base 1277 so that the central axis of the outlet port of the vacuum filtration apparatus that is to be used with vacuum base 1277 substantially aligns with the central axis of vacuum port 1288 of vacuum base 1277 when the vacuum filtration apparatus is aligned with and disposed above vacuum base 1277. Vacuum base 1277 may contain boss 1280, in which case vacuum port 1288 extends through boss 1280 as shown in FIG. 43*b*. Vacuum base 1277 may also contain a means to locate the vacuum filtration apparatus on vacuum base 1277 shown as ring 1283 disposed on wall 1250 of vacuum base 1277. Another means could be used to locate the vacuum filtration apparatus on vacuum base 1277 such as a segmented ring or a pattern of pins. Vacuum base 1277 also contains a means to place vacuum port 1288 in fluid flow communication with a vacuum source shown as port 1273. Alternately port 1273 could be eliminated and vacuum port 1288 could be placed in fluid flow communication with a vacuum source by a length of tubing. Vacuum base assembly 1200 may contain a means to clamp the vacuum filtration apparatus to vacuum base 1277 shown as a pair of cams 1278 which are supported by cam supports 1222, and rotateable by handles 1248. Cams 1278 are shown in the open or non-clamping position in FIG. 43*a* and FIG. 43*b*. Cams 1278 contain sloped surface 1252. If cams 1278 are rotated by handles 1248, 180° in the direction shown by arrows 1279 cams 1278 will be in the closed or clamping position with clamp surfaces 1289 of cams 1278 positioned toward the center of vacuum base 1277. Vacuum base assembly 1200 also contains gasket 1285 disposed on wall 1250 of vacuum base 1277, with the bottom surface of gasket 1285 in contact with wall 1250 of vacuum base 1277, and with vacuum port 1288 located within the inner periphery of gasket 1285 as shown in FIG. 43*b*.

Figure 44A:
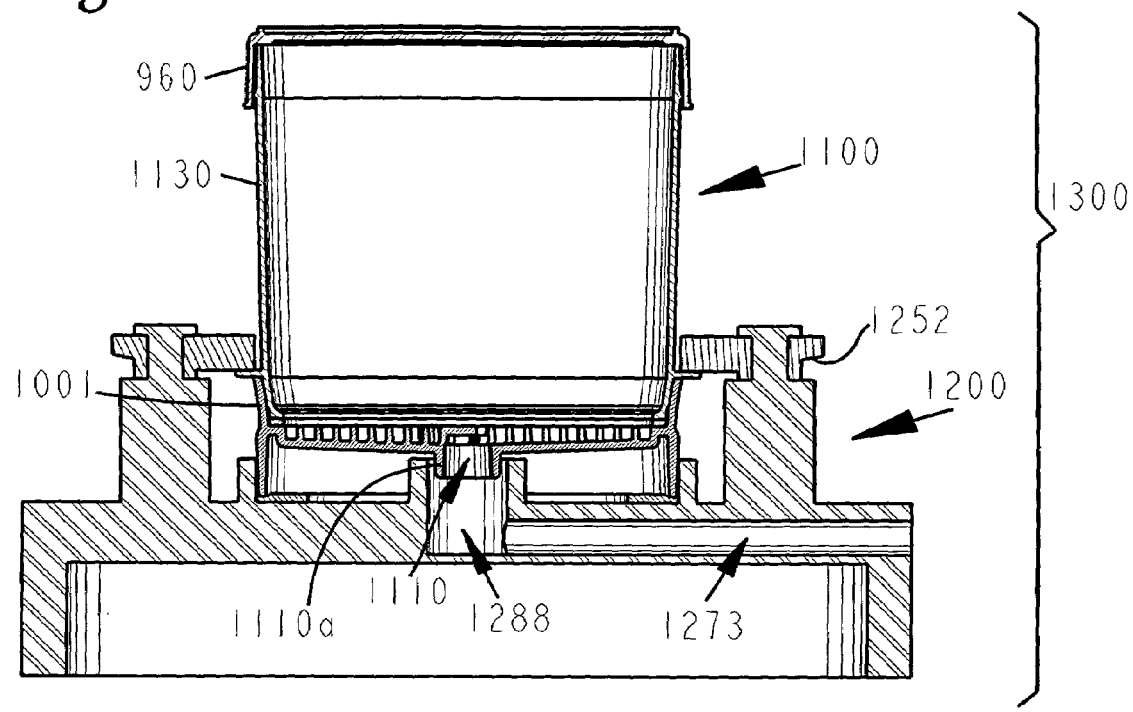
FIG. 44a is a cross-sectional view of an assembly containing the vacuum base depicted in FIG. 43a, with a vacuum filtration apparatus shown in FIG. 42a positioned on the vacuum base.
Figure 44B:
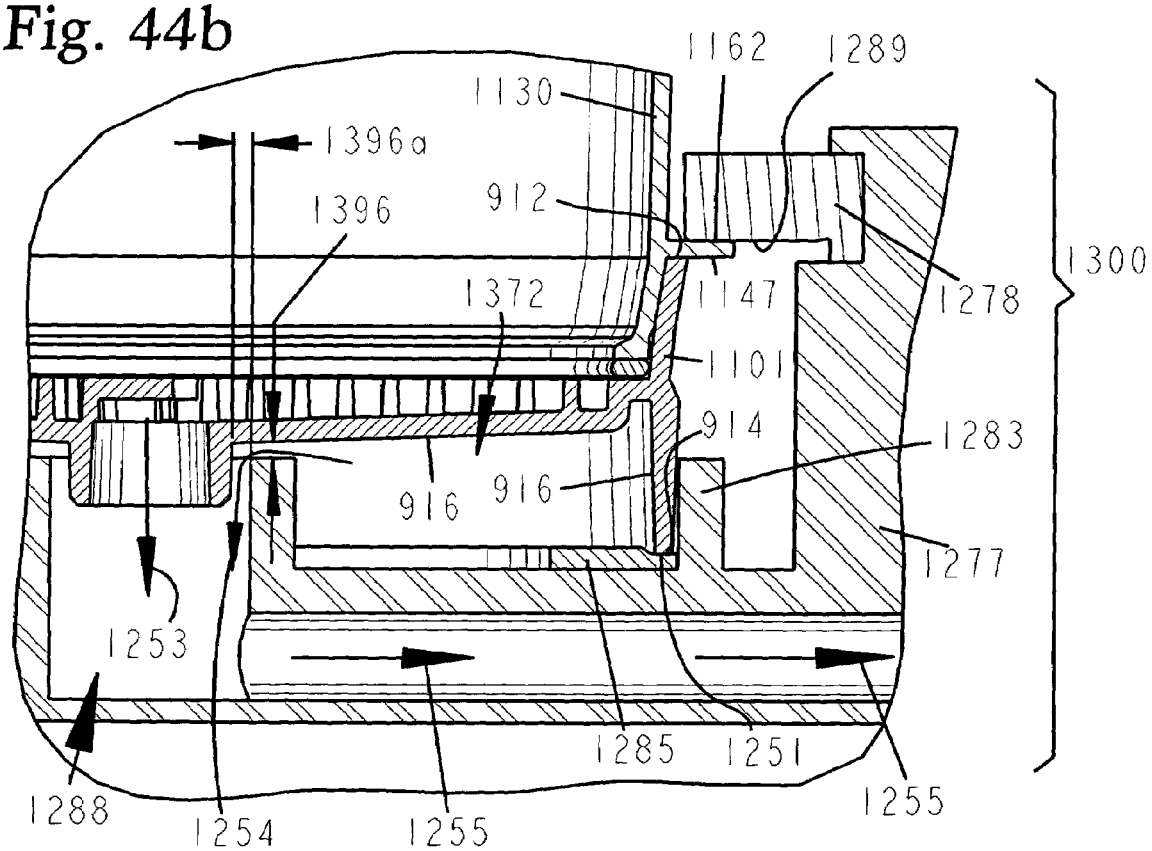

FIG. 44*a* and FIG. 44*b* show filtration system 1300 containing vacuum base assembly 1200 and assembly 1100 described above. Vacuum base assembly 1200 is used in the following way. The user will place a vacuum filtration apparatus (shown in FIG. 44*a* and FIG. 44*b* as assembly 1100) onto vacuum base assembly 1200 so that the central axis of the outlet port of the base (shown as outlet port 1110) of the vacuum filtration apparatus is substantially aligned with the central axis of vacuum port 1288 of the vacuum base assembly, and with a portion of the bottom outside wall of the base of the vacuum filtration apparatus (shown as surface 914 of bottom outside wall 916 of base 1101) disposed above, and in contact with, the top surface 1251 of gasket 1285 of vacuum base assembly 1200, with the bottom of the outlet port of the vacuum filtration apparatus preferably disposed below the top of the vacuum port 1288 of vacuum base assembly 1200. A means to locate the vacuum filtration apparatus on vacuum base 1277 (shown as ring 1283) may be used to align the vacuum filtration apparatus on the vacuum base assembly. With the vacuum filtration apparatus positioned on vacuum base assembly 1200 as just described with cams 1278 in the open position, the gasket will seal the void between the portion of the bottom outside wall of the base of the vacuum filtration apparatus (shown as bottom outside wall 916) that is not in contact with gasket 1285, and wall 1250 of vacuum base assembly 1200. With the vacuum filtration apparatus positioned on vacuum base assembly 1200 as just described, a means must be provided to place the void between the portion of the bottom outside wall of the base of the vacuum filtration apparatus (shown as bottom outside wall 916) that is not in contact with gasket 1285, and the wall 1250 of vacuum base assembly 1200 (shown as chamber 1372) in fluid flow communication with vacuum port 1288 of vacuum base 1277. This means is shown as gap 1396 between the top wall of boss 1280 of vacuum base 1277 and the bottom outside wall of the base of the vacuum filtration apparatus, and gap 1396a between the inside wall of vacuum port 1288 and the outside wall of the outlet port of the vacuum filtration apparatus.

With the vacuum filtration apparatus positioned on vacuum base assembly 1200 as described in the previous paragraph and shown in FIG. 44a and FIG. 44b (with cams 1278 in the open position as shown in FIG. 43a), the user will now remove the lid (shown as lid 960) from the vacuum filtration apparatus (shown as assembly 1100) and add a quantity of liquid to be filtered to the funnel (shown as funnel 1130). The lid will then be placed back onto the funnel. Vacuum will now be applied to vacuum port 1288 of vacuum base 1277 via port 1273. Although the downward force created by the weight of the liquid in the funnel should be sufficient to make a seal between the bottom surface of the base of the filtration apparatus (shown as surface 914 of base 1101) and the top surface 1251 of gasket 1285 the user may have to momentarily press down on the filtration apparatus to make this seal. The vacuum applied to vacuum port 1288 of vacuum base 1277 will draw the air out of chamber 1372 via gap 1396 and gap 1396a as shown by arrow 1254 in FIG. 44b, thereby evacuating chamber 1372. Once chamber 1372 becomes evacuated, the vacuum in chamber 1372 will apply a downward force to the base of the vacuum filtration apparatus, thereby keeping the outer edge of gasket 1285 compressed and thereby maintaining a seal between the bottom outside wall of the base of the filtration apparatus and the top surface 1251 of gasket 1285. The vacuum in vacuum port 1288 will also create a vacuum on the downstream side of the filter means in the vacuum filtration apparatus by drawing air out of the outlet port of the base of the vacuum filtration apparatus (shown as outlet port 1110 in FIG. 44a) as described above with respect to the operation of the first embodiment of the present invention. The vacuum on the downstream side of the filter means of the vacuum filtration apparatus will suck unfiltered liquid from the funnel of the vacuum filtration apparatus, through the filter means of the vacuum filtration apparatus, into the outlet port of the vacuum filtration apparatus, into vacuum port 1288 of vacuum base 1277 (shown by arrow 1253), into the vacuum source via port 1273 of vacuum base 1277 (shown by arrows 1255). To assure that all of the filtered liquid flows from the outlet port of the vacuum filtration apparatus into vacuum port 1288 of vacuum base 1277, the bottom of the outlet port of the vacuum filtration apparatus must be below the top of vacuum port 1288 of vacuum base 1277 as shown in FIG. 44b. Because the bubble point of the filter means of the vacuum filtration apparatus will exceed the pressure differential applied to the filter means by the vacuum source (as described above in the descriptions of the prior embodiments), the vacuum on the downstream side of the filter means will be maintained after all of the unfiltered liquid in the funnel has been drawn through the filter means. Additional liquid may be added to the funnel either while liquid is being filtered or after all of the initial batch of liquid in the funnel has been filtered. Once all of the liquid that is desired to be filtered, has been filtered, the user will vent vacuum port 1288 of vacuum base 1277 to atmosphere, thereby venting chamber 1372 (shown in FIG. 44b), and thereby venting the downstream volume of the vacuum filtration apparatus. Once chamber 1372 has been vented to atmosphere, the downward force that was applied to the base of the vacuum filtration apparatus by the vacuum will be removed, and the vacuum filtration apparatus will rest on gasket 1285 held down by gravity only. The vacuum filtration apparatus can now be easily removed from vacuum base assembly 1200.

Vacuum base assembly 1200 can be used as described above with any of the embodiments of the present invention that are described above. Vacuum base assembly 1200 can also be used with any vacuum filtration apparatus containing:
  (a) a funnel for receiving unfiltered liquid,
  (b) a base disposed below the funnel:
    (i) the base containing an outlet port that can be aligned with vacuum port 1288 of vacuum base assembly 1200 as described above,
    (ii) the base further containing a surface that can be sealed to gasket 1285 of vacuum base assembly 1200 so that the outlet port of the base is located within the inner periphery of the gasket seal, as just described,
  (c) a filter means sealed to the vacuum filtration apparatus, thereby preventing unfiltered liquid from flowing between the filter means and the outlet port of the base.

Vacuum base assembly 1200 can also be used with any vacuum filtration apparatus containing:
  (a) a base that includes an integral funnel:
    (i) the base containing an outlet port that can be aligned with vacuum port 1288 of vacuum base assembly 1200 as described above,
    (ii) the base further containing a surface that can be sealed to gasket 1285 of vacuum base assembly 1200 so that the outlet port of the base is located within the inner periphery of the gasket seal, as just described,
  (b) a filter means sealed to the vacuum filtration apparatus, thereby preventing unfiltered liquid from flowing between the filter means and the outlet port of the base.

Vacuum base assembly 1200 can also be used as follows. The user will place a vacuum filtration apparatus (shown in FIG. 44a and FIG. 44b as assembly 1100) onto vacuum base assembly 1200 so that the central axis of the outlet port of the base (shown as outlet port 1110) of the vacuum filtration apparatus is substantially aligned with the central axis of vacuum port 1288 of the vacuum base assembly, and with a portion of the bottom outside wall of the base of the vacuum filtration apparatus (shown as surface 914 of bottom outside wall 916 of base 1101) disposed above, and in contact with, the top surface 1251 of gasket 1285 of vacuum base assembly 1200, with the bottom of the outlet port of the vacuum filtration apparatus preferably disposed below the top of the vacuum port 1288 of vacuum base assembly 1200. The user will then releasably clamp the vacuum filtration apparatus to vacuum base assembly 1200 using a clamping means (shown as cams 1278). Other clamping means such as a pair of latches could also be used. FIG. 44a and FIG. 44b show assembly 1100 releasably clamped to vacuum base assembly with cams 1278 in the closed or clamping position. Cams 1278 are designed so that with assembly 1100 positioned on vacuum base assembly 1200 as just described, sloped surface 1252 of cams 1278 will contact top surface 1162 of funnel stop 1147 as cams 1278 are rotated from the open position to the closed position as described above. When cams 1278 have been rotated to the closed position as shown in FIG. 44b, clamp surface 1289 of cams 1278 will contact top surface 1162 of funnel stop 1147 of funnel 1130, with cams 1278 exerting a downward force on funnel stop 1147, thereby assuring that funnel 1130 is fully seated in base 1101, and that surface 914 of bottom outside wall 916 of base 1101 is in contact with top surface 1251 of gasket 1285 with gasket 1285 compressed as shown in FIG. 44b. If the vacuum filtration apparatus does not contain a funnel stop as shown in FIG. 44b, a clamping means could be used that pushes down on the top of the funnel, or on the top of the lid of the vacuum filtration apparatus. Alternately, if the vacuum filtration apparatus does not contain a funnel stop a clamping means could be used that pushes down on the top outer wall of the base (shown as top outer wall 912).

The disadvantage of pushing down on the top outer wall of the base is that although the bottom surface of the base (shown as surface 914 of bottom wall 916 of base 1101) will be pushed against the top surface 1251 of gasket 1285 of vacuum base assembly 1200 as shown in FIG. 44b, the clamping means will not assure that the funnel is fully seated in the base. Alternately gasket 1285 could be eliminated, and an o-ring or gasket could be located in gap 1396 so that the downward force of the cams would compress the o-ring or gasket between surface 916 of base 1101 and the top surface of boss 1280. Preferably the o-ring or gasket including gasket 1285 is made from a relatively soft non-elastomeric material such as polyethylene or polypropylene, and more preferably from an elastomeric material such as rubber, silicon rubber, Buna, or Viton, but is not limited to these materials. The important feature of the gasket or o-ring is that it provide a seal between the two surfaces that the gasket is located between. Alternately the gasket or o-ring could be eliminated and gap 1396a could also be eliminated, and boss 1110a of base 1101 could be press-fitted into vacuum port 1288. The apparatus will work as long as a means is provided to apply a vacuum to outlet port 1110 of base 1101. For example, if outlet port 1110 is connected to vacuum via a length of tubing and gasket 1285 is eliminated so that surface 914 of base 1101 contacts wall 1250 of vacuum base assembly 1200; the cams 1278 pressing down on funnel stop 1147 will assure that the funnel 1130 is fully seated in base 1101, thereby assuring that the filter element is sealed to the filtration apparatus with a leak tight releasable seal.

With the vacuum filtration apparatus positioned and clamped on vacuum base assembly 1200 as just described, a means must be provided to place chamber 1372 in air flow communication with vacuum port 1288 of vacuum base 1277. This means is shown as gap 1396 between the top wall of boss 1280 of vacuum base 1277 and the bottom wall of the base of the vacuum filtration apparatus, and gap 1396a between the inside wall of vacuum port 1288 and the outside wall of the outlet port of the vacuum filtration apparatus. With the vacuum filtration apparatus positioned on vacuum base assembly 1200 as just described, the bottom of the outlet port of the vacuum filtration apparatus is preferably positioned below the top of vacuum port 1288 of vacuum base assembly 1200 as shown in FIG. 44b. Alternately ring 1283 of vacuum base 1277 could be eliminated, and the vacuum filtration apparatus could be aligned to vacuum base assembly 1200 by aligning the outlet port of the vacuum filtration apparatus with vacuum port 1288 of vacuum base 1277, in which case gasket 1285 could be properly positioned on vacuum base 1277 by the user, or gasket 1285 could have a smaller inside diameter and be positioned by the outside wall of boss 1280 of vacuum base 1277. Any of the alternate means described in the previous paragraph of applying a vacuum to outlet port 1110 could also be used such as placing a gasket in gap 1396.

With the vacuum filtration apparatus positioned and clamped on vacuum base assembly 1200 as described in the previous two paragraphs and shown in FIG. 44a and FIG. 44b, the user will now remove the lid (shown as lid 960) from the vacuum filtration apparatus (shown as assembly 1100) and add a quantity of liquid to be filtered to the funnel (shown as funnel 1130). The lid will then be placed back onto the funnel. Vacuum will now be applied to vacuum port 1288 of vacuum base 1277 via port 1273. Because the clamping means assures a good seal between the bottom surface of the base of the vacuum filtration apparatus and the top surface 1251 of gasket 1285 of the vacuum base assembly 1200 the user will not have to momentarily press down on the filtration apparatus to make a seal between the bottom surface of the base of the filtration apparatus (shown as surface 914 of base 1101) and the top surface 1251 of gasket 1285. The vacuum applied to vacuum port 1288 of vacuum base 1277 will draw the air out of chamber 1372 via gap 1396 and gap 1396a as shown by arrow 1254 in FIG. 44b. Once chamber 1372 becomes evacuated, the vacuum in chamber 1372 will apply a downward force to the base of the vacuum filtration apparatus, this downward force may compress gasket 1285 further than it is already compressed by the clamping means (depending on the downward force applied by the clamping means), thereby maintaining the seal between the bottom surface of the base of the filtration apparatus and the top surface 1251 of gasket 1285. Alternately if gasket 1285 is eliminated, and a gasket is positioned in gap 1396, the downward force applied to the filtration apparatus by the vacuum will be minimal, and if outlet port 1110 is connected to the vacuum source by a length of tubing the downward force applied to the filtration apparatus by the vacuum will be zero. The vacuum in vacuum port 1288 will also create a vacuum on the downstream side of the filter means in the vacuum filtration apparatus by drawing air out of the base of the vacuum filtration apparatus via the outlet port of the base of the vacuum filtration apparatus (shown as outlet port 1110 in FIG. 44a) as described above with respect to the operation of the first embodiment of the present invention. The vacuum on the downstream side of the filter means of the vacuum filtration apparatus will suck unfiltered liquid from the funnel of the vacuum filtration apparatus, through the filter means of the vacuum filtration apparatus, into the outlet port of the vacuum filtration apparatus, into vacuum port 1288 of vacuum base 1277 (shown by arrow 1253), into the vacuum source via port 1273 of vacuum base 1277 (shown by arrows 1255). To assure that all of the filtered liquid flows from the outlet port of the vacuum filtration apparatus into vacuum port 1288 of vacuum base 1277, the bottom of the outlet port of the vacuum filtration apparatus must be below the top of vacuum port 1288 of vacuum base 1277 as shown in FIG. 44b. Because the bubble point of the filter means of the vacuum filtration apparatus will exceed the pressure differential applied to the filter means by the vacuum source (as described above in the descriptions of the prior embodiments), the vacuum on the downstream side of the filter means will be maintained after all of the unfiltered liquid in the funnel has been drawn through the filter means. Additional liquid may be added to the funnel either while liquid is being filtered or after all of the initial batch of liquid in the funnel has been filtered. Once all of the liquid that is desired to be filtered has been filtered, the user will vent vacuum port 1288 of vacuum base 1277 to atmosphere, thereby venting chamber 1372 (shown in FIG. 44b), and thereby venting the downstream volume of the vacuum filtration apparatus. Once chamber 1372 has been vented to atmosphere, the downward force that was applied to the base of the vacuum filtration apparatus by the vacuum will be removed, and the vacuum filtration apparatus will rest on gasket 1285 held down by gravity and the clamping means of vacuum base assembly 1200. After releasing the clamping means from the vacuum filtration apparatus, the vacuum filtration apparatus can be easily removed from vacuum base assembly 1200.

Vacuum base assembly 1200 with the appropriate clamping means can be used as just described with any of the embodiments of the present invention that are described above. Vacuum base assembly 1200 with the appropriate clamping means can also be used with any vacuum filtration apparatus containing an outlet port that can be aligned with vacuum port 1288 of vacuum base assembly 1200, and a base that can be sealed to gasket 1285 of vacuum base assembly 1200 as just described.

Alternately the vacuum base assembly 1200 could be used as just described, with vacuum port 1288 connected to a container for collecting filtered fluid, with vacuum port 1288 kept at atmospheric pressure, and with a positive pressure applied to the interior of the funnel, thereby applying a differential pressure between the outlet port of the base and the space above the liquid in the funnel, thereby forcing the liquid in the funnel through the filter means into the outlet of the filtration apparatus, into vacuum port 1288.

Figure 45A:
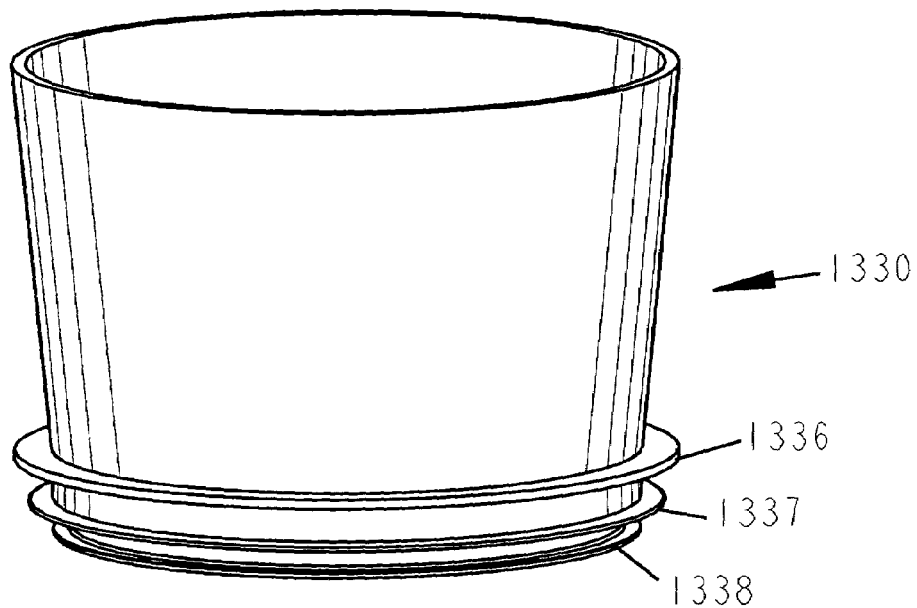
Figure 46A:
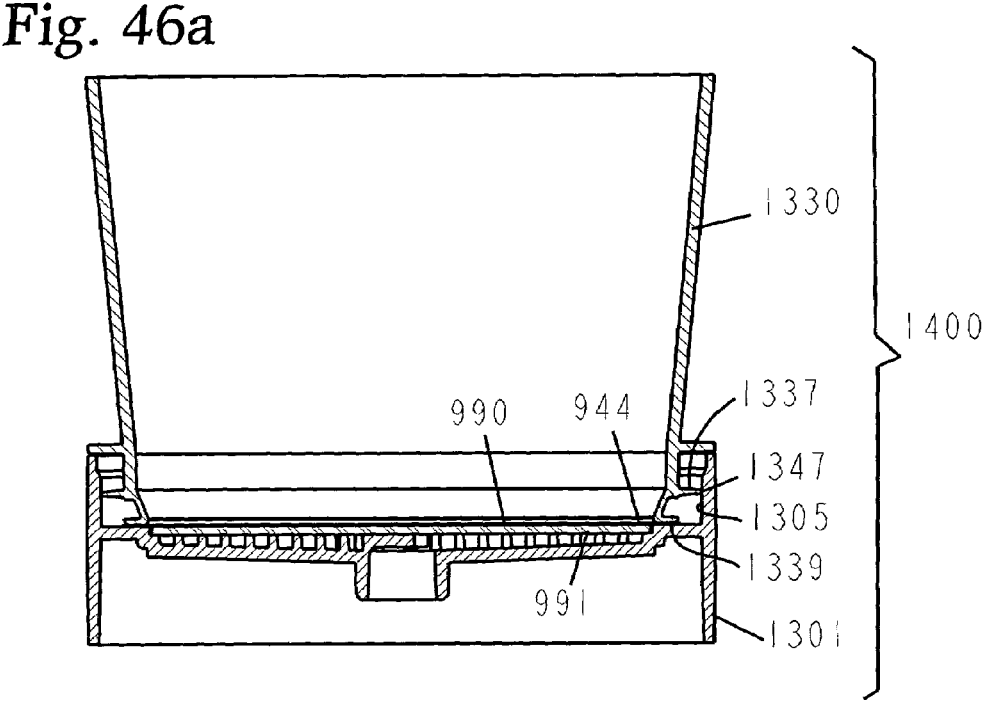

Referring to FIG. 45a funnel 1330 is the same as funnel 730 (shown in FIG. 25, FIG. 27, and FIG. 28) with the following exceptions. Funnel 1330 does not contain funnel centering tabs 792 or lid clamp tabs 734, and funnel 1330 contains integral flexible filter seal 1338 which is similar to integral flexible filter seal 838a shown in FIG. 30. Assembly 1400 shown in FIG. 46a contains base 1301, funnel 1330, filter means 990, and absorbent pad 991. FIG. 46a shows funnel 1330 in assembly 1400, releasably attached to the base 1301 with an interference fit between end wall 1347 of one or more integral flexible funnel seal rings 1337 of funnel 1330 and inside wall 1305 of base 1301. Funnel 1330 of assembly 1400 could be replaced with any funnel that contains one or more integral flexible funnel seal rings, and base 1301 could be replaced with any base to which a funnel containing one or more integral flexible seal rings can be releasably attached. Funnel 1330 must be made from a material which is flexible enough to allow the outside opposite faces of the funnel to be squeezed as described in the following paragraph. Suitable materials include but are not limited to, low density polyethylene, high density polyethylene, and polypropylene.

Figure 45B:
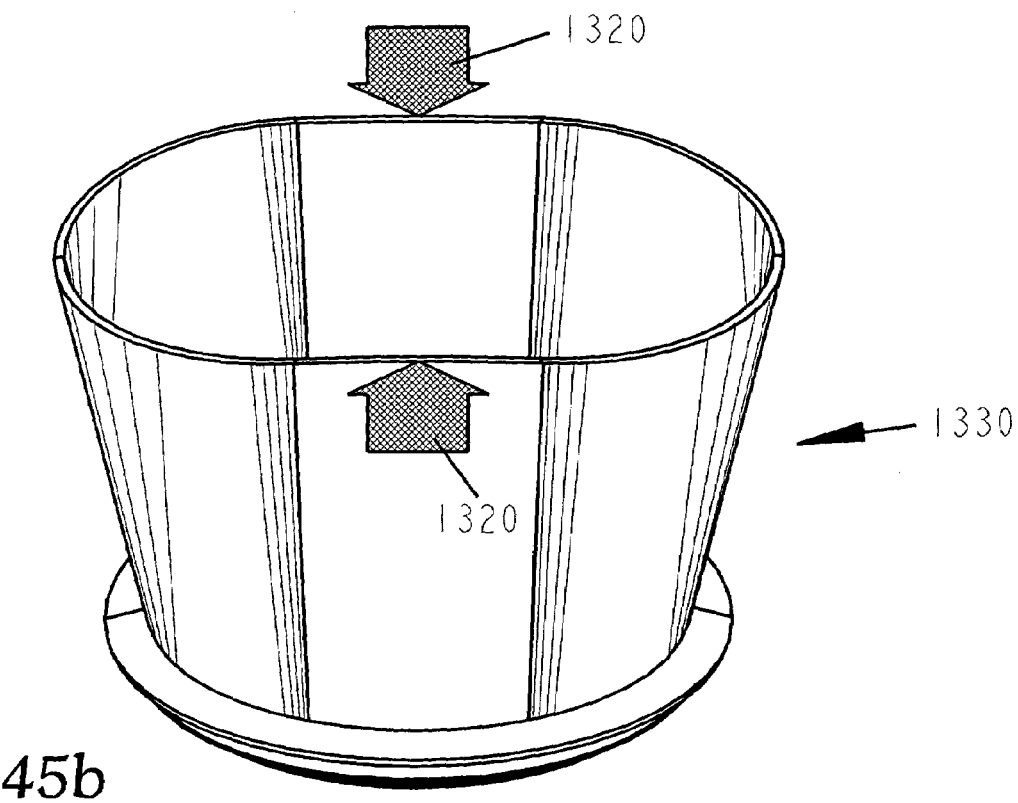
FIG. 45b is an isometric view of the funnel depicted in FIG. 45a, shown in the squeezed position.
Figure 46B:
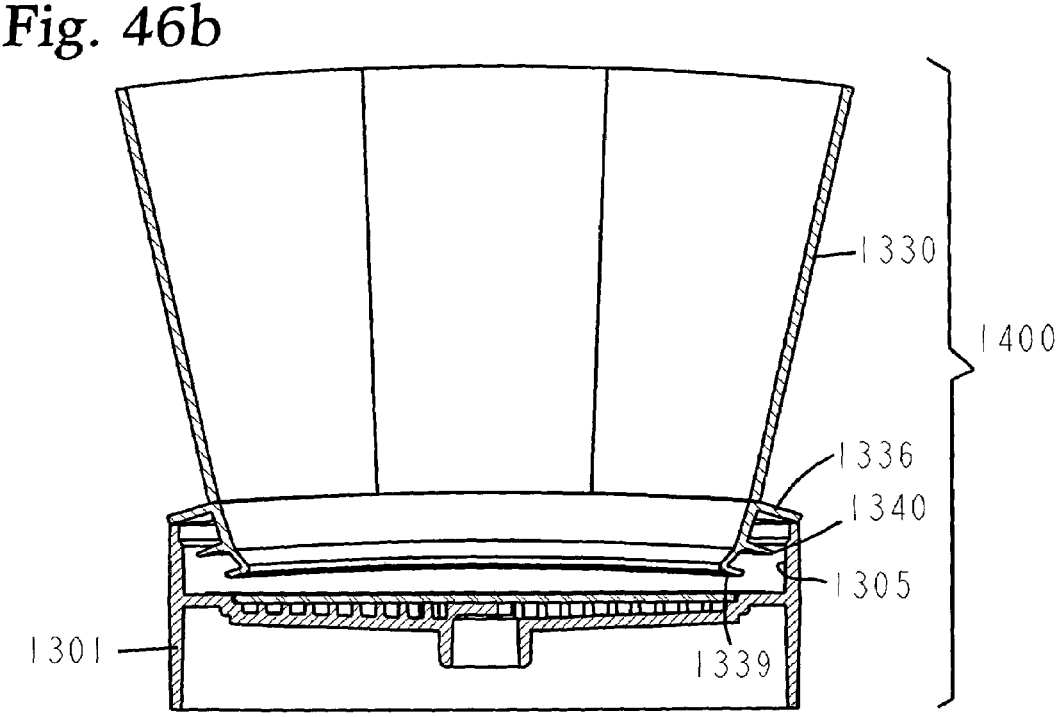
FIG. 46b is a cross-sectional view of the vacuum filtration apparatus shown in FIG. 46a with the funnel shown in the squeezed position.

Assembly 1400 is used the same as the assemblies of the prior embodiments, by first adding a quantity of liquid to be filtered to funnel 1330, and then placing the outlet port of base 1301 in fluid flow communication with a vacuum source; allowing the vacuum means to suck the unfiltered liquid through filter means 990, absorbent pad 991, through the outlet port of the base, into the vacuum means; venting the outlet port of the base to atmosphere; and then removing the funnel from the base by squeezing the outside opposite faces of the funnel as shown in FIG. 45b by arrows 1320; thereby causing the opposite faces of the funnel that are squeezed to distort inward as shown in FIG. 45b; thereby causing the bottom of the funnel to bow as shown in FIG. 46b; thereby causing the one or more integral flexible seal rings 1337 to move away from the inner wall 1305 of the base 1301; thereby releasing the funnel 1330 from the base 1301 allowing the user to easily remove the funnel 1330 from base 1301. If the funnel contains a funnel stop, shown as funnel stop 1336 in FIG. 46b, the funnel stop will lift the bottom of the funnel up and away from the filter means as the funnel is squeezed, thereby eliminating any rubbing of the filter means by the bottom of the funnel as the funnel is removed from the base.

An eleventh embodiment of the filtration apparatus constructed in accordance with the principles of the present invention, is shown in FIG. 47 through FIG. 55. The filtration apparatus 1500 shown in FIG. 47 includes base 1501, absorbent pad 1591, filter element 1590, funnel 1530, and lid 1560. If the liquid to be tested is water based it is preferable that filter means 1590 and absorbent pad 1591 be hydrophilic, however if the liquid to be tested is a solvent it is preferable that filter means 1590 and absorbent pad 1591 be hydrophobic. Base 1501 is similar to base 901 of the eighth embodiment. Filtration apparatus 1500 may also be referred to as assembly 1500. Base 1501 includes radial pad support ribs 1507 similar to radial pad support ribs 7 of base 1 of the first embodiment and circular pad support rib 1596. Base 1501 also includes filter seal surface 1511; inner surface 1505 of side wall 1513 that is preferably textured; flange 1503; outlet port 1510; funnel well 1526 bounded by inner surface 1505 and a plane that goes through filter seal surface 1511; and pad well 1527 bounded by side wall 1508 and a plane that goes through the top surface of radial pad support ribs 1507. Base 1501 further includes lid clamp ring 1504 that includes top surface 1522, end surface 1523, and bottom surface 1528, lid clamp ring 1504 could be replaced with one or more lid clamp tabs as previously described; flange 1503. If either the top surface, or the bottom surface, or both surfaces, of the lid clamp ring are sloped, the top surface may intersect the bottom surface at a sharp edge, thereby making the height of the end surface of the lid clamp ring equal to zero. The lid clamp ring or lid clamp tabs of the base will include the same features as the lid clamp ring or lid clamp tabs of the funnel, said features being described below.

Figure 47:
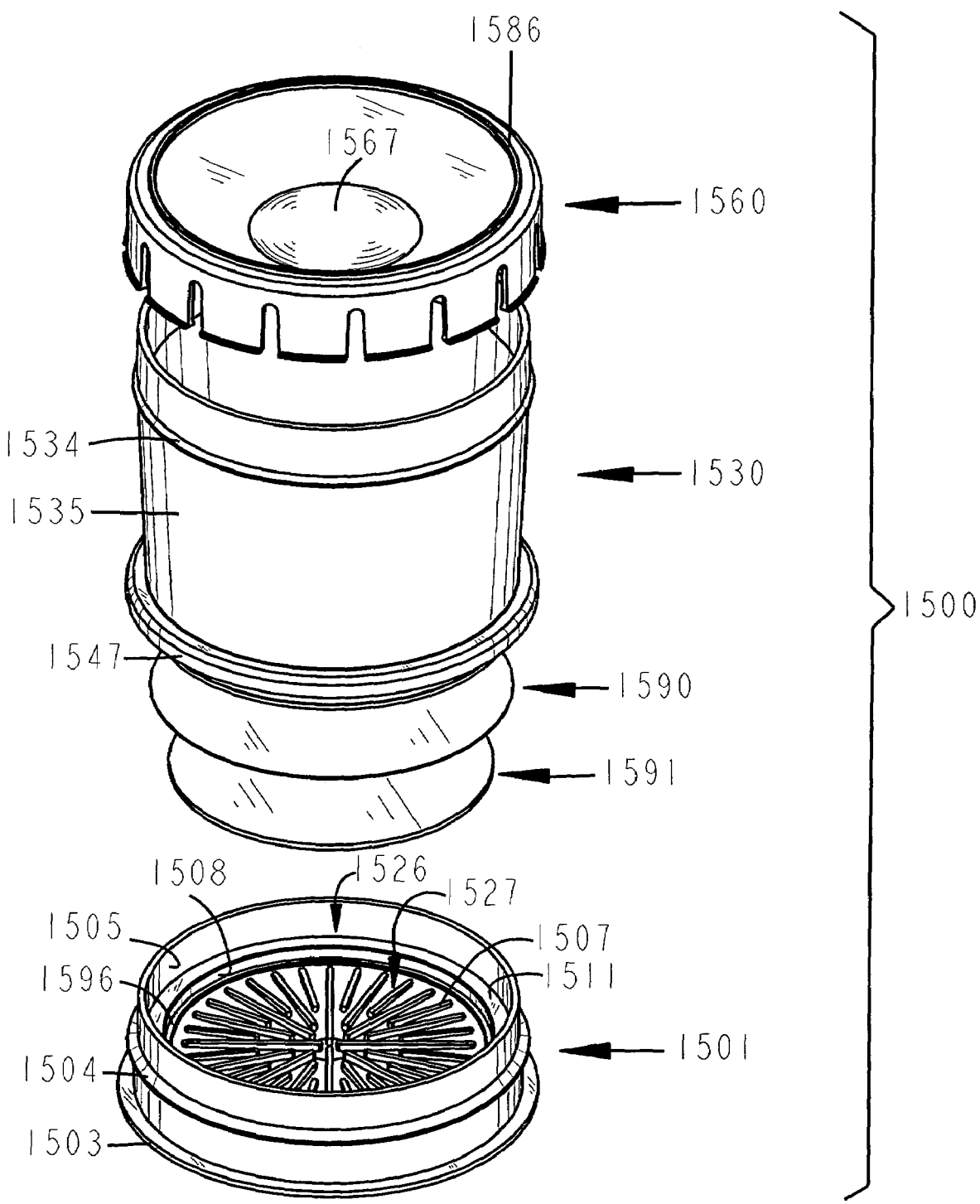
FIG. 47 is an exploded isometric view of the components that comprise the twelfth embodiment of the filtration apparatus, constructed in accordance with the principles of the present invention, usable for detecting microorganisms and particulates in liquid samples.
Figure 49:
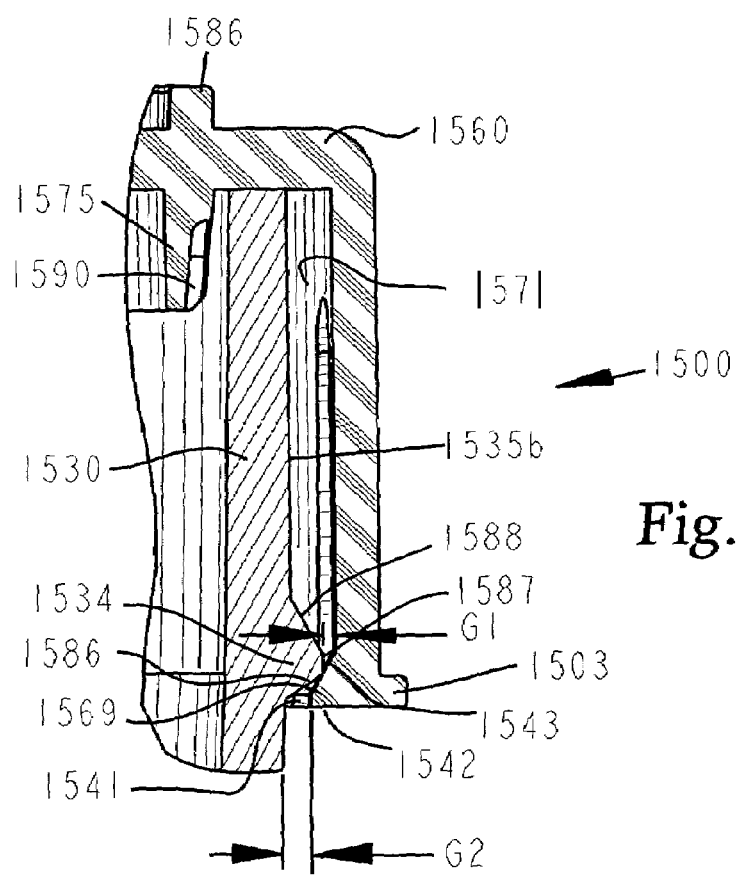
FIG. 49 is a partial cross-sectional view of the filtration apparatus shown in FIG. 48 showing details of how the lid is attached to the funnel.
Figure 50:
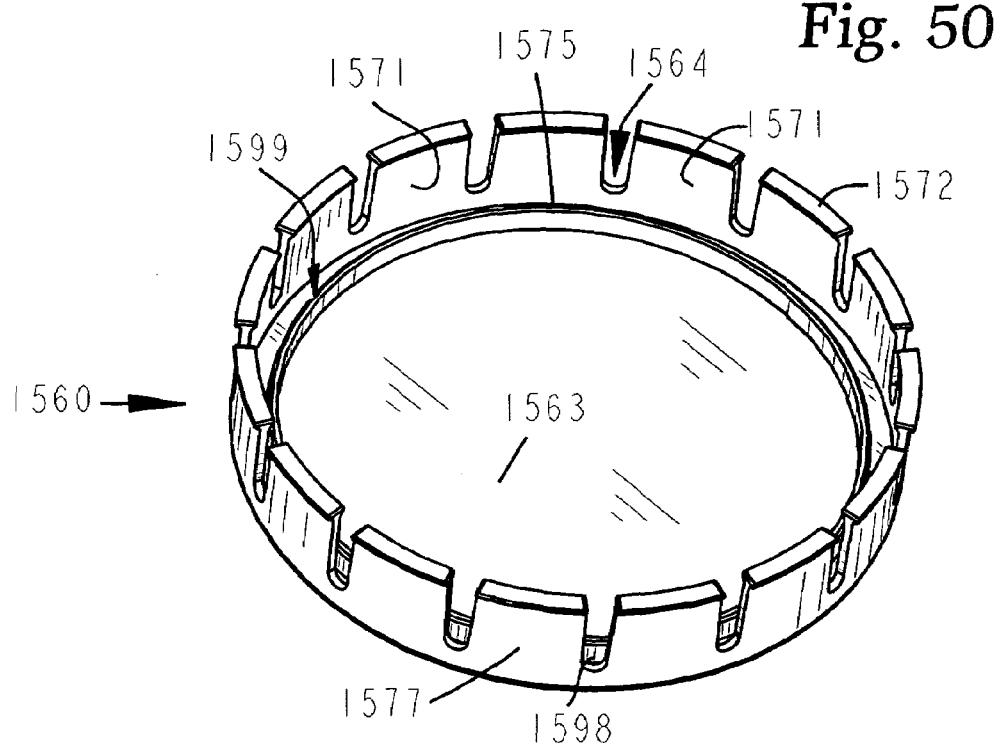
FIG. 50 is a bottom isometric view of the lid depicted in FIGS. 47 through 49.
Figure 51:
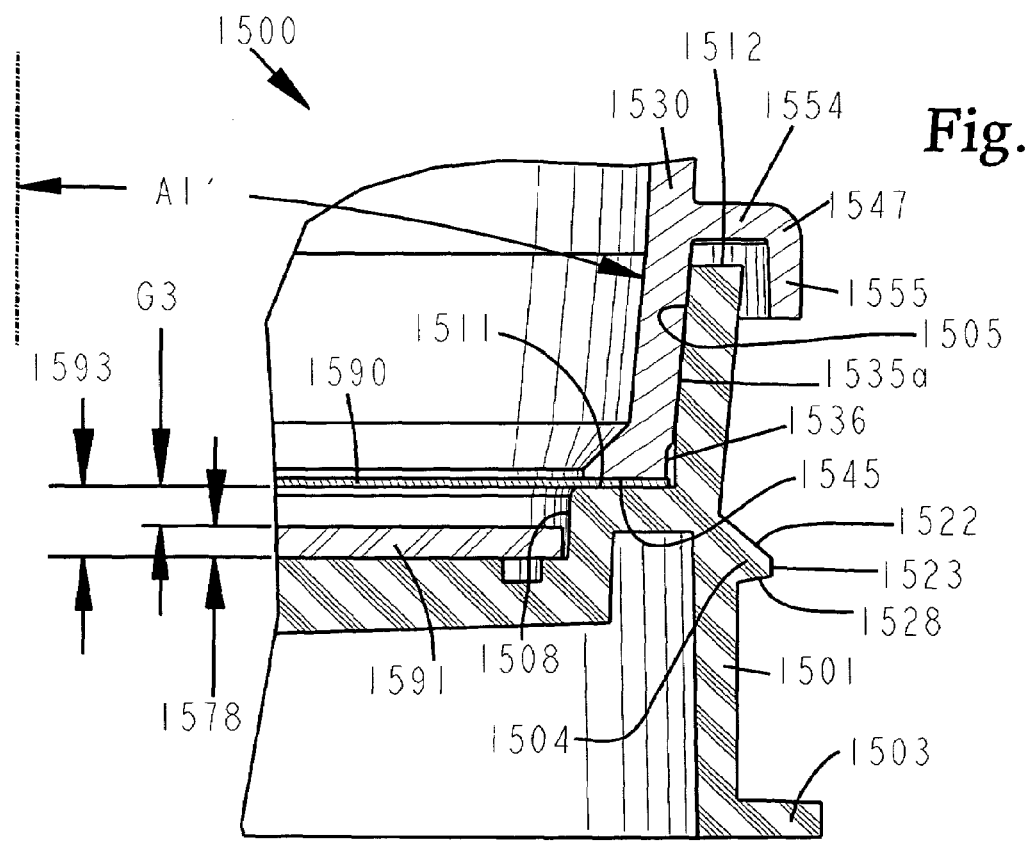
FIG. 51 is a partial cross-sectional view of the filtration apparatus shown in FIG. 48 showing details of how the funnel is attached to the base, and also showing details of the filter element and the absorbent pad in their dry state.

Referring to FIGS. 47 and 51, funnel 1530 is similar to funnel 1030 of the ninth embodiment and funnel 930 of the eighth embodiment, and is releasably attached to base 1501 with an interference fit the same way that funnel 1030 is releasable attached to base 1001 as shown in FIGS. 41a through 41d, and as described in the description of the ninth embodiment. Funnel 1530 includes cover ring 1547 that includes substantially horizontal portion 1554 and a substantially vertical portion 1555; outside wall 1535 includes bottom outside wall 1535a that preferably includes a textured surface and top outside wall 1535b; and step 1536. As shown in FIGS. 49 and 58, lid clamp ring 1534 protrudes outward from outside wall 1535 and includes, top surface 1588, end surface 1587, and bottom surface 1586. If either the top or the bottom surface of the lid clamp ring are sloped, or if both surfaces are sloped, the top surface may intersect the bottom surface, thereby making the height of the end surface equal to zero. Lid clamp ring 1534 could be replaced with of one or more lid clamp tabs including a top surface 1588, an end surface 1587, and a bottom surface 1586. In the upper limit a single lid clamp tab that forms a continuous loop becomes a lid clamp ring. Preferably the intersection of the top surface of the lid clamp ring and the outside wall of the funnel is disposed below the top surface of the funnel, as shown in the FIGS. 57 to 59. However, the top surface of the lid clamp ring can protrude from the top surface of the funnel. Base 1601 shown in FIGS. 56 and 57 which includes an integral funnel, includes lid clamp ring 1534' that is the same as lid clamp ring 1534. Funnel 1530" shown in FIGS. 58 and 59 includes lid clamp ring 1534" that includes, top surface 1588", end surface 1587", and bottom surface 1586". As will be described below, a lid clamp ring of a funnel, or of a base, of this embodiment of the present invention will include a top surface that may be horizontal or sloped, a bottom surface that may be horizontal or sloped, and an end surface that may be vertical or sloped. The funnel may also include one or more vent slots 33 shown in FIG. 8. The lid clamp rings or lid clamp tabs just described are interchangeable.

Figure 56:
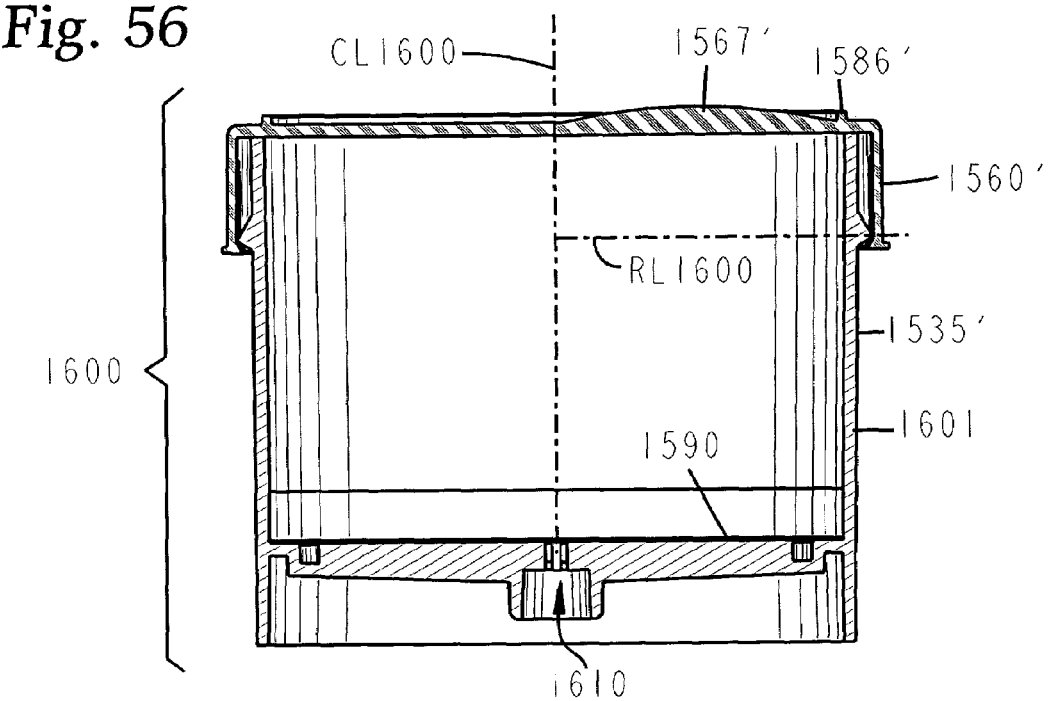
FIG. 56 is a cross-sectional view of the components that comprise the thirteenth embodiment of the filtration apparatus, constructed in accordance with the principles of the present invention, usable for detecting microorganisms and particulates in liquid samples, in which the funnel is an integral part of the base.
Figure 57:
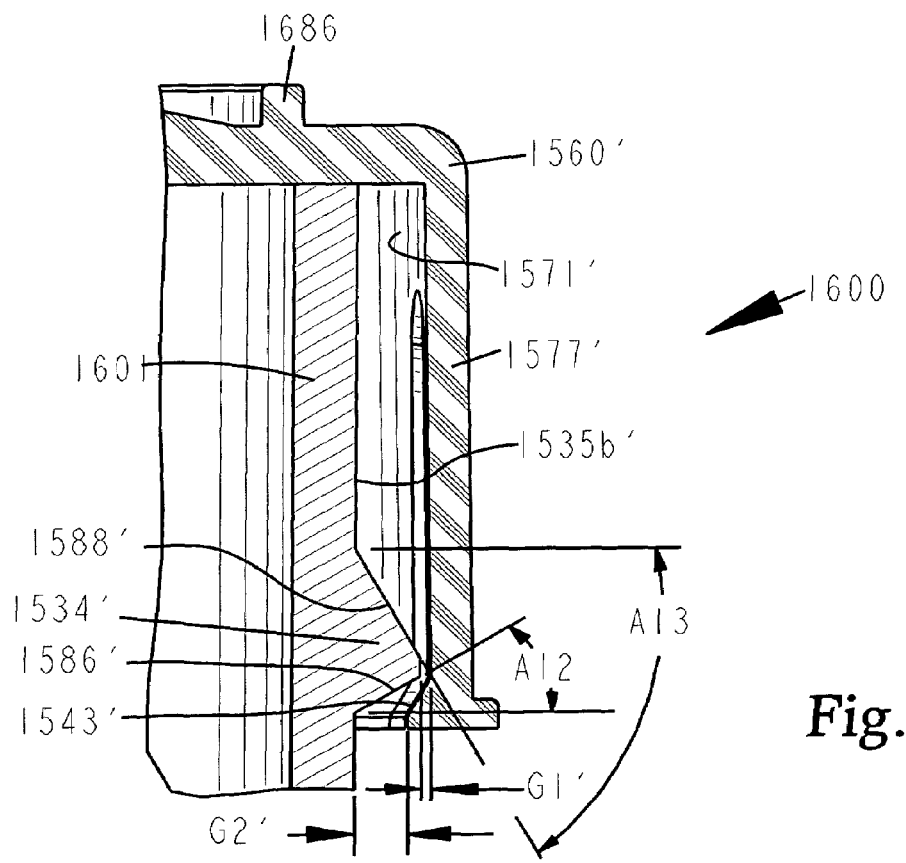
FIG. 57 is a partial cross-sectional view of the filtration apparatus shown in FIG. 56 showing details of how the lid is attached to the funnel.
Figure 58:
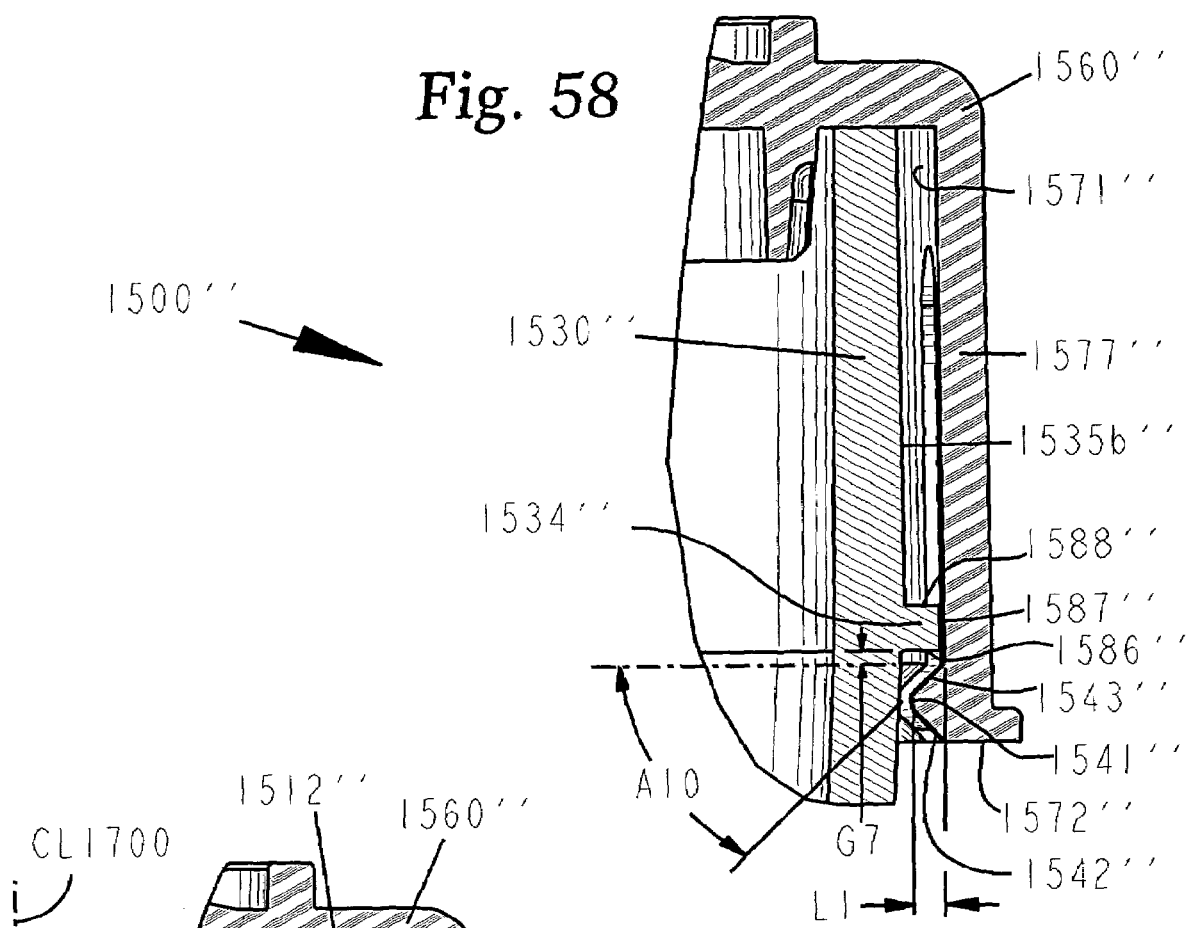
FIG. 58 is a partial cross-sectional view of the filtration apparatus shown in FIG. 47 showing details of how the lid is attached to the funnel, also showing a variation of the lid clamp ring of the funnel, with the lid shown in the assembled state.
Figure 59:
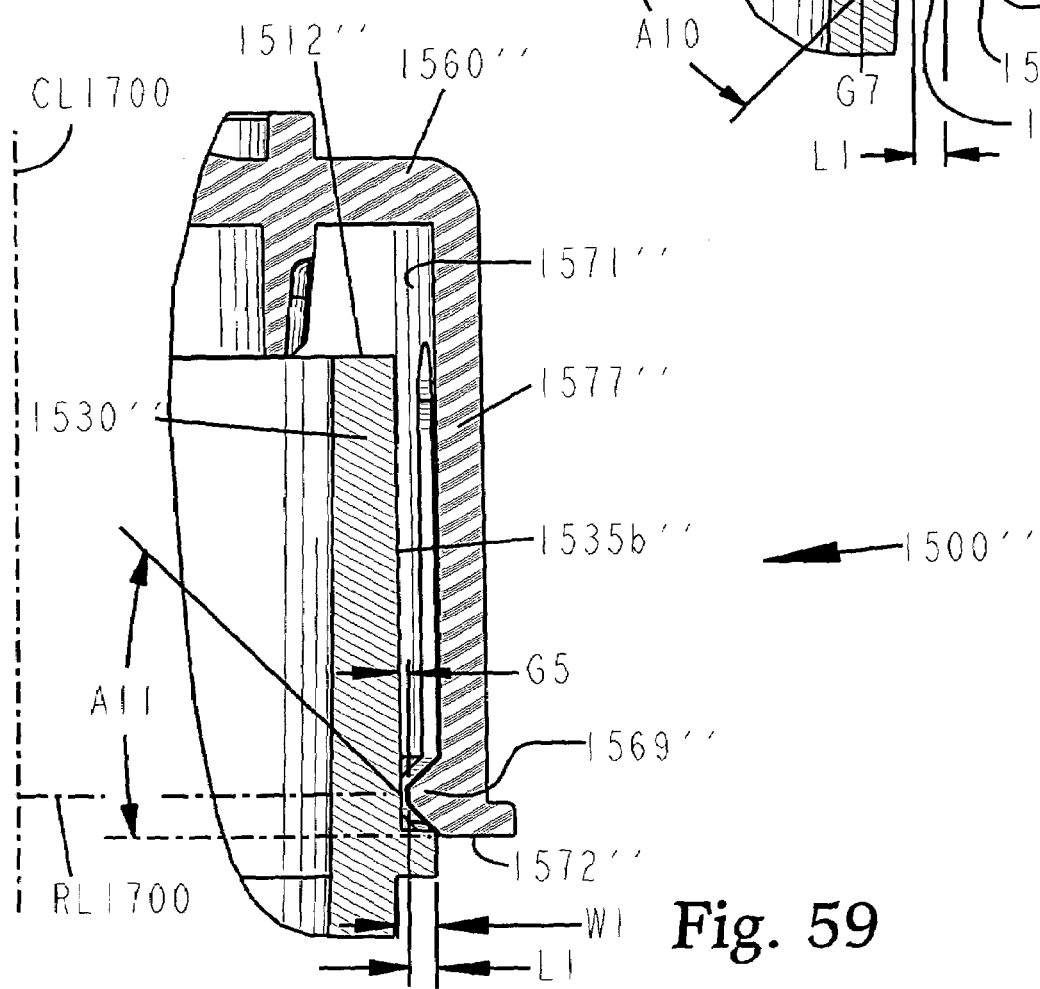
FIG. 59 is a partial cross-sectional view of the filtration apparatus shown in FIG. 47 showing details of how the lid is attached to the funnel, also showing a variation of the lid clamp ring of the funnel, with the lid shown in the pre-assembled state.

Referring to FIGS. 47 through 50, and FIGS. 53 through 59, lid 1560 is similar to lid 60 and lid 960. Outer wall 1577 of lid 1560 contains a plurality of slots 1564, with each slot creating a gap in bottom surface 1572 of lid 1560 similar to the slots in lids 60 and 960, thereby dividing the outer wall 1577 into a plurality of segments, thereby allowing outer wall 1577 to flex as described in the first embodiment, even when made from a rigid material such as styrene, polycarbonate, or acrylic, and also allowing the wall to flex when made from non-elastomeric materials such as polypropylene, or polyethylene. Lid 1560 may include annular seal ring 1575 protruding from top inner surface 1563. Annular seal ring 1575 may include one or more vent slots 1599. Lid 1560 may also include magnifying lens 1567 and nest ring 1586. Outer wall 1577 includes inner surface 1571. At least one segment, and more preferably more than one segment, and most preferably all segments of outer wall 1577 of lid 1560 include an inward projection 1569 that protrudes inward from the bottom portion of inner surface 1571. Inward projection 1569" (shown in FIG. 58) includes top surface 1543", end surface 1541", and bottom surface 1542". If either or both of the top and bottom surfaces are sloped, the top surface may intersect the bottom surface, thereby making the height the end surface equal to zero. Lid 1560' shown in FIGS. 56 and 57 is the same as lid 1560 with the exception that lid 1560' does not include annular seal ring 1575. Lid 1560" shown in FIGS. 58 and 59 is the same as lid 1560 with the exception that bottom surface 1542" of inward projection 1569" is sloped. The relationship between the angles of the surfaces of the lid clamp ring or lid clamp tabs of the funnel, and the angles of the surfaces of the inward projection of the lid will be explained below. Lids 1560, 1560', 1560", and 1560''' are interchangeable and are used to illustrate variations of the inward projection of the lid.

Although the base, funnel, and the lid are shown round, they could be made from other shapes such as square, rectangular, oval, but are not limited to these shapes. It is however important that the components are of the same shape so that they can be assembled as described in this specification.

Figure 48:
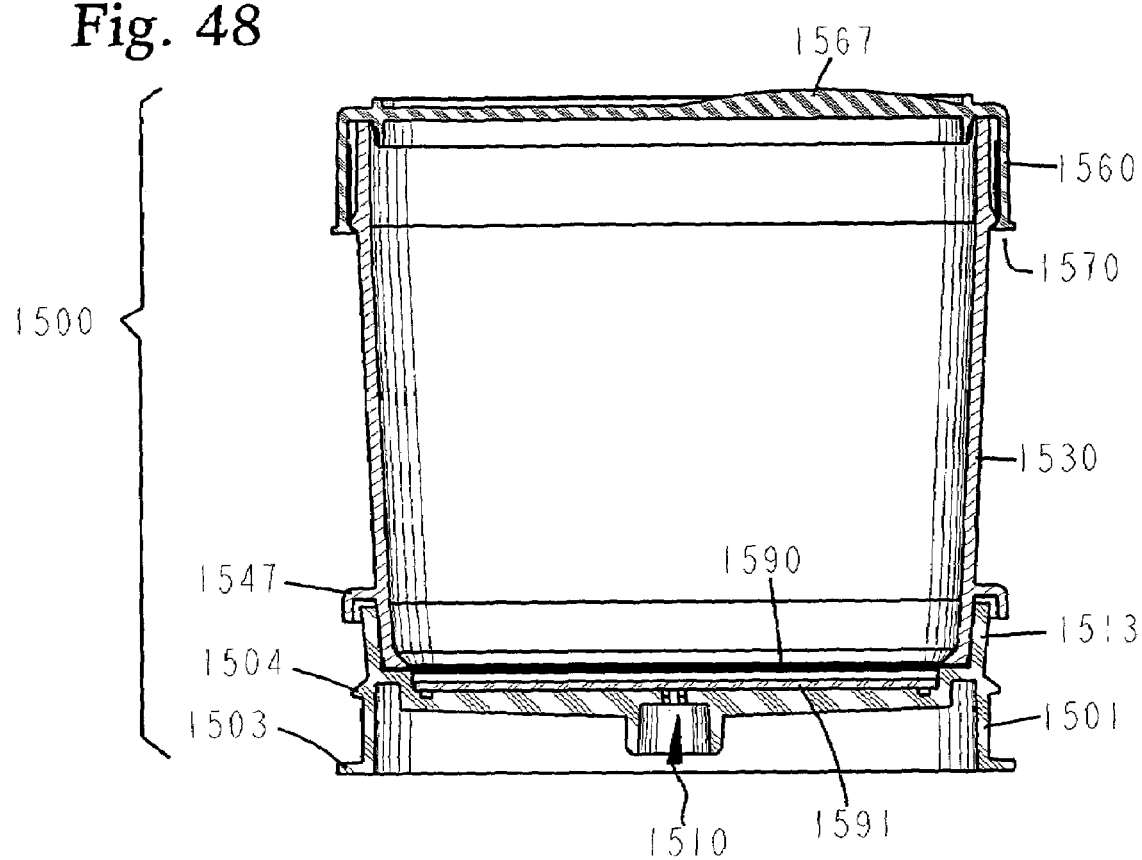
FIG. 48 is a cross-sectional view of the filtration apparatus shown in FIG. 47.

FIG. 48 shows a cross-section of filtration apparatus 1500 in its assembled state. FIG. 51 shows the bottom portion of filtration apparatus 1500 in the assembled state with angle A1' of the bottom outside wall 1535a of outside wall 1535 of funnel 1530 equal to or greater than the minimum deflected angle of inner surface 1505 of side wall 1513 of base 1501 as described in the description of the ninth embodiment. Therefore the entire part of the bottom outside wall 1535a of outside wall 1535 of funnel 1530 below top outside wall 1512 of base 1501 will contact inner surface 1505 of side wall 1513 of base 1501 to form an interference fit between inner surface 1505 of base 1501, and bottom outside wall 1535a of funnel 1530. The minimum deflected angle of inner surface 1505 of side wall 1513 of base 1501 is defined as the minimum angle at which the entire part of the bottom outside wall 1535a of outside wall 1535 of funnel 1530 below top outside wall 1512 of base 1501 will contact inner surface 1505 of side wall 1513 of base 1501 to form an interference fit. With funnel 1530 fully seated in base 1501 as shown in FIG. 51, filter element 1590 will be releasably sealed with a compression seal between filter seal surface 1545 of funnel 1530 and filter seal surface 1511 of base 1501. Filter element 590 could alternately be sealed to base 1501 with a non-releasable seal such as a heat seal, an ultrasonic seal, a glue seal, a solvent seal, or any other type of leak tight non-releasable seal. By making the base and funnel from the proper combination of materials (as described in the eighth and ninth embodiments), such as high density polyethylene for the base and styrene for the funnel, and by making the parts with the proper wall thickness, both the base and the funnel can be made to tolerances of at least ±0.004" while providing an adequate interference fit between the base and funnel, and also allowing the funnel to be fully inserted into the base so that the filter means can be reliably sealed with a compression seal between the filter seal surface of the base and the filter seal surface of the funnel.

FIG. 51 shows the height of pad well 1527 as dimension 1593, and the thickness of dry absorbent pad as dimension 1578. As shown in FIG. 51 the height 1593 of pad well 1527 is substantially greater than the thickness 1578 of dry absorbent pad 1591, so that a gap G3 exists between the top or upstream surface of absorbent pad 1591, and the bottom or downstream surface of filter element 1590, when both the filter means and absorbent are in their dry state.

FIG. 51 also shows cover ring 1547 that includes substantially horizontal annular portion 1554 and preferably includes substantially vertical annular portion 1555. Cover ring 1547 acts as a shield that prevents the user from touching the upper part of side wall 1513 of base 1501 when handling the apparatus and when removing the funnel from the base, thereby preventing contamination of critical surfaces, thereby preventing false positives during the incubation cycle when the apparatus is used to detect bacteria, yeast, or mold. Filtration apparatus 1500 can replace assembly 1100 in FIGS. 44a and 44b, with cover ring 1547 of funnel 1530 replacing funnel stop 1147 of funnel 1130, in which case cams 1278 of vacuum base assembly 1200 would clamp down on the upper surface of substantially horizontal portion 1554 of cover ring 1547 of funnel 1530. Flange 1503 of base 1501 provides a means for the user to firmly grasp the bottom portion of the base, while removing the funnel from the base, or while attaching the lid onto the base thereby further preventing the user from touching the upper part of side wall 1513 of base 1501, thereby further preventing contamination of critical surfaces, In the following analysis of how the lid releasably attaches to the funnel for an apparatus constructed according to the eleventh embodiment of the present invention, the following definitions will be used:

(a) Referring to FIGS. 56 and 57, the value of the angle A13 of the slope of the top surface of a lid clamp ring (or of a lid clamp tab) of a funnel (shown as lid clamp ring 1534'), is defined by taking a cross-section through a plane that intersects both the vertical centerline of the funnel (shown as centerline CL1600), and a horizontal radial line that intersects both the vertical centerline of the funnel and the lid clamp ring (shown as RL1600); and measuring the angle A13 shown in the cross-section between the top surface of the lid clamp ring, and a horizontal line that passes through the intersection of the top surface of the lid clamp ring and the outside wall of the funnel (shown as top outside wall 1535b'). The value of the angle A13 of the slope of the top surface of a lid clamp ring of a funnel must be greater than or equal to zero degrees, and less than ninety degrees.

Figure 52:
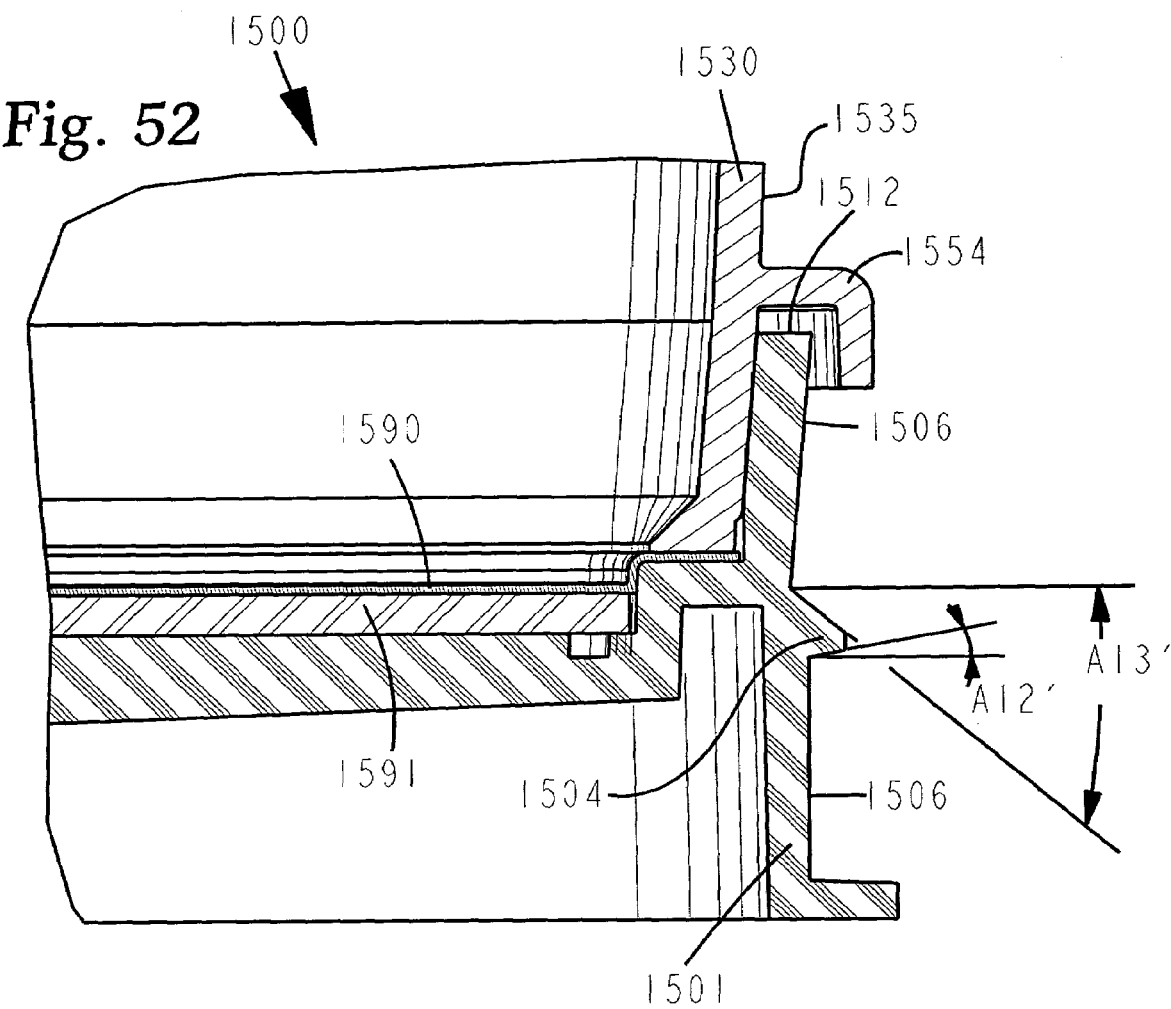
FIG. 52 is a partial cross-sectional view of the filtration apparatus shown in FIG. 51 showing details of the filter element and the absorbent pad after they have been wetted and after a differential pressure has been applied between the upstream side of the filter element and the downstream side of the absorbent pad.
Figure 53:
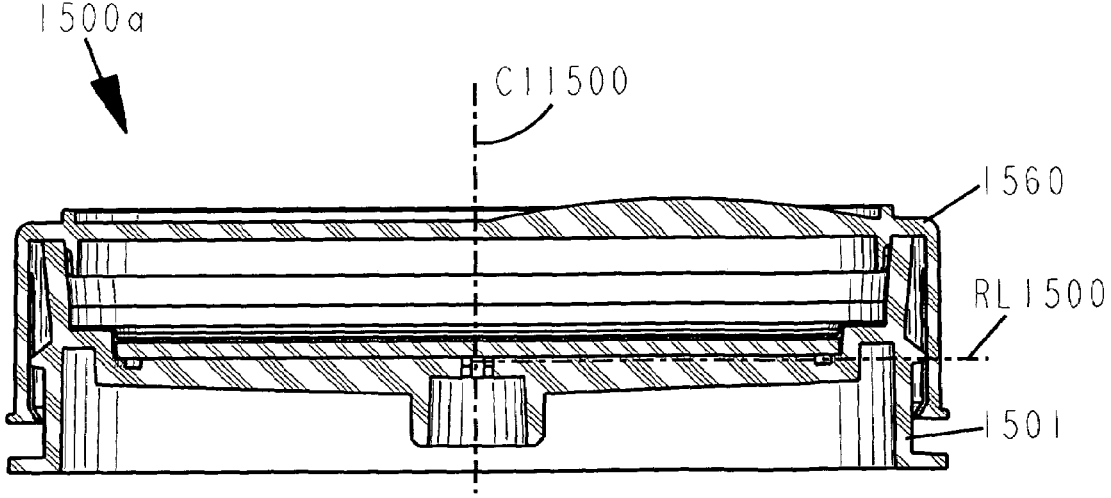
FIG. 53 is a cross-sectional view of the lid base assembly of the twelfth embodiment of the of the filtration apparatus, constructed in accordance with the principles of the present invention, usable for detecting microorganisms and particulates in liquid samples.

(b) Referring to FIGS. 52 and 53, the value of the angle A13' of the slope of the top surface of a lid clamp ring (or of a lid clamp tab) of a base (shown as lid clamp ring 1504), is defined by taking a cross-section through a plane that intersects both the vertical centerline of the base (shown as centerline CL1500), and a horizontal radial line that intersects both the vertical centerline of the base and the lid clamp ring (shown as RL1500); and measuring the angle A13' shown in the cross-section between the top surface of the lid clamp ring, and a horizontal line that passes through the intersection of the top surface of the lid clamp ring and the outside wall of the base (shown as outside wall 1506). The value of the angle A13' of the slope of the top surface of a lid clamp ring of a base must be greater than or equal to zero degrees, and less than ninety degrees.

(c) Referring to FIGS. 56 and 57, the value of the angle A12 of the slope of the bottom surface of a lid clamp ring (or of a lid clamp tab) of a funnel (shown as lid clamp ring 1534'), is defined by taking a cross-section through a plane that intersects both the vertical centerline of the funnel (shown as centerline CL1600), and a horizontal radial line that intersects both the vertical centerline of the funnel and the lid clamp ring (shown as RL1600); and measuring the angle A12 shown in the cross-section between the bottom surface of the lid clamp ring, and a horizontal line that passes through the intersection of the bottom surface of the lid clamp ring and the outside wall of the funnel (shown as top outside wall 1535b'). The value of the angle A12 of the slope of the bottom surface of a lid clamp ring of a funnel must be greater than or equal to zero degrees, and less than ninety degrees.

(d) Referring to FIGS. 52 and 53, the value of the angle A12' of the slope of the bottom surface of a lid clamp ring (or of a lid clamp tab) of a base (shown as lid clamp ring 1504), is defined by taking a cross-section through a plane that intersects both the vertical centerline of the base (shown as centerline CL1500), and a horizontal radial line that intersects both the vertical centerline of the base and the lid clamp ring of the base (shown as RL1500); and measuring the angle A12' shown in the cross-section between the bottom surface of the lid clamp ring, and a horizontal line that passes through the intersection of the bottom surface of the lid clamp ring and the outside wall of the base (shown as outside wall 1506). The value of the angle A12' of the slope of the bottom surface of a lid clamp ring of the base must be greater than or equal to zero degrees, and less than ninety degrees.

(e) Referring to FIGS. 58 and 59, the value of the angle A10 of the slope of the top surface of the inward projection of a lid (shown as inward projection 1569"), is defined by taking a cross-section through a plane that intersects both the vertical centerline of the lid (shown as centerline CL1700), and a horizontal radial line that intersects both the vertical centerline of the lid and the inward projection (shown as RL1700); and measuring the angle A10 shown in the cross-section between the top surface of the inward projection, and a horizontal line that passes through the intersection of the top surface of the inward projection and the inner surface of the lid (shown as inner surface 1571"). The value of the angle A10 of the slope of the top surface of the inward projection of a lid of must be greater than or equal to zero degrees, and less than ninety degrees.

(f) Referring to FIGS. 58 and 59, the value of the angle A11 of the slope of the bottom surface of the inward projection of a lid (shown as inward projection 1569"), is defined by taking a cross-section through a plane that intersects both the vertical centerline of the lid (shown as centerline CL1700), and a horizontal radial line that intersects both the vertical centerline of the lid and the inward projection (shown as RL1700); and measuring the angle A11 shown in the cross-section between the bottom surface of the inward projection, and a horizontal line that passes through the intersection of the bottom surface of the inward projection and the bottom surface of the lid (shown as bottom surface 1572"). The value of the angle A11 of the slope of the bottom surface of the inward projection of a lid of must be greater than or equal to zero degrees, and less than ninety degrees.

The relationship between the lid and the funnel or the lid and the base, and how the lid releasably attaches to the funnel or how the lid releasably attaches to the base, for apparatus constructed according to the eleventh embodiment of the present invention, can be best understood by referring to FIGS. 56 through 59. The relationship between the inward projection of a lid, and the lid clamp tab or lid clamp ring of a funnel, is the same as the relationship between the inward projection of a lid, and the lid clamp tab or lid clamp ring of a base. Referring to FIG. 59, lid 1560" is shown in its pre-assembled state with at least one segment of outer wall 1577" including an inward projection, with the bottom surface 1542" of the at least one inward projection 1569" of lid 1560" resting on top surface 1588" of lid clamp ring 1534" (or on the top surface of an at least one lid clamp tab) of funnel 1530". The value of gap G5 (shown in FIG. 59) between end surface 1541" of the at least one inward projection of the lid, and top outside wall 1535b" of the funnel, should be equal to, or greater than zero, but must be less than the width W1 of the lid clamp ring of the funnel. If either the top outside edge of the outside wall of the funnel includes a chamfer, or if the bottom surface of the inward projection of the lid is sloped, the value of gap G5 may be negative (i.e. end surface 1541" of the inward projection of the lid may be disposed inside of top outside wall 1535" of the funnel) when the bottom surface of the inward projection of the lid is disposed above the top surface of the funnel. As shown in FIG. 59 top surface 1588" of lid clamp ring 1534" is horizontal and bottom surface 1542" of inward projection 1569" is sloped with the value of angle A11 being greater than 0°. As lid 1560" is further pressed down onto funnel 1530", the sloped bottom surface 1542" of inward projection 1569" of lid 1560" will force the corresponding segment outer wall 1577" to bend outward until end surface 1541" of inward projection 1541" of lid 1560" presses against end surface 1587" of lid clamp ring 1534" of funnel 1530". As lid 1560" is further pressed down onto funnel 1530", the corresponding segment outer wall 1577" will snap inward to the position shown in FIG. 58, with the gap G1 (shown in FIG. 49) between the end surface of the lid clamp ring and the inner surface of the outer wall of the lid being greater than or equal zero, and with the overlap L1 shown in FIG. 59 between the end surface of the lid clamp ring of the funnel and the end surface of the inward projection of the lid being sufficiently greater than zero to prevent the lid from accidentally being disengaged from the funnel or from the base, and with the value of the gap G7 between the bottom surface of the lid clamp ring and the top surface of the inward projection being equal to or greater than zero. If the value of gap G7 is greater than zero the lid will fit onto the funnel with a loose fit, and if the value of gap G7 is equal to zero the lid will fit onto the funnel with a tight fit. Alternately as shown in FIG. 57, top surface 1588' of lid clamp ring 1534' may be sloped and the bottom surface of the inward projection of lid 1560' may be horizontal with the value of angle A13 being greater than 0°. As lid 1560' is pressed down onto base 1601 (that includes an integral funnel), the sloped top surface 1588' of lid clamp ring 1534' will force the corresponding segment of outer wall 1577' to bend outward until the end surface of the inward projection of lid 1560' presses against the end surface of lid clamp ring 1534'. As lid 1560' is further pressed down onto base 1601, the corresponding segment of outer wall 1577' will snap inward to the position shown in FIG. 57, with the gap G1' between the end surface of the lid clamp ring and the inner surface of the outer wall of the lid being greater than or equal zero. Alternately lid 1560" (shown in FIGS. 58 and 59) that includes an inward projection with a sloped bottom surface, could be releasably attached as just described to funnel 1530 (shown in FIG. 49), that includes a lid clamp ring with a sloped top surface. When the lid is fully seated onto the funnel the top surface of the inward projection of the lid may press against at least a portion of the bottom surface of the lid clamp ring of the funnel, with at least a portion of the top surface of the inward projection of the lid disposed below at least a portion of the bottom surface of the lid clamp ring of the funnel, as shown in FIG. 49. A lid including an inward projection that includes a bottom surface with a negative slope (i.e. angle A11 having a negative value) could be snap fitted onto a funnel that includes a lid clamp tab with a sloped top surface.

The above analysis shows that a lid constructed in accordance with the principles of the eleventh embodiment of the present invention can be releasably attached to a funnel or to a base if either the top surface of the one or more lid clamp tabs (or the lid clamp ring) of the funnel or of the base, or the bottom surface of the one or more inward protrusions of the lid, or both include a sloped surface, and that the value of the angle of the slope of at least one of these surfaces is sufficiently greater than zero degrees, so that the corresponding segment of the outer wall of the lid will be forced to bend outward as the corresponding bottom surface of the inward projection of the lid is pressed down against the top surface of the lid clamp ring of the funnel or of the base, until the end surface of inward projection of lid presses against end surface of lid clamp ring of funnel or of the base, and then as the lid is further pressed down onto the funnel or the base, the corresponding segment of the outer wall of the lid will snap inward with at least a portion of the top surface of the inward projection of the lid disposed below at least a portion of the bottom surface of the lid clamp ring, with a sufficient overlap between the end surface of the lid clamp ring and the end surface of the inward projection, to prevent the lid from being accidentally disengaged from the funnel or the base, with the value of the gap between the bottom surface of the lid clamp ring and the top surface of the inward projection of the lid being equal to or greater than zero, while also allowing the end user to place the lid onto the funnel or onto the base, by simply placing the lid onto the funnel or onto the base, and then pushing down on the lid.

The relationship between the lid and the funnel or between the lid and the base, and how the lid is removed from the funnel or the base, can be best understood by referring to FIGS. 56 through 59. Referring to FIG. 58, lid 1560" is shown in its assembled state with at least one segment of outer wall 1577" including an inward projection 1569", with at least a portion of the top surface 1543" of the at least one inward projection 1569" of lid 1560" disposed below at least a portion of bottom surface 1586" of lid clamp ring 1534" of funnel 1530". As shown in FIG. 58 bottom surface 1586" of lid clamp ring 1534" is horizontal and top surface 1543" of inward projection 1569" is sloped with the value of angle A10 being greater than 0°. As lid 1560" is lifted up, the sloped top surface 1543" of inward projection 1569" of lid 1560" will contact bottom surface 1586" of lid clamp ring 1534". Then as the lid is lifted up further, the corresponding segment of outer wall 1577" will be forced to bend outward until end surface 1541" of inward projection 1569" of lid 1560" presses against end surface 1587" of lid clamp ring 1534" of funnel 1530". As lid 1560" is further lifted up, the corresponding segment of outer wall 1577" will snap inward to the position shown in FIG. 59, with the gap G5 between the end surface 1541" of the inward projection, and the top outside wall 1535*b*" of the funnel being greater than or equal zero. The lid can now be easily lifted up until the lid is completely removed from the funnel. If gap G5 is equal to zero, the corresponding segment of outer wall 1577" may be bent outward. This is permissible as long as it is easy for the user to lift the lid up until the lid is completely removed from the funnel. Alternately as shown in FIGS. 54 and 55, bottom surface 1528' of lid clamp ring 1504', of base 1501', is sloped and the top surface of the inward projection of lid 1560' is horizontal with the value of angle A12' being greater than 0°. As lid 1560''' is lifted up, the horizontal top surface 1543''' of inward projection 1569''' of lid 1560''' will contact sloped bottom surface 1528' of lid clamp ring 1504'. Then as the lid is lifted up further, the corresponding segment of outer wall 1577''' will be forced to bend outward until end surface 1541''' of inward projection 1569''' of lid 1560''' presses against end surface 1523' of lid clamp ring 1504' of base 1501'. As lid 1560''' is further lifted up, the corresponding segment outer wall 1577''' will snap inward, with the gap between the end surface 1541''' of the inward projection, and the outside wall 1506' of the base being greater than or equal zero. The lid can now be easily lifted up until the lid is completely removed from the base. Alternately lid 1560" that includes an inward projection with a sloped top surface, could be removed as just described from funnel 1530, that includes a lid clamp ring with a sloped bottom surface.

Any of the arrangements just described which use a lid with a segmented outer wall, with at least one segment including an inward projection, with the lid being snap fitted onto one or more lid clamp tabs (or a lid clamp ring) of a funnel, or of a base, allows the funnel, or the base, and lid to be molded within a dimensional tolerance range of ±0.004" or greater, while providing an adequate fit between the lid and funnel, or between the lid and the base, to prevent accidental disengagement of the lid from the funnel or the base, while also allowing the end user to place the lid onto the funnel or the base, or to remove the lid from the funnel or the base, with one hand. The firmness of the interference fit can be adjusted by increasing the number of inward projections to increase the firmness, or by decreasing the number of inward projections to reduce the firmness, while keeping all other variables constant. A dimensional tolerance range of ±0.004" is well within the normal production range of dimensional tolerances.

The end user will use the vacuum filtration apparatus shown as assembly 1500 the same as assembly 100, assembly 200, assembly 700, and assembly 900 were used, as explained above. When the liquid to be tested is added to funnel 1530, filter means 1590 and absorbent pad 1591 will be wetted. Because filter means 1590 is very thin it will not swell appreciably in thickness, but will expand in diameter as it is wetted. Filter means 1590 will wrinkle if an absorbent pad with a thickness approximately equal to the height of pad well 1527 is used (as described in the previous embodiments of the present invention). This wrinkling will prevent portions of the downstream surface of filter means 1590 from contacting the upstream surface of absorbent pad 1591, which in turn will impede colony growth during the incubation cycle. However, when an absorbent pad that has a thickness that is substantially less than the height of the pad well is used as shown in FIG. 51 (with a releasable or non-releasable seal between filter means 1590 and base 1501), filter means 1590 will start out wrinkle free when dry, as shown in FIG. 51. After the filter means and the absorbent pad have been wetted the filter means will become pliable and will swell very little in thickness, but will swell appreciably in diameter, and the absorbent pad will swell appreciably in thickness as described above in previous embodiments. Once the filter means has been wetted, a vacuum is applied to the outlet port of the base, and the space above the un-filtered liquid in the funnel is vented to atmosphere as described above. The differential pressure between the upstream of the filter means and the downstream of the absorbent pad, created by the vacuum, will force the central portion of the filter means downward into a concave dish shape until the downstream surface of the central portion of the filter means is resting flat on the upstream surface of the swelled absorbent pad, with the upstream surface of the central portion of the filter means disposed below the filter seal surface of the base, with the downstream surface of the outer periphery of the filter means resting on the filter seal surface of the base, and with the portion of the downstream surface of the filter means between the central portion and the outer periphery of the filter means substantially conforming to the side wall of the pad well of the base, as shown in FIGS. 52 to 55. Because the thickness of absorbent pad 1591 is sufficiently greater than the thickness of filter means 1590, absorbent pad 991 will swell much more in thickness than filter means 990 will. Filter means 1590 will remain in this flat dish shaped state (wrinkle free) throughout the filtration cycle while a vacuum is applied to outlet port 1510, and remain in this flat dish shaped state wrinkle free when the filtration cycle is complete and outlet port 1510 has been vented to atmosphere. This will assure uniform contact between the downstream surface of filter means 1590 and the upstream surface of absorbent pad 1591, thus assuring proper incubation of any colonies trapped on the upstream surface of filter means 1590, during the incubation cycle. Referring to FIG. 51, the height the gap G3 between the downstream surface of the dry filter means and the upstream surface of the dry absorbent pad must have a value such that when a differential pressure is applied between the upstream of the wetted filter means and the downstream of the wetted absorbent pad, the differential pressure will force the central portion of the wetted filter means downward into a concave dish shape until the downstream surface of the central portion of the filter means is resting flat on the upstream surface of the wetted absorbent pad, with the upstream surface of the central portion of the filter means disposed below the filter seal surface of the base, with the downstream surface of the outer periphery of the filter means resting on the filter seal surface of the base, and with the portion of the downstream surface of the filter means between the central portion and the outer periphery of the filter means substantially conforming to the side wall of the pad well of the base, so that any wrinkles caused by the swelling of the wetted filter means are removed, without causing the wetted filter means to be stretched by the differential pressure. The advantage of having the wetted filter element in a flat concave dish shape as shown in FIG. 51, as opposed to the convex hump-shaped shape of the filter means and the absorbent pad shown in FIG. 28 and described in the sixth embodiment, is that when growth media is dispensed onto the upstream surface of the filter means after the filtration cycle is complete, it is much easier to evenly distribute a small quantity of growth media to a flat concave surface than it is to evenly distribute a small quantity of liquid growth media to a hump-shaped concave surface, thereby assuring even growth of bacteria, yeast, or mold over the entire surface of the filter element. Experimental data has shown this to be true. If the liquid to be tested is water based it is preferable that filter means 1590 and absorbent pad 1591 be hydrophilic, however if the liquid to be tested is a solvent it is preferable that filter means 1590 and absorbent pad 1591 be hydrophobic.

The differential pressure will be applied across the filter-absorbent pad combination as described in the previous paragraph until all of the liquid in the funnel has been filtered. The differential pressure will then be removed so that the pressure upstream of the filter means, and the pressure downstream of the absorbent pad, are at atmospheric pressure. Once the filtration cycle is complete, the user can proceed in any one of the four ways described in the eighth embodiment. If the first method of adding a quantity of liquid growth media to funnel 1530, and then to momentarily reapplying the vacuum to outlet port 1510 of base 1501 is used; the advantage of having the wetted filter element in a flat concave dish shape as shown in FIG. 51, as opposed to the convex hump-shaped shape of the filter means and the absorbent pad shown in FIG. 28, and described in the sixth embodiment, is that when growth media is dispensed onto the upstream surface of the filter means after the filtration cycle is complete, it is much easier to evenly distribute a small quantity of growth media onto a flat concave surface than it is to evenly distribute a small quantity of liquid growth media onto a hump-shaped concave surface, thereby assuring even growth of bacteria, yeast, or mold over the entire surface of the filter element. Experimental data has shown this to be true.

If it is desired to detect bacteria, yeast or mold, and it is also desired to do the incubation step with the filter in the base as described in the first and second options of the eighth embodiment, an apparatus constructed in accordance with the eleventh embodiment has the following advantages. FIGS. 53, 54, and 55, show the lid releasably attached to the base after the funnel has been removed. Lid 1560''' includes annular seal ring 1575 protruding from top inner surface 1563. Annular seal ring 1575 may include one or more vent slots 1599. Referring to FIG. 55, the lid 1560''' is releasably attached to base 1501' with the snap fit of the lid (as described above) preventing the lid from being accidentally removed from the base, and with the bottom outside edge of annular seal ring 1575 resting on the top edge of inner surface 1505' of base 1501', so that a seal is not created between annular seal ring 1575 and the inner surface 1505' of side wall 1513' of base 1501', thereby allowing the space between the top inner surface of the lid and the upstream surface of the filter means to be vented to atmosphere, through any irregularities between the bottom outside edge of annular seal ring and the top edge of inner surface the base. Annular seal ring 1575 may include one or more vent slots 1599, which would further increase this venting. Alternately, the annular seal ring may be eliminated, if it is desired to vent the space between the top inner surface of the lid and the upstream surface of the filter means during the incubation cycle. It has been found through experimentation that at least some bacteria grow better when the space between the top inner surface of the lid and the upstream surface of the filter means is not vented. If the lid includes an annular seal ring, the user has the second option shown in FIG. 54 of creating a seal between annular seal ring 1575 and the inner surface 1505' of side wall 1513' of base 1501', thereby sealing the lid to the base with a removable seal. To create this seal, the user will first press the lid onto the base as shown in FIG. 55 to create a releasable snap fit between the lid and the base, and then press the lid further onto the base as shown in FIG. 54, until the outer surface 1598 of annular seal ring 1575 is releasably sealed to inner surface 1505' of side wall 1513' of base 1501' with an interference fit. If the lid is made from a rigid material such as styrene, polycarbonate, or acrylic, and the side wall of the base is made from a flexible material such as high density poluethylene, or polypropylene, and if the bottom outside edge of the annular seal includes a chamfer as shown in FIG. 55, the outer wall of the base will be forced to bend outward as the annular seal ring is pressed into the base to form the interference fit shown in FIG. 54, thereby creating the proper interference fit even when the lid and base are made to within a tollerance of ±0.004", while still allowing the intereference fit to be broken by simply lifting up on the lid with respect to the base. Alternately, the lid could be constructed so that the snap fit and the interference fit occur simultaneously. One or more vent slots 1599 may be added to annular seal ring 1575 as shown in FIG. 54 with the top of the one or more vent slots being disposed below the top of the annular ring, so that venting of the space between the top inner surface of the lid and the upstream surface of the filter means will occur until the lid is fully seated onto the base, there by preventing pressure buildup in the space between the top inner surface of the lid and the upstream surface of the filter means as the lid is placed onto the base. If the base is made from a non-elastomeric material such as high density polyethylene, and an intereference fit is used between the base and the funnel, as shown in FIG. 51, then the inner surface 1505' of side wall 1513' of base 1501' shown in FIG. 54 will not spring bask to its original shape after the funnel is removed from the base, as shown in FIG. 54. It is therefore necessary that the annular seal ring be sized to take this deformation into account. Using this type of intereference fit between the annular seal ring and the inner surface of the base depends on the side wall of the base being made from a flexible material such as high density polyethylene, with the annular seal ring of the lid to be made from a rigid material such as styrene, acrylic, or polycarbonate. However, the annular seal ring could be made from any material that is sufficiently more rigid than the material from which the base is made.

Once the lid is releasably attached to the base as shown in FIG. 54 or in FIG. 55, the lid-base assembly will be inverted and placed into an oven for incubation as described above. When the incubation cycle is complete, the lid-base assembly will be removed from the oven. The lid may include lens 1567, which can be used to magnify the surface of the filter element to make it easier to count any colonies of bacteria, yeast, or mold that grew on the surface of the filter element during the incubation cycle. With the lid releasably attached to the base as shown in FIG. 55, the user can view a portion of the surface element through lens 1567, and then easily rotate the lid with respect to the base to view another portion of the filter element through the lens. If the lid is loosely snap fitted to the base as shown in FIG. 55, with a gap between the bottom surface of the lid clamp ring of the base and the top surface of the inward projection of the lid, the lid can be lifted so that the annular seal ring of the lid does not contact the top edge of the inner surface of the side wall of the base, thereby making it easier to rotate the lid with respect to the base. If the lid was placed onto the base as shown in FIG. 54 with a seal between the annular seal ring of the lid and the inner surface of the side wall of the base during the incubation cycle, the user need only lift the lid with respect to the base until the seal is broken as shown in FIG. 55 to be able to easily rotate the lid with respect to the base to utilize the lens as just described, while still keeping the lid releasably attached to the base with the snap fit between the lid and base.

Although the present invention has been shown and described in terms of specific preferred embodiments, it will be appreciated by those skilled in the art that changes or modifications are possible which do not depart from the inventive concepts described and taught herein. Such changes and modifications are deemed to fall within the purview of these inventive concepts. Any combination of the various features of the preferred embodiments are deemed to fall within the purview of these inventive concepts. It is also contemplated that any of the embodiments can be made disposable or reusable. In addition it is contemplated that the filter assembly may be employed in an environment other than the detection of microbes, or particulates. Any fluid system in which components of the fluid must be removed can benefit from the use of a filter apparatus embodying the teachings of the present invention.

What is claimed:

1. A vacuum filtration apparatus comprising:

a base including an outlet port capable of being adapted to a vacuum source, a filter seal surface disposed above said outlet port, and a pad well, said pad well containing a substantially vertical side wall and a bottom wall, with the boundary of the top of the side wall of the pad well being coincident with the inner boundary of the filter seal surface, with the bottom wall of the pad well being substantially parallel to the filter seal surface, and disposed entirely below the filter seal surface, an absorbent pad disposed in said pad well, with the downstream surface of said absorbent pad resting directly on the bottom wall of the pad well, a filter means, with the downstream surface of the outer periphery of the filter means in direct contact with the filter seal surface of the base, with the outer periphery of the filter means sealed to the vacuum filtration apparatus to prevent the flow of un-filtered liquid between the filter seal surface of the base and the downstream surface of the outer periphery of the filter means, with the portion of the downstream surface of the filter means disposed inside of the filter seal surface of the base disposed above the top surface of the absorbent pad, thereby creating a gap between the portion of the downstream surface of the filter means disposed inside of the filter seal surface of the base and the top surface of the absorbent pad, when both the filter means and the absorbent pad are dry, a funnel with an open top disposed above the filter seal surface of the base, said funnel forming a reservoir capable of holding un-filtered liquid upstream of the filter means, with the height of the gap between the downstream surface of the dry filter means and the upstream surface of the dry absorbent pad having a value such that when a differential pressure is applied between the upstream of the filter means, after the filter means has been wetted, and the downstream of the absorbent pad, after the absorbent pad has been wetted, the differential pressure will force a central portion of the wetted filter means downward into a concave dish shape until the downstream surface of the central portion of the wetted filter means is resting flat on the upstream surface of the wetted absorbent pad, with the upstream surface of the central portion of the wetted filter means disposed below the filter seal surface of the base, with the downstream surface of the outer periphery of the wetted filter means resting on the filter seal surface of the base, and with the portion of the downstream surface of the wetted filter means between the central portion and the outer periphery substantially conforming to the side wall of the pad well of the base, so that any wrinkles caused by the swelling of the wetted filter means are removed, without causing the wetted filter means to be stretched by the differential pressure.

* * * * *